US010342861B2

(12) United States Patent
Martinez-Sobrido et al.

(10) Patent No.: US 10,342,861 B2
(45) Date of Patent: Jul. 9, 2019

(54) ARENAVIRUS VACCINE

(71) Applicants: University of Rochester, Rochester, NY (US); The Scripps Research Institute, La Jolla, CA (US)

(72) Inventors: Luis Martinez-Sobrido, Rochester, NY (US); Juan Carlos De La Torre, San Diego, CA (US)

(73) Assignees: UNIVERSITY OF ROCHESTER, Rochester, NY (US); THE SCRIPPS RESEARCH INSTITUTE, La Jolla, CA (US)

(*) Notice: Subject to any disclaimer, the term of this patent is extended or adjusted under 35 U.S.C. 154(b) by 5 days.

(21) Appl. No.: 15/312,827

(22) PCT Filed: May 27, 2015

(86) PCT No.: PCT/US2015/032587
§ 371 (c)(1),
(2) Date: Nov. 21, 2016

(87) PCT Pub. No.: WO2015/183895
PCT Pub. Date: Dec. 3, 2015

(65) Prior Publication Data
US 2017/0196964 A1    Jul. 13, 2017

Related U.S. Application Data

(60) Provisional application No. 62/003,305, filed on May 27, 2014.

(51) Int. Cl.
| | | |
|---|---|---|
| *A61K 39/12* | (2006.01) | |
| *C07K 16/10* | (2006.01) | |
| *C07K 14/005* | (2006.01) | |
| *C12N 7/00* | (2006.01) | |
| *A61K 39/00* | (2006.01) | |

(52) U.S. Cl.
CPC ............ *A61K 39/12* (2013.01); *C07K 14/005* (2013.01); *C07K 16/10* (2013.01); *C12N 7/00* (2013.01); *A61K 2039/5254* (2013.01); *C07K 2317/76* (2013.01); *C12N 2760/10034* (2013.01)

(58) Field of Classification Search
None
See application file for complete search history.

(56) References Cited

U.S. PATENT DOCUMENTS

2012/0237922 A1*  9/2012  Tomaskova ............ C12Q 1/701
                                                435/5

2013/0267429 A1    10/2013  Gardner et al.
2015/0368622 A1    12/2015  Collins et al.

FOREIGN PATENT DOCUMENTS

| JP | 2009538603 A | 11/2009 | |
|---|---|---|---|
| WO | 2006008074 A1 | 1/2006 | |
| WO | 2006088493 A2 | 8/2006 | |
| WO | 2007140506 A1 | 12/2007 | |
| WO | 2012162428 A1 | 11/2012 | |
| WO | 2013006838 A1 | 1/2013 | |
| WO | WO2013/006838 * | 1/2013 | ............. A61K 39/00 |
| WO | 2014140301 A1 | 9/2014 | |

OTHER PUBLICATIONS

Borrow et al. Inhibition of the type I interferon antiviral response during arenavirus infection. Viruses. Nov. 2010;2(11):2443-80. ( Year: 2010).*
Albarino et al., "Efficient Reverse Genetics Generation of infectious Junin Viruses Differing in Glycoprotein Processing," Journal of Virology, Jun. 2009, vol. 83, No. 11, p. 5606-5614.
Albarino et al., "Efficient Rescue of Recombinant Lassa Virus Reveals the Influence of S Segment Noncoding Regions on Virus Replication and Virulence," Journal of Virology, Apr. 2011, vol. 85, No. 8, p. 4020-4024.
Cheng et al., "Generation of Recombinant Arenavirus for Vaccine Development in FDA-Approved Vero Cells," J. Exp. (78), e50662, doi:10.3791/50662 (2013).
Emonet et al., "Generation of recombinant lymphocytic choriomeningitis viruses with trisegmented genomes stably expressing two additional genes of interest," PNAS, Mar. 2009, 106(9):3473-3478.
Emonet et al. "Rescue from Cloned cDNAs and In Vivo Characterization of Recombinant Pathogenic Romero and Live-Attenuated Candid #1 Strains of Junin Virus, the Causative Agent of Argentine Hemorrhagic Fever Disease," Journal of Virology, Feb. 2011, vol. 85, No. 4, p. 1473-1483.
Enria et al., "Current status of the treatment of Argentine Hemorrhagic Fever," Med Microbiol Immunol, 1986, 175:173-176.
Enria et al., "Treatment of Argentine hemorrhagic fever," Antiviral Research 78 (2008) 132-139.
Falzarano et al., "Vaccines for viral hemorrhagic fevers—progress and shortcomings," Current Opinion in Virology, 2013, 3:343-351.
Jahrling et al., "Protection of Lassa Virus-Infected Guinea Pigs With Lassa-Immune Plasma of Guinea Pig, Primate, and Human Origin," Journal of Medical Virology, 12:93-102 (1983).
Jahrling et al., "Passive Antibody Therapy of Lassa Fever in Cynomolgus Monkeys: Importance of Neutralizing Antibody and Lassa Virus Strain," Infection and Immunity, May 1984, vol. 44, No. 2, p. 528-533.
Lauring et al., "Rationalizing the development of live attenuated virus vaccines," Nature Biotechnology, vol. 28, No. 6, 2010, p. 573-579.

(Continued)

*Primary Examiner* — Michelle S Horning
(74) *Attorney, Agent, or Firm* — Riverside Law LLP

(57) ABSTRACT

The invention relates to compositions and methods for preventing or treating arenavirus related diseases and disorders through the administration to a subject in need thereof a live-attenuated virus (LAV), wherein the LAV is a codon deoptimized (CD) arenavirus.

4 Claims, 25 Drawing Sheets

Specification includes a Sequence Listing.

(56) References Cited

OTHER PUBLICATIONS

Lee et al., "Reverse genetics of arenaviruses," Current topics in microbiology and immunology, 2002, 262:175-193.

Martinez-Sobrido et al., "Inhibition of the Type I Interferon Response by the Nucleoprotein of the Prototypic Arenavirus Lymphocytic Chonomeningitis Virus," Journal of Virology, Sep. 2006, vol. 80, No. 18, p. 9192-9199.

Martinez-Sobrido et al., "Differential Inhibition of Type I Interferon Induction by Arenavirus Nucleoproteins," Journal of Virology, Nov. 2007, vol. 81, No. 22, p. 12696-12703.

Martinez-Sobrido et al., "Identification of Amino Acid Residues Critical for the Anti-Interferon Activity of the Nucleoprotein of the Prototypic Arenavirus Lymphocytic Choriomeningitis Virus," Journal of Virology, Nov. 2009, vol. 83, No. 21, p. 11330-11340.

Monath et al., "Diagnosis of Lassa fever and the isolation and management of patients," Bull. World World Health Organ., 1975, 52:707-715.

Ortiz-Riano et al., "The C-Terminal Region of Lymphocytic Choriomeningitis Virus Nucleoprotein Contains Distinct and Segregable Functional Domains Involved in NP-Z Interaction and Counteraction of the Type I Interferon Response," Journal of Virology, Dec. 2011, vol. 85. No. 24, p. 13038-13048.

Ortiz-Riano et al., "Self-Association of Lymphocytic Choriomeningitis Virus Nucleoprotein is Mediated by its N-Terminal Region and is not Required for its Anti-Interferon Function," Journal of Virology, 2012, p. 3307-3317.

Ortiz-Riano et al., "D471G Mutation in LCMV-NP Affects its Ability to Self-associate and Results in a Dominant Negative Effect in Viral RNA Synthesis," Viruses, 2012, 4:2137-2161.

Ortiz-Riano et al., "Arenavirus reverse genetics for vaccine development," Journal of General Virology, 2013, 94:1175-1188.

Ortiz-Riano et al., "Inhibition of Arenavirus by A3, a Pyrimidine Biosynthesis Inhibitor," Journal of Virology, 2014, vol. 88, No. 2, p. 878-889.

Rodrigo et al., "Use of Single-Cycle Infectious Lymphocytic Choriomeningitis Virus to Study Hemorrhagic Fever Arenaviruses," Journal of Virology, Feb. 2011, vol. 85, No. 4, p. 1684-1695.

Yun et al., "Functional Interferon System is Required for Clearance of Lassa Virus," Journal of Virology, 2012, p. 3389-3392.

Yun et al., "Mice Lacking Functional STAT1 Are Highly Susceptible to Lethal Infection with Lassa Virus," Journal of Virology, 2013, 87(19):10908-10911.

\* cited by examiner

Figure 4

| | Nucleotide changes | Amino acid changes |
|---|---|---|
| rLCMV/NP$_{CD1}$ | A258G<br>G1401A | K86K (silent)<br>Q467Q (silent) |
| rLCMV/NP$_{CD2}$ | A255G<br>C813G | K85K (silent)<br>S271S (silent) |
| rLCMV/WT | NA | NA |

MGQIVTMFEALPHIIDEVINIVIVLIVITGIKAVYNFATCGIFALISFLLLAGRS
CGMYGLKGPDIYKGVYQFKSVEFDMSHLNLTMPNACSANNSHHYISMGTSGLELTE
TNDSIISHNFCNLTSAFNKKTFDHTLMSIVSSLIHLSIRGNSNYKAVSCDFNNGITI
QVNLTFSNAQSAQSQCRTFRGRVLDMFRTAFGGKYMRSGWGWTGSDGKTTWCSQTS
YQYLIIQNRTWENHCTYAGPFGMSRILLSQEKTKFFTRRLAGTFTWTLSDSSGVEN
PGGYCLTKWMILAAELKCFGNTAVAKCNVNHDEEFCDMLRLIDYNKAALSKFKEDV
ESALHLFKTTVNSLISDQLLMRNHLRDLMGVPYCNYSKFWYLEHAKTGETSVPKCW
LVTNGSYLNETHFSDQIEQEADNMITEMLRKDYIKRQGSTPLALMDLLMFSTSAYL
VSIFLHLVKIPTHRHIKGGSCPKPHRLTNKGICSCGAFKVPGVKTTVWKRR (SEQ ID NO: 22)

B)

LCMV GP$_{CD}$

| Mutations (nucleotides) | % CD (nucleotides) | Mutations (am

| LCMV WT | |
|---|---|
| Virion # | # of gold particles/virion |
| 1 | 8 |
| 2 | 12 |
| 3 | 17 |
| 4 | 9 |
| 5 | 9 |
| 6 | 14 |
| 7 | 10 |
| 8 | 8 |
| 9 | 13 |
| 10 | 12 |
| Average | 11.2 |
| Stdev | 2.936362073 |

B

| rLCMV cdGP | |
|---|---|
| Virion # | # of gold particles/virion |
| 1 | 0 |
| 2 | 0 |
| 3 | 1 |
| 4 | 1 |
| 5 | 2 |
| 6 | 1 |
| 7 | 0 |
| 8 | 0 |
| 9 | 0 |
| 10 | 0 |
| 11 | 2 |
| 12 | 1 |
| 13 | 2 |
| 14 | 0 |
| 15 | 0 |
| 16 | 1 |
| 17 | 0 |
| 18 | 0 |
| 19 | 1 |
| 20 | 1 |
| 21 | 1 |
| Average | 0.666666667 |
| Stdev | 0.730296743 |

Figure 12

*In vivo* attenuation of rLCMV/GP$_{CD}$ correlates with the degree of codon deoptimization

| Days p.i. (i.c. 10³ PFU) | % Survival (n=8) | | | | |
|---|---|---|---|---|---|
| | 6 | 7 | 8 | 12 | |
| PBS | 100 | 100 | 100 | 100 | |
| rLCMV/WT | 100 | 37.5 | 0 | - | |
| rLCMV/GP$_{CD}$ | 100 | 100 | 100 | 100 | |

Figure 14

Ability of rLCMV/GP$_{CD}$ to protect against a rLCMV/WT lethal challenge

| Days post-challenge (i.c. 10³ PFU; rLCMV/WT) | % Survival (n=8) | | | | | |
|---|---|---|---|---|---|---|
| | | 6 | 7 | 8 | 12 |
| Primary infection | PBS | 100 | 25 | 0 | - |
| | rLCMV/WT | 100 | 100 | 100 | 100 |
| | rLCMV/GP$_{CD}$ | 100 | 100 | 100 | 100 |

Nucleotide sequence

ATG GGT CAA GGT AAA TCG CGT GAA GAA AAA GGT ACG AAT TCG ACG
AAT CGT GCG GAA ATA TTA CCG GAT ACG TTT GAT TTA GGT CCG TTA
TCG TGT AAA TCG TGT TGG CAA CGT TTA TGT CAT GAT TAT TTA GGT TGT
CAT GAT CAT TAT CGT TGT CAT TGT AAA TAT CCG TTA CCG ACG CGT
GTA TCG GAT CGT TGT CCG CTA TCG TCG CCG CCG TAT GAA GAA
TTA AAA ATA TCG ACG GCG
TAA (SEQ ID NO: 14)

B

Deoptimized Codons

MGQGKSREEKGTNSTNRAEILPDTTYLGPLSCKSCWQKFDSLVRCHDHYLCRHCL
NLLSVSDRCPLCKYPLPTRLKISTAPSSPPYEE (SEQ ID NO: 23)

MGQIVTFFQEVPHVIEEVMNIVLIALSVLAVLKGLYNFATCGLVGL
VTFLLLCGRSCTTSLYKGVYELQTLELNMETLNMTMPLSCTKNNSH
HYIMVGNETGLELTLTNTSIINHKFCNLSDAHKKNLYDHALMSIIS
TFHLSIPNFNQYEAMSCDFNGGKISVQINLSHSYAGDAANHCGTVA
NGVLQTFMRMAWGGSYIALDSGRGNWDCIMTSYQYLIIQNTTWEDH
CQFSRPSPIGYLGLLSQRTRDIYISRRLLGTFTWTLSDSEGKDTPG
GYCLTRWMLIEAELKCFGNTAVAKCNEKHDEEFCDMLRLFDFNKQA
IQRLKAEAQMSIQLINKAVNALINDQLIMKNHLRDIMGIPYCNYSK
YWYLNHTTTGRTSLPKCWLVSNGSYLNETHFSDDIEQQADNMITEM
LQKEYMERQGKTPLGLV<u>DLFVFSTSFYLISIFILILVKIP</u><u>H H V</u>
<u>SC K</u> <u>NHM C C</u> <u>K G</u> <u>RM</u>

(SEQ ID NO: 26)

B)

LASV GP<sub>CD</sub>

| Mutations (nucleotides) | % CD (nucleotides) | Mutations (amino acids) | % CD (amino acids) |
|---|---|---|---|
| 379/1476 | 25.7 | 321/491 | 65.3 |

Figure

ARENAVIRUS VACCINE

CROSS-REFERENCE TO RELATED APPLICATIONS

This application is a U.S. national phase application filed under 35 U.S.C. § 371 claiming benefit to International Patent Application No. PCT/US2015/032587, filed May 27, 2015, which is entitled to priority under 35 U.S.C. § 119(e) to U.S. Provisional Patent Application No. 62/003,305 filed May 27, 2014, each of which application is hereby incorporated herein by reference in its entirety.

STATEMENT REGARDING FEDERALLY SPONSORED RESEARCH OR DEVELOPMENT

This invention was made with government support under Grant No. RO1 AI077719 awarded by the National Institutes of Health. The government has certain rights in the invention.

BACKGROUND OF THE INVENTION

Arenaviruses cause chronic infections of rodents across the world, and human infections occur through mucosal exposure to aerosols or by direct contact of abraded skin with infectious materials (Buchmeier et al., 2007, Ch. 50, pgs. 1791-1827 in Fields Virology Vol. II, Lippincott Williams & Wilkins). Both viral and host factors contribute to a variable outcome of arenavirus infection, ranging from virus control and clearance by the host defenses to subclinical chronic infection, to severe disease (Buchmeier et al., 2007, Ch. 50, pgs. 1791-1827 in Fields Virology Vol. II, Lippincott Williams & Wilkins). Several arenaviruses cause hemorrhagic fever (HF) disease in humans and pose a serious public health problem in their endemic regions (Buchmeier et al., 2007, Ch. 50, pgs. 1791-1827 in Fields Virology Vol. II, Lippincott Williams & Wilkins; Bray, 2005, Curr. Opin. Immunol. 17:399-403). Lassa virus (LASV) infects several hundred thousand individuals yearly in West Africa resulting in a high number of Lassa fever (LF) cases associated with high morbidity and mortality (Buchmeier et al., 2007, Ch. 50, pgs. 1791-1827 in Fields Virology Vol. II, Lippincott Williams & Wilkins; Bray, 2005, Curr. Opin. Immunol. 17:399-403). Recent studies indicate that LASV endemic regions continue to expand with a current population at risk of ~200 million people (Buchmeier et al., 2007, Ch. 50, pgs. 1791-1827 in Fields Virology Vol. II, Lippincott Williams & Wilkins; Bray, 2005, Curr. Opin. Immunol. 17:399-403). Hence, with Dengue fever exception, the estimated global burden of LF is the highest among viral HF (Buchmeier et al., 2007, Ch. 50, pgs. 1791-1827 in Fields Virology Vol. II, Lippincott Williams & Wilkins; Bray, 2005, Curr. Opin. Immunol. 17:399-403).

Notably, increased traveling to and from endemic regions has led to the importation of LF cases into non-endemic metropolitan areas around the globe (Freedman and Woodall, 1999, Med. Clin. North Am. 83:865-883). Likewise, Junin virus (JUNV) causes Argentine HF (AHF), a disease endemic to the Argentinean Pampas with hemorrhagic and neurological manifestations and a case fatality of 15-30% (Peters, 2002, Curr. Top. Microbiol. Immunol. 262:65-74). In addition, evidence indicates that the worldwide-distributed prototypic arenavirus lymphocytic choriomeningitis virus (LCMV) is a neglected human pathogen of clinical significance (Barton, 1996, Clin. Infect. Dis. 22:197; Jahrling and Peters, 1992, Arch. Pathol. Lab. Med. 116:489-488). Moreover, because their stability, high morbidity, potential for aerosol transmission and unrestricted source from their natural rodent hosts, several arenaviruses including LCMV, LASV and JUNV represent a credible bioterrorism threat and are considered Category A agents (Borio et al., 2002, J. Am. Med. Assoc. 116:486-488).

There are currently no FDA-approved vaccines against HF arenaviral diseases and current antiviral therapy to combat arenavirus infections is limited to an off-label use of ribavirin. However, ribavirin is only partially effective and has several limitations, including the need of intravenous and early administration for optimal efficacy, and significant side effects (Damonte and Coto, 2002, Adv. Virus. Res. 58:125-155; Jahrling et al., 1980, J. Infect. Dis. 141:580-589; McCormick et al., 1986, N. Engl. J. Med. 314:20-26; Rodriguez et al., 1986, Rev. Argent. Microbiol. 18:69-74). The JUNV live-attenuated Candid1 strain has been shown to be an effective vaccine against AHF (Enria et al., 2008, Antiviral Res. 78:132-139; Enria et al., 1986, Med. Microbiol. Immunol. 175:173-136). However, outside Argentina, Candid1 has only investigational new drug (IND) status and studies addressing long-term immunity and safety have not been conducted. Moreover, Candid1 does not protect against LASV.

Despite significant efforts dedicated to the development of LASV vaccines, not a single LASV vaccine candidate has entered a clinical trial although the MOPV/LASV reassortant ML29, as well as recombinant VSV and vaccinia virus expressing specific LASV antigens, have shown promising results (Falzarano and Feldmann, 2013, Curr. Opin. Virol. 3:343-351). Specifically, ML29 exhibited good safety and efficacy profiles in animal models, including non-human primates, of LASV infection (Falzarano and Feldmann, 2013, Curr. Opin. Virol. 3:343-351). However, the high prevalence of HIV within LASV-endemic regions raises safety concerns about the use of VSV- or vacciniabased platforms. Likewise, the mechanisms of ML29 attenuation remain poorly understood and additional mutations, including reversions, in ML29 or reassortants between ML29 and circulating virulent LASV strains, could result in viruses with enhanced virulence.

Nevertheless, the natural history of LASV infection and epidemiological studies in West Africa indicate that a live-attenuated vaccine (LAV) remains the most feasible and attractive approach to control LF (Falzarano and Feldmann, 2013, Curr. Opin. Virol. 3:343-351). Control of LASV infection seems to be mediated mainly by cellular immune responses, and significant titers of LASV neutralizing antibodies (NAbs) are usually observed only in patients who have clinically recovered (Jahrling and Peters, 1984, Infect. Immun. 44:528-233). However, passive antibody transfer has been shown to induce protection in animal models of LF (Jahrling, 1983, J. Med. Virol. 12:93-102) and in limited human studies (Monath and Casals, 1975, Bull. World Health Organ. 52:707-715) suggesting that a vaccine capable of inducing the right combination of cellular and humoral responses might be the preferred candidate. LAV are excellent candidates for the induction of both robust cellular and humoral immune responses following a single immunization (e.g. influenza), which would be desirable for vaccine use in rural areas of West Africa.

Arenaviruses are enveloped viruses with a bi-segmented negative-stranded (NS) RNA genome and a life cycle restricted to the cell cytoplasm (Buchmeier et al., 2007, Ch. 50, pgs. 1791-1827 in Fields Virology Vol. II, Lippincott Williams & Wilkins). Each genomic RNA segment, L (ca 7.3 kb) and S (ca 3.5 kb), uses an ambisense coding strategy to direct the synthesis of two polypeptides in opposite orientation, separated by a non-coding intergenic region (Buchmeier et al., 2007, Ch. 50, pgs. 1791-1827 in Fields Virology Vol. II, Lippincott Williams & Wilkins). The S RNA encodes the viral glycoprotein precursor (GPC) and the viral nucleoprotein (NP). GPC precursor is co-translationally cleaved by signal peptidase to produce a stable 58 amino acid stable signal peptide (SSP) and GPC that is post-translationally processed by the cellular site 1 protease (SIP) to yield the two mature virion glycoproteins GP1 and GP2 that form the spikes that decorate the virus surface (Buchmeier et al., 2007, Ch. 50, pgs. 1791-1827 in Fields Virology Vol. II, Lippincott Williams & Wilkins). GP1 is located at the top of the spike and mediates virus receptor recognition and subsequent cell entry via endocytosis, whereas GP2 mediates the pH-dependent fusion event required to release the virus ribonucleoprotein core into the cytoplasm of infected cells (Buchmeier et al., 2007, Ch. 50, pgs. 1791-1827 in Fields Virology Vol. II, Lippincott Williams & Wilkins). The L RNA encodes the viral RNA dependent RNA polymerase (L), and the small RING finger protein Z that has functions of a bona fide matrix protein (Perez et al., 2003, Proc. Natl. Acad. Sci. U.S.A. 110:9481-9486; Strecker et al., 2003, J. Virology 77:10700-10705).

The inability to genetically manipulate the arenavirus genome has hampered studies aimed at understanding its molecular and cell biology, as well as pathogenesis, and the ability to generate attenuated arenaviruses for vaccine development. Reverse genetics systems for the prototypic arenavirus LCMV have been developed (Emonet et al. 2011, J. Virology 85:1473-1483; Lee and de la Torre, 2002, Curr. Top. Microbiol. Immunol. 262:175-193). Subsequently, reverse genetics approaches for a variety of arenaviruses, including JUNV and LASV, have been developed (Emonet et al. 2011, J. Virology 85:1473-1483; Lee and de la Torre, 2002, Curr. Top. Microbiol. Immunol. 262:175-193; Albarino et al., 2009, J. Virology 83:5606-5614; Albarino et al., 2011, J. Virology 85:4020-4024; Ortiz-Riano et al., 2013, J. Gen. Virology 94:1175-1188). These systems have resulted in a novel and powerful tool for the investigation of the viral cis-acting sequences and proteins, both viral and cellular, that control cell entry, RNA replication, gene expression, assembly and budding of arenaviruses. Importantly, recombinant infectious arenaviruses with predetermined mutations in their genomes can be rescued and their phenotypes can be examined both in cultured cells and in validated animal models of infection (Emonet et al. 2011, J. Virology 85:1473-1483; Ortiz-Riano et al., 2013, J. Gen. Virology 94:1175-1188; Cheng et al., 2013, J. Vis. Exp. 78:doi: 10.3791/50662). Recombinant tri-segmented arenaviruses have been developed that permit the generation of recombinant arenaviruses expressing additional genes of interest (Ortiz-Riano et al., 2013, J. Gen. Virology 94:1175-1188; Cheng et al., 2013, J. Vis. Exp. 78:doi: 10.3791/50662; Emonet et al., 2011, Virology 411:416-425; Emonet et al., 2009, Proc. Natl. Acad. Sci. U.S.A. 106:3473-3478) as well as single-cycle infectious, reporter-expressing, recombinant LCMV in which GPC is replaced by GFP (rLCMVΔGPC/GFP) (Rodrigo et al., 2011, J. Virol. 85:1684-1695). Genetic complementation with plasmids or stable cell lines expressing arenavirus GPCs of interest produces the corresponding GPC-pseudotyped rLCMVΔGPC/GFP that can be used to assess NAb responses to HF-causing arenaviruses using a Biosafety Level 2 (BSL2) platform (Rodrigo et al., 2011, J. Virol. 85:1684-1695).

Thus, there is a need in the art for an effective LAV therapy which protects against arenavirus associated diseases and disorders. The present invention addresses this unmet need in the art.

SUMMARY OF THE INVENTION

In one aspect, the present invention provides an immunological composition comprising a live-attenuated virus (LAV). The LAV is a codon deoptimized (CD) arenavirus comprised of at least one CD polynucleotide encoding at least one of viral nucleoprotein (NP), glycoprotein precursor (GPC), or matrix (Z) protein. In one embodiment, the arenavirus is lymphocytic choriomeningitis virus (LCMV), Lassa virus (LASV), Lujo virus (LUJV), Junin virus (JUNV), Machupo virus (MACV), Guanarito virus (GTOV), Sabia virus (SABV), Chapare virus (CHPV), Ocozocoautla de Espinosa virus (OCEV), or Whitewater Arroyo virus (WWAV).

In one embodiment, the at least one protein comprises NP. In one embodiment, the one CD polynucleotide comprises a nucleic acid sequence selected from the group consisting of SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In one embodiment, the at least one protein comprises GPC. In one embodiment, the at least one CD polynucleotide comprises a nucleic acid sequence selected from the group consisting of SEQ ID NO: 13, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, and SEQ ID NO: 49.

In one embodiment, the at least one protein comprises Z. In one embodiment, the at least one CD polynucleotide comprises a nucleic acid sequence selected from the group consisting of SEQ ID NO: 15, SEQ ID NO: 16, SEQ ID NO: 17, SEQ ID NO: 18, SEQ ID NO: 19, and SEQ ID NO: 20.

In one aspect, the present invention provides a method for treating or preventing an arenavirus infection or an arenavirus related disease or disorder. The method comprises administering an immunological composition comprising a live-attenuated virus (LAV), wherein the LAV is a codon deoptimized (CD) arenavirus comprised of at least one CD polynucleotide encoding at least one of viral nucleoprotein (NP), glycoprotein precursor (GPC), of matrix (Z) protein.

In one embodiment, the arenavirus is lymphocytic choriomeningitis virus (LCMV), Lassa virus (LASV), Lujo virus (LUJV), Junin virus (JUNV), Machupo virus (MACV), Guanarito virus (GTOV), Sabia virus (SABV), Chapare virus (CHPV), Ocozocoautla de Espinosa virus (OCEV), or Whitewater Arroyo virus (WWAV).

In one embodiment, the at least one protein comprises NP. In one embodiment, the one CD polynucleotide comprises a nucleic acid sequence selected from the group consisting of SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In one embodiment, the at least one protein comprises GPC. In one embodiment, the at least one CD polynucleotide comprises a nucleic acid sequence selected from the group consisting of SEQ ID NO: 13, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, and SEQ ID NO: 49.

In one embodiment, the at least one protein comprises Z. In one embodiment, the at least one CD polynucleotide comprises a nucleic acid sequence selected from the group consisting of SEQ ID NO: 15, SEQ ID NO: 16, SEQ ID NO: 17, SEQ ID NO: 18, SEQ ID NO: 19, and SEQ ID NO: 20.

In one embodiment, the arenavirus related disease or disorder is selected from the group consisting of lymphocytic choriomeningitis, hemorrhagic fever (HF), Lassa hemorrhagic fever, Argentine hemorrhagic fever (AHF), Bolivian hemorrhagic fever, Brazilian hemorrhagic fever, Venezuelan hemorrhagic fever, Chapare hemorrhagic fever, and Lujo hemorrhagic fever.

In one aspect, the present invention provides a method of immunizing a subject against an arenavirus. The method comprises administering an immunological composition comprising a live-attenuated virus (LAV), wherein the LAV is a codon deoptimized (CD) arenavirus comprised of at least one CD polynucleotide encoding at least one of viral nucleoprotein (NP), glycoprotein precursor (GPC), or matrix (Z) protein, to a tissue of the subject.

In one embodiment, the arenavirus is lymphocytic choriomeningitis virus (LCMV), Lassa virus (LASV), Lujo virus (LUJV), Junin virus (JUNV), Machupo virus (MACV), Guanarito virus (GTOV), Sabia virus (SABV), Chapare virus (CHPV), Ocozocoautla de Espinosa virus (OCEV), or Whitewater Arroyo virus (WWAV).

In one embodiment, the immunological composition is administered intranasally, intratracheally, orally, intradermally, intramuscularly, intraperitoneally, intravenously, or subcutaneously.

In one embodiment, the subject is not infected with an arenavirus at the time of said administering and the immunological composition induces a protective immune response. In one embodiment, the subject is a human.

In one aspect, the present invention provides a method of treating a subject infected with an arenavirus. The method comprises administering an immunological composition comprising a live-attenuated virus (LAV), wherein the LAV is a codon deoptimized (CD) arenavirus comprised of at least one CD polynucleotide encoding at least one of viral nucleoprotein (NP), glycoprotein precursor (GPC), or matrix (Z) protein, to a tissue of the subject.

In one embodiment, the arenavirus is lymphocytic choriomeningitis virus (LCMV), Lassa virus (LASV), Lujo virus (LUJV), Junin virus (JUNV), Machupo virus (MACV), Guanarito virus (GTOV), Sabia virus (SABV), Chapare virus (CHPV), Ocozocoautla de Espinosa virus (OCEV), or Whitewater Arroyo virus (WWAV).

In one embodiment, the immunological composition is administered intranasally, intratracheally, orally, intradermally, intramuscularly, intraperitoneally, intravenously, or subcutaneously.

In one embodiment, the subject is infected with an arenavirus at the time of said administering and the immunological composition induces a therapeutic immune response. In one embodiment, the subject is a human.

In one aspect, the present invention provides a composition comprising an isolated nucleic acid comprising at least one nucleic acid sequence selected from the group consisting of SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 16, SEQ ID NO: 17, SEQ ID NO: 18, SEQ ID NO: 19, SEQ ID NO: 20, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, and a nucleic acid sequence substantially homologous to such sequences.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A through FIG. 1D, depicts the expression and function of codon deoptimized (CD) NP. FIG. 1A depicts codon deoptimization. Underlined amino acids indicate amino acids in which the codons were modified by codon deoptimization, without altering amino acid sequence. Non-underlined amino acids indicates Methionine (M), or amino acid in wild-type (WT) NP (SEQ ID NO: 21) encoded by non-optimal codons. FIG. 1B is a series of panels depicting NP expression. HEK293T cells transfected with the indicated NP plasmids were evaluated at 48 h post-transfection by IFA and WB using an anti-HA pAb. FIG. 1C is a series of panels depicting viral replication and transcription. HEK293T cells were transfected with WT or CD NP plasmids together with pCAGGS L, a LCMV MG plasmid expressing GFP and Gaussia luciferase, and a SV40 Cypridina luciferase plasmid to normalize transfection efficiencies. At 48 h post transfection, MG activity was determined by GFP and luciferase expressions. FIG. 1D is a series of panels depicting inhibition of IFNb promoter activation. HEK293T cells were transfected with the indicated NP plasmids together with pIFNβ-GFP and pIFNβ-Firefly luciferase, and SV40 Renilla luciferase to normalize transfection efficiencies. At 24 h post transfection, cells were infected with SeV (MOI=3) and 18 h later, IFNβ promoter activation was evaluated by GFP and Firefly luciferase expressions.

FIG. 2A through FIG. 2D, depicts the characterization of CD NP chimeras. FIG. 2A is a schematic representation of CD NP chimeras. Numbers indicate amino acid regions containing CD (white) and WT (black) NP sequences. FIG. 2B is a table depicting nucleotide and amino acid changes in CD NP chimeras: Discrepancies between mutated codons and amino acid lengths indicated in FIG. 2A are due to codons that are already deoptimized in NP WT or that are encoded by Methionine. FIGS. 2C-2D depict CD NP chimeras expression levels. HEK293T cells transiently transfected with pCAGGS expression plasmids encoding WT and CD NP chimeras were evaluated at 48 h post-transfection for protein expression by IFA (FIG. 2C) and WB (FIG. 2D) using an anti-HA pAb. Empty (E) plasmid transfected cells were included as control and GAPDH expression levels were used as a loading control. Numbers indicate the % of CD NP expression compared to WT after normalization with GAPDH.

FIG. 3A through FIG. 3F, depicts the functional characterization of CD NP chimeras. FIGS. 3A-3C depict the results of experiments characterizing viral replication and transcription. HEK 293T cells were transfected (triplicates) with the indicated NP expression plasmids together with L, a LCMV MG plasmid and SV40 Cypridina luciferase to normalize transfection efficiencies. FIG. 3A is a series of images depicting MG activity evaluated by GFP at 48 h post transfection. FIG. 3B is a graph depicting MG activity evaluated by Gaussia luciferase expression. FIG. 3C is a series of images of gels depicting NP expression determined by WB and normalized to GAPDH expression levels (loading control). Numbers indicate the % of CD NP expression compared to WT NP after normalization to GAPDH. FIGS. 3D-3F depict the results of experiments characterizing the inhibition of IFNβ promoter activation. HEK 293T cells (triplicates) were transfected with the indicated NP expression plasmids together with pIFNβ-GFP and pIFNβ-Firefly luciferase, and SV40 Renilla luciferase to normalized transfection efficiencies. At 24 h post transfection, cells were infected with SeV (MOI=3), and 18 h later, IFNβ promoter activity was determined by GFP (FIG. 3D) and Firefly luciferase (FIG. 3E). FIG. 3F is a series of images of gels depicting NP expression determined by WB and normalized to GAPDH levels (loading control). Numbers indicate the % of CD NP expression compared to WT NP after normalization with GAPDH.

FIG. 4, comprising FIG. 4A through FIG. 4D, depicts the characterization of rLCMV/NPcd. FIGS. 4A-4C: The growth kinetics of BHK-21, A549, and Vero cells were examined. BHK-21 (FIG. 4A), A549 (FIG. 4B) and Vero (FIG. 4C) cells were infected with the indicated rLCMV/NPcd chimeras (MOI=0.01) and viral titers in tissue culture supernatants (TCS) at the indicated times post infection were determined by immunofocus (FFU/ml) assay. FIG. 4D is a series of images of gels depicting the confirmation of rLCMV/NP$_{CD}$ by RT-PCR. BHK-21 cells were mock infected or infected (MOI of 0.01) with either rLCMV NP/$_{WT}$ or with rLCMV/NP$_{CD}$ chimeras. At 72 h p.i. cells were collected and rLCM viruses were characterized by RT-PCR using indicated primers. RT-PCR products were analyzed on a 1% agarose gel.

FIG. 5 is a table depicting the genetic stability of rLCMV NP$_{CD}$ chimeras. Vero cells were infected (MOI of 0.1) with rLCMV/NP$_{WT}$, NP$_{CD1}$ and NP$_{CD2}$ viruses. At 48 h p.i., TCS were collected and used to infect (1:10 dilution) fresh Vero cells for a total of 10 passages. Total RNA from last passage-infected Vero cells were extracted and used for RT-PCR LCMV NP. PCR products were sequenced and identified mutations in NP are indicated.

FIG. 6, comprising FIG. 6A through FIG. 6D, depicts the results of experiments demonstrating that codon deoptimization reduces LCMV GP protein expression. FIG. 6A depicts amino acid sequence of LCMV glycoprotein. Underlined amino acids indicate amino acids in which the codons were modified by codon deoptimization, without altering amino acid sequence. Non-underlined amino acids indicate amino acids already deoptimized or that encode either methionine (M) or tryptophan (W). FIG. 6B is a table depicting nucleotideand amino acid changes in LCMV GP$_{CD}$: Number of nucleotide and amino acid mutations and the percentage (%) of CD nucleotides and amino acids are indicated. FIG. 6C and FIG. 6D depict LCMV GPCD expression levels: Human 293T cells were transiently transfected with pCAGGS expression plasmids encoding wild-type (GP$_{WT}$) or codon deoptimized (GP$_{CD}$) LCMV GP and were evaluated at 48 h p.t. for protein expression by immunofluorescence assay (FIG. 6C) and Western blot (FIG. 6D) using the LCMV GP monoclonal antibody 83.6. Representative images are illustrated. Scale bar=100 μm. Empty plasmid (denoted as "E") was included as negative control in the Western blot. GAPDH expression levels were used as loading controls.

FIG. 8A through FIG. 8C, depicts the results of experiments investigating the growth kinetics of rLCMV/GP$_{CD}$. HA549 (FIG. 8A), BHK-21 (FIG. 8B), and Vero (FIG. 8C) cells were infected (MOI 0.01) with either rLCMV/WT or rLCMV/GP$_{CD}$. Viral titers in TCS at the indicated hours post infection were determined by immunofocus (FFU/ml) assay (left). Dotted line indicates the limit of detection (20 FFU/ml). Replicates of cells infected as before were evaluated for NP and GP expression levels by immunofluorescence assay (right) using the LCMV GP and NP monoclonal antibodies 83.6 and 1.1.3, respectively. DAPI was used for nuclear staining.

FIG. 9, comprising FIG. 9A through FIG. 9D, depict the results of experiments demonstrating that LCMV GP$_{CD}$ protein levels, but not mRNA expression, is affected by codon optimization. A549 (FIG. 9A) and BHK-21 (FIG. 9B) cells were mock infected (M) or infected (MOI of 0.01) with rLCMV/WT or rLCMV/GP$_{CD}$. At 48 hours post-infection, cells were collected and evaluated protein expression (FIG. 9A and FIG. 9B) using the LCMV GP monoclonal antibody 83.6. Beta-actin expression levels were used as loading controls.

FIG. 10B depicts the results of a morphological comparison of rLCMV/WT and rLCMV/GP$_{CD}$ virion particles. rLCMV/WT (FIG. 10A) and rLCMV/GPCD (FIG. 10B) virions were purified from BHK-21 infected (MOI 0.001) at 72 hours post-infection using a 20% sucrose cushion. Virion particle morphology was assessed by transmission electron microscopy (TEM) negative straining. As shown, both viruses have same viral morphology and viral sizes. Representative images are shown. Scale bar=100 nm FIG. 11, comprising

FIG. 12, comprising FIG. 12A and FIG. 12B, depicts the quantitative results of experiments using immunoelectron microscopy (TEM) to detect GP present in LCMV WT and rLCMV/GPcd virus, as measured by staining with monoclonal antibody 83.6. FIG. 12A is a series of tables depicting indicated numbers of purified WT (left) and GPcd (right) rLCM viruses counted for the amount of GP present in the surface of purified virions. FIG. 12B is a graph depicting the average number of gold particles per virion in purified WT (left) and GPcd (right) rLCM viruses. The presence of GP in was detected in rLCMV/WT but not in rLCMV/GPcd purified viruses, using the GP2 monoclonal antibody 83.6.

FIG. 13A through FIG. 13C, depicts the results of experiments examining the growth kinetics of r3LCMV/GP$_{CD}$: A549 (FIG. 13A), BHK-21 (FIG. 13B), and Vero (FIG. 13C) cells were infected (MOI 0.01) with either rLCMV/WT or rLCMV/GP$_{CD}$ and viral titers in TCS at the indicated hours post infection were determined by focus forming units (i). Gluc activity in same TCS was assessed by luminescence (ii). GFP expression from infected cells was determined by fluorescence microscopy (iii). Dotted line indicates the limit of detection (20 FFU/ml). Representative images are illustrated. Scale bar=100 μm.

FIG. 14 is a table demonstrating the in vivo attenuation of rLCMV/GP$_{CD}$. Six week-old male B6 mice (n=8) were infected (i.c, 10$^3$ PFU) with rLCMV/WT or rLCMV/GP$_{CD}$, or inoculated with the virus diluent, PBS. Mice were monitored daily for morbidity and mortality until the experimental endpoint (12 days p.i.).

FIG. 15 is a table demonstrating the ability of rLCMV/GP$_c$p to protect against a rLCMV/WT lethal challenge. Six week-old male B6 mice (n=8) were immunized with the indicated viruses (i.p., 10$^5$ PFU) or inoculated with the virus diluent (PBS) and four weeks later infected with rLCMV/WT (i.c., 10$^3$ PFU). Mice were monitored daily for morbidity and mortality.

FIG. 16, comprising FIG. 16A and FIG. 16B, depicts codon deoptimization (CD) of LCMV matrix (Z) protein. FIG. 16A depicts the nucleotide sequence of CD Z protein (SEQ ID NO: 14). FIG. 16B depicts the amino acid sequence of deoptimized codons (SEQ ID NO: 23). Changes at the nucleotide or amino acid on LCMV for codon deoptimization are indicated in red underlined text.

FIG. 17A through FIG. 17C, depicts the results of experiments illustrating the effect of codon deoptimization on LCMV Z expression. FIG. 17A is a schematic representation of LCMV wild-type (WT) and codon deoptimized (CD) Z constructs. FIG. 17B is a table indicating the percent of nucleotides and amino acid changes in LCMV Z. FIG. 17C is an image of a Western blot showing protein expression levels of LCMV WT and CD using immunofluorescence (top) and Western blot (bottom) assays.

FIG. 18A through FIG. 18C, depicts the characterization of codon deoptimized LCMV Z chimeras. FIG. 18A is a schematic representation of codon deoptimized LCMV Z chimeras. The number of amino acids that fall within the deoptimized regions of the chimeras are represented in the white bars. FIG. 18B is a table characterizing the percent deoptimization of each chimera. FIG. 18C depicts protein expression of Z chimeras using immunofluorescence assay (top) and western blot (bottom) in 293T cells.

FIG. 19A through FIG. 19F, depicts codon deoptimizated LCMV Z inhibition of viral replication and transcription as determined using a minigenome (MG) assay. FIG. 19A and FIG. 19B are each a series of images depicting LCMV MG expression as assessed by fluorescence microscopy. FIG. 19C and FIG. 19D are each a table depicting and LCMV MG expression as assessed by luciferase expression. Dotted line (- - -) represents LCMV MG expression upon co-transfection with empty plasmid. FIG. 19E and FIG. 19F are each an image of a Western blot determining protein expression levels of codon deoptimized Z. 293T cells were co-transfected with the vRNA expression plasmid pPOL-I LCMV GFP/Gluc (LCMV MG) and protein expression plasmids of LCMV NP, LCMV L, and either 25 ng (FIG. 19A, FIG. 19C, FIG. 19E) or 50 ng (FIG. 19B, FIG. 19D, FIG. 19F) of empty plasmid or the corresponding LCMV Z WT or chimeric constructs.

FIG. 20A and FIG. 20B, depicts the rescue and characterization of rLCM viruses expressing codon deoptimized Z chimeras. FIG. 20A is a schematic representation of LCMV Z chimeric constructs. FIG. 20B is a series of images of gels confirming rLCMV/ZCD chimeric viruses using RT-PCR. 1.5% gel; 110V, 45 min; gel was run with 15 µL of the 100 µL PCR reaction.

FIG. 21A and FIG. 21B, depicts growth kinetics of rLCMV/Zcd chimeras. Human A549 (FIG. 21A) and murine BHK-21 (FIG. 21B) cells were infected with rLCMV/Zcd chimeras 1-5 (moi 0.01) and LCMV WT (moi 0.001). At indicated times post-infection (12, 24, 48, 71 and 96 hours) tissue culture were collected and viral titers were calculate by immunofluorescence.

FIG. 22, comprising FIG. 22A through FIG. 22D, depicts the results of experiments demonstrating that codon deoptimization reduces LASV GP protein expression. FIG. 22A depicts the amino acid sequence of LASV glycoprotein. Amino acids modified by codon deoptimization are indicated in grey font. Amino acids already deoptimized or that encode either methionine (M) or tryptophan (T) are indicated in black. FIG. 22B is a table demonstrating the nucleotide and amino acid changes in LCMV GP$_{CD}$: Number of nucleotide and amino acid mutations and the percentage (%) of CD nucleotides and amino acids are indicated. FIG. 22C and FIG. 22D depict LASV GPCD expression levels. Human 293T cells were transiently transfected with pCAGGS expression plasmids encoding wild-type (GP$_{WT}$) or codon deoptimized (GP$_{CD}$) LASV GP and were evaluated at 48 h p.t. for protein expression by immunofluorescence assay (FIG. 22C) and Western blot (FIG. 22D) using the LASV GP monoclonal antibody 24.9H. Representative images are illustrated. Scale bar=100 Empty (E) plasmid was included as negative control in the Western blot. GAPDH expression levels were used as loading controls.

DETAILED DESCRIPTION

Figure 1:
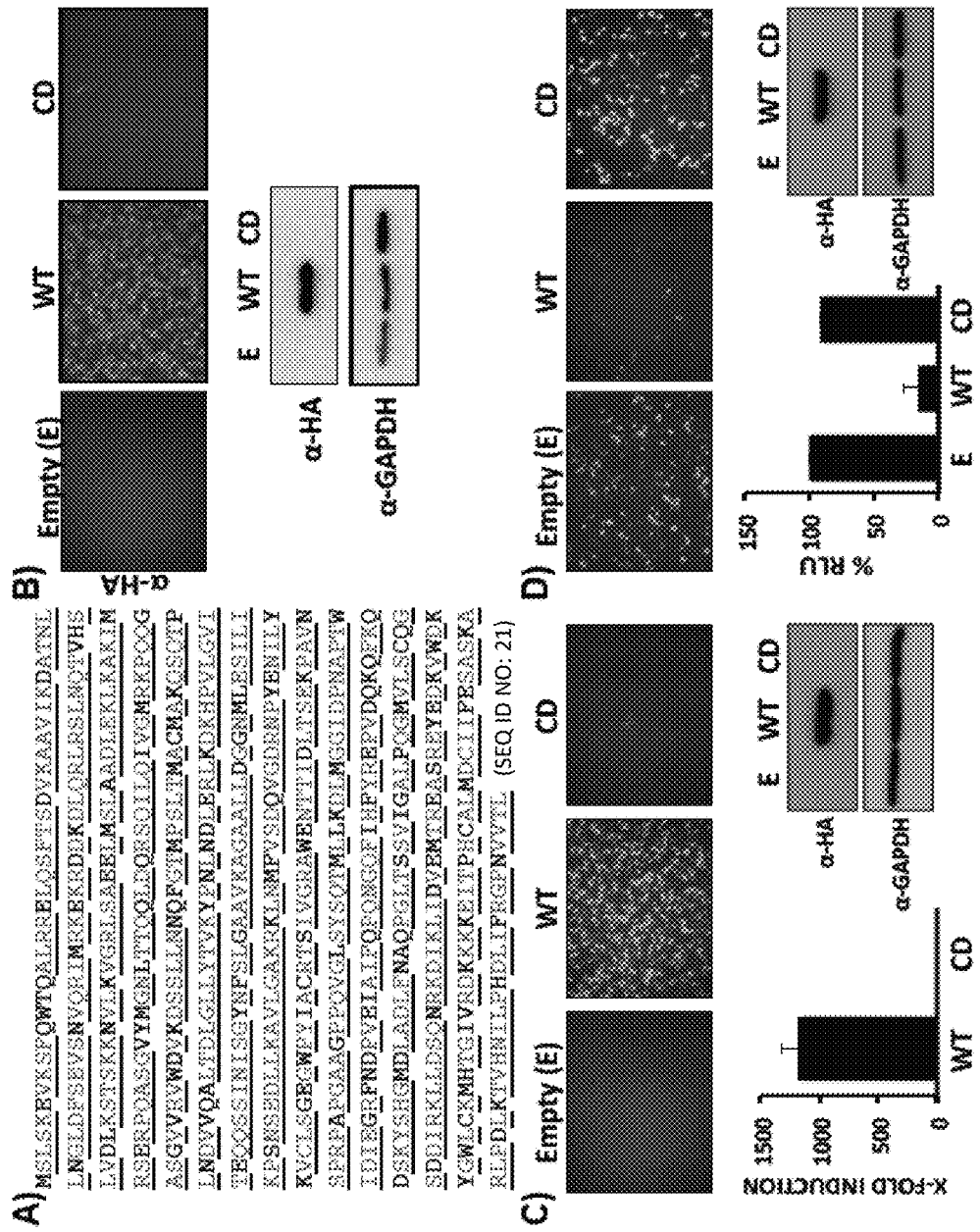
FIG. 1, comprising

The present invention relates to the discovery that codon deoptimized (CD) nucleic acids encoding arenavirus proteins are useful for the treatment and prevention of arenavirus infections and arenavirus related diseases and disorders. Thus, in certain aspects, the present invention relates to immunological compositions comprising a live attenuated vaccine (LAV), wherein the LAV is a CD arenavirus comprised of at least one CD polynucleotide of at least one protein selected from the group consisting of viral nucleoprotein (NP), glycoprotein precursor (GPC), or matrix (Z) protein, or combinations thereof.

The present invention also relates to methods for treating or preventing an arenavirus infection or an arenavirus related disease or disorder, using a composition of the invention. The invention also provides methods of inducing an immune response for preventing and treating an arenavirus infection or an arenavirus related disease or disorder. In one embodiment, the methods comprise administering an immunological composition comprising a LAV to a subject in need thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides immunological compositions and methods useful for the inhibition, prevention and treatment of arenavirus infection and arenavirus related diseases and disorders. In one embodiment, the immunological composition comprises a live-attenuated virus, wherein the virus is an arenavirus. While portions of the description of the invention refers to LCMV, the invention should be construed to encompass any other arenavirus in which codon deoptimization may be useful to generate a LAV. Non limiting examples of arenaviruses include hemorrhagic fever (HF)-causing Old World arenaviruses such as lymphocytic choriomeningitis virus (LCMV), Lassa virus (LASV), and Lujo virus (LUJV); and HF-causing New World arenaviruses such as Junin virus (JUNV), Machupo virus (MACV), Guanarito virus (GTOV), Sabia virus (SABV), Chapare virus (CHPV), Ocozocoautla de Espinosa virus (OCEV) and Whitewater Arroyo virus (WWAV).

As demonstrated herein, using a codon deoptimization (CD) strategy, the arenavirus genome is recoded using a suboptimal arrangement of codons that perfectly preserves the wild type (WT) amino acid sequence, thus allowing for the development of a safe and effective arenavirus LAV. The recombinant arenavirus is developed with open reading frames (ORF) where many of the amino acid are encoded by the less frequently used codon, which results in reduced protein expression and, therefore, viral attenuation. The compositions and methods of the present invention provide advantages over current approaches for the development of LAVs, which frequently rely on a very limited number of mutations that distinguish the LAV from its parental virulent strain, leading to a significant concern for reversion to virulence. In contrast, the CD strategy described herein introduces hundreds of silent mutations to create an LAV candidate which poses a huge barrier for a CD LAV to revert to the parental virulent form.

Redundancy in the genetic code results in many amino acids (amino acid) being encoded by more than one codon, and codon usage bias refers to differences in the frequency at which synonymous codons are used by an organism to incorporate the same amino acid residue into a protein (Gustafsson et al., 2004, Trends Biotechnol. 22:346-353; Kanaya et al., 2001, J. Mol. Evol. 53:290-298; Lavner and Kotlar, 2005, Gene 345:127-138; Urrutia and Hurst, 2001, Genetics 159:1191-1199; Yang and Nielsen, 2008, Mol. Biol. Evol. 25: 568-579). Optimization of codon composition is a frequently used strategy to improve expression of genes in heterologous systems (Gao et al., 2013, J. Vet. Sci. 14:441-447; Li et al., 2013, Virus Res. 175:120-127; Mani et al., 2011, Interdiscip. Sci. 3:36-42; Tenbusch et al., 2010, Vaccine 28:3273-3277; Barrett et al., 2006, Virus Genes 33:15-26), but all mammals exhibit essentially the same codon bias (Bains, 1993, DNA Seq. 3:277-282; Mouchiroud and Gautier, 1988, Mol. Biol. Evol. 5:192-194). Conversely, replacement of commonly used codons with nonpreferred codons (codon deoptimization) can dramatically decrease gene expression (Burns et al., 2006, J. Virology 80:3259-3272; Coleman et al., 2008, Science 320:1784-1787; Mueller et al., 2010, Nat. Biotechnol. 28:723-726; Yang et al., 2013, Proc. Natl. Acad. Sci. U.S.A. 110:9481-9486).

Protein expression of mammalian viruses is subjected to the codon usage bias of the cells they infect and thereby introduction of unfavorable host codons into a viral genome is predicted to adversely affect viral protein translation thus resulting in viral attenuation. Accordingly, data indicates that RNA viruses can be effectively attenuated by codon deoptimization of a single or a limited number of viral gene products (Burns et al., 2006, J. Virology 80:3259-3272; Coleman et al., 2008, Science 320:1784-1787; Mueller et al., 2010, Nat. Biotechnol. 28:723-726; Yang et al., 2013, Proc. Natl. Acad. Sci. U.S.A. 110:9481-9486).

The invention provides an immunological composition comprising a live-attenuated virus (LAV). In one embodiment, the LAV is a codon deoptimized (CD) arenavirus comprised of at least one CD polynucleotide encoding at least one protein selected from the group consisting of viral nucleoprotein (NP), glycoprotein precursor (GPC), matrix (Z) protein, and combinations thereof. The composition comprising one or more viruses of the invention not only are useful as a prophylactic therapeutic agent for immunoprotection, but is also useful as a therapeutic agent for treatment of an ongoing condition associated with an arenavirus related disease or disorder in a subject.

The present invention also provides methods of preventing, inhibiting, and treating an arenavirus related disease or disorder. In one embodiment, the methods of the invention induce immunity against the arenavirus by generating an immune response directed to the arenavirus. In one embodiment, the methods of the invention induce production of arenavirus-specific antibodies. In one embodiment, the methods of the invention prevent arenavirus related pathology. In one embodiment, the methods of the invention comprise administering an immunological composition comprising a live-attenuated virus (LAV), wherein the LAV is a codon deoptimized (CD) arenavirus comprised of at least one CD polynucleotide encoding at least one protein selected from the group consisting of viral nucleoprotein (NP), glycoprotein precursor (GPC), LCMV matrix (Z) protein, and combinations thereof, to a subject in need thereof. In one embodiment, the methods comprise administering an immunological composition to a subject in need thereof, thereby inducing immunity to an arenavirus.

Compositions

The present invention provides immunological compositions that when administered to a subject in need thereof, elicit an immune response directed against an arenavirus. In some embodiments, the composition includes polypeptides, nucleotides, vectors, or vaccines. Further, when the compositions are administered to a subject, they elicit an immune response that serves to protect the inoculated mammal against conditions associated with an arenavirus, such as hemorrhagic fever (HF). As exemplified herein, the composition can be obtained in large quantities for use as a vaccine.

In one embodiment, the present invention provides compositions that are useful as immunomodulatory agents, for example, in stimulating immune responses and in preventing arenavirus related pathology.

Live-attenuated viruses (LAV), wherein the LAV is a codon deoptimized (CD) arenavirus, can be used as immunostimulatory agents to induce the production of arenavirus antibodies and protect against arenavirus induced pathology. Therefore, in one embodiment, the composition of the invention comprises a live-attenuated virus (LAV), wherein the LAV is a codon deoptimized (CD) arenavirus comprised of at least one CD polynucleotide encoding at least one protein selected from the group consisting of viral nucleoprotein (NP), glycoprotein precursor (GPC), matrix (Z) protein, and combinations thereof.

In one embodiment, the composition comprises one or more CD polynucleotides encoding one or more of NP, GPC, or Z that is mutated from wild-type. Recoding arenavirus polypeptides into a suboptimal arrangement of codons while preserving the wild type (WT) amino acid sequence induces the production of arenavirus-specific antibodies, thereby resulting in the prevention of arenavirus-induced pathology. Thus, the CD-based strategy is useful for the development of an arenavirus live-attenuated vaccine (LAV).

The present invention should be construed to encompass any other arenavirus in which codon deoptimization may be useful to generate a LAV. In one embodiment, the arenavirus is lymphocytic choriomeningitis virus (LCMV). Additional non-limiting examples of arenaviruses include Lassa virus (LASV), Lujo virus (LUJV), Junin virus (JUNV), Machupo virus (MACV), Guanarito virus (GTOV), Sabia virus (SABV), Chapare virus (CHPV), Ocozocoautla de Espinosa virus (OCEV), and Whitewater Arroyo virus (WWAV).

In some embodiments, the invention provides a composition comprising one or more CD polynucleotides encoding NP. In one embodiment, the composition comprises one or more polynucleotides comprising a nucleic acid sequence selected from SEQ ID NOs: 2-11. In one embodiment, the composition comprises one or more polynucleotides comprising a nucleic acid sequence that is substantially homologous to one of SEQ ID NOs: 2-11. For example, in certain embodiments, the composition comprises one or more polynucleotides comprising a nucleic acid sequence that is at least 50% homologous, at least 60% homologous, at least 70% homologous, at least 80% homologous, at least 90% homologous, at least 95% homologous, at least 98% homologous, at least 99% homologous, or at least 99.5% homologous to one of SEQ ID NOs: 2-11.

In some embodiments, the composition comprises one or more CD polynucleotides encoding GPC. In one embodiment, the composition comprises a polynucleotide comprising a nucleic acid sequence selected from SEQ ID NOs: 13, 25, 28, 31, 34, 37, 40, 43, 46, and 49. In one embodiment, the composition comprises one or more polynucleotides comprising a nucleic acid sequence that is substantially homologous to one of SEQ ID NOs: 13, 25, 28, 31, 34, 37, 40, 43, 46, and 49. For example, in certain embodiments, the composition comprises one or more polynucleotides comprising a nucleic acid sequence that is at least 50% homologous, at least 60% homologous, at least 70% homologous, at least 80% homologous, at least 90% homologous, at least 95% homologous, at least 98% homologous, at least 99% homologous, or at least 99.5% homologous to one of SEQ ID NOs: 13, 25, 28, 31, 34, 37, 40, 43, 46, and 49.

In some embodiments, the composition comprises one or more CD polynucleotides encoding Z. In one embodiment, the composition comprises one or more polynucleotides comprising a nucleic acid sequence selected from SEQ ID NOs: 15-20. In one embodiment, the composition comprises one or more polynucleotides comprising a nucleic acid sequence that is substantially homologous to one of SEQ ID NOs: 15-20. For example, in certain embodiments, the composition comprises one or more polynucleotides comprising a nucleic acid sequence that is at least 50% homologous, at least 60% homologous, at least 70% homologous, at least 80% homologous, at least 90% homologous, at least 95% homologous, at least 98% homologous, at least 99% homologous, or at least 99.5% homologous to one of SEQ ID NOs: 15-20.

In one embodiment, the composition comprises one or more polynucleotides wherein the entire nucleic acid sequence encoding a peptide (e.g. NP, GPC, or Z) is codon deoptimized. In another embodiment, the composition comprises one or more polynucleotides wherein the polynucleotide is a chimeric construct. As used herein, the term "chimeric construct" refers to recombinant nucleic acid sequences which comprise at least one wild type nucleic acid coding sequence and at least one CD nucleic acid coding sequence. For example, in one embodiment, a polynucleotide encoding a peptide (e.g. NP, GPC, or Z) comprises a first region comprising a wild type nucleic acid sequence and a second region comprising a CD nucleic acid sequence. It is demonstrated herein that in certain instances compositions comprising a chimeric construct induce an immune response against an arenavirus, without production of an arenavirus related pathology.

In one embodiment, the nucleic acid sequence encoding the peptides is codon deoptimized at the N-terminal region of the nucleic acid sequence, and is wild type at the C-terminal region of the nucleic acid sequence. For example, in one embodiment, the composition comprises a polynucleotide encoding NP, where the nucleic acid sequence encoding NP is codon deoptimized at the N-terminal region of the nucleic acid sequence, and is wild type at the C-terminal region of the nucleic acid sequence. In one embodiment, the nucleic acid comprises a nucleic acid sequence selected from the group consisting of SEQ ID NO: 2 and SEQ ID NO: 3.

The polynucleotide can be RNA or DNA. In one embodiment, the composition comprises a DNA vaccine.

In one embodiment, the invention provides a polynucleotide encoding at least one polypeptide selected from SEQ ID NOs: 21-23, 26, 29, 32, 35, 38, 41, 44, 47, or 50. In one embodiment, the invention provides a composition comprising a nucleic acid sequence encoding the amino acid sequence of any one or more of SEQ ID NOs: 21-23, 26, 29, 32, 35, 38, 41, 44, 47, or 50.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid comprising a nucleotide sequence having substantial homology to a nucleotide sequence of an isolated nucleic acid encoding a polypeptide disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass a RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

In one embodiment, the composition of the invention comprises a polypeptide, or a fragment of a polypeptide, a homolog, a variant, a derivative or a salt of a polypeptide having the sequence of any one or more of SEQ ID NOs: 21-23, 26, 29, 32, 35, 38, 41, 44, 47, or 50.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, composition of the invention, comprising the polypeptide or combination of polypeptides of the present invention, is capable of generating an arenavirus-specific immune response. In another embodiment, the composition of the invention, comprising the polypeptide or combination of polypeptides of the present invention, is capable of generating arenavirus-specific antibodies.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

Codon Deoptimized (CD) Live Attenuated Virus (LAV)

The invention relates in part to the generation, selection and identification of codon deoptimized (CD) live attenuated viruses (LAV) that generate an arenavirus-specific immune response, and the use of such viruses in vaccine and pharmaceutical formulations.

As used herein, the term "codon deoptimization" refers to the selection of appropriate DNA nucleotides for use within a structural gene or fragment thereof such that the generated codons correspond to lower abundance tRNAs within a particular organism. As a non-limiting example, the nucleotide sequence encoding the polypeptide may be comprised, 100 percent, of species non-preferred codon sequences, while encoding a polypeptide with the same amino acid sequence as that produced by the native polypeptide coding sequence. Alternatively, the modified nucleotide sequence encoding the polypeptide may only be partially comprised of species preferred codon sequences with remaining codons retaining nucleotide sequences derived from the native polypeptide coding sequence. The modified nucleotide sequence may be fully or partially deoptimized for species codon usage provided that the protein encoded by the modified nucleotide sequence is produced at a level higher than the protein encoded by the corresponding naturally occurring or native gene. For example, the modified polynucleotide sequence may comprise from about 60% to about 100% codons deoptimized for species expression. As another example, modified polynucleotide sequence may comprise from 90% to 100% of codons deoptimized for species expression.

It will be appreciated that during codon deoptimization other modifications may be made to the polynucleotide sequence to enhance the efficiency of protein translation. Thus, for example one or more more-favored codons may be selected to delete existing ribosome attenuating sites or delete "restriction enzyme sites" to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

Any mutant virus or strain which has at least one CD nucleotide sequence can be selected and used in accordance with the invention. In one embodiment, naturally occurring mutants or variants, or spontaneous mutants can be selected that include at least one CD nucleotide sequence. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having at least one CD nucleotide sequence. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into an arenavirus such as LCMV, Lassa virus (LASV), Lujo virus (LUJV), Junin virus (JUNV), Machupo virus (MACV), Guanarito virus (GTOV), Sabia virus (SABV), Chapare virus (CHPV), Ocozocoautla de Espinosa virus (OCEV), and Whitewater Arroyo virus (WWAV) using "reverse genetics" approaches. In this way, natural or other mutations which confer the attenuated phenotype can be engineered into vaccine strains. For example, deletions, insertions or substitutions of the coding region of the gene responsible for the NP, GPC or Z protein can be engineered. Deletions, substitutions or insertions in the non-coding region of the gene responsible for the NP, GPC or Z protein are also contemplated. To this end, mutations in the signals responsible for the transcription, replication, polyadenylation and/or packaging of the gene responsible NP, GPC or Z protein can be engineered.

In certain instances, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. In some instances, a more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain.

In an alternate embodiment, a combination of reverse genetics techniques and reassortant techniques can be used to engineer attenuated viruses having the desired epitopes in arenaviruses. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

The attenuated virus of the present invention can itself be used as the active ingredient in vaccine or pharmaceutical formulations. In certain embodiments, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens.

For example, in one embodiment, the immunological composition of the invention comprises a CD attenuated virus, engineered to express one or more epitopes or antigens of a given pathogen. For example, the attenuated virus can be engineered to express neutralizing epitopes of other preselected strains. Alternatively, epitopes of other viruses can be built into the attenuated mutant virus. Alternatively, epitopes of non-viral infectious pathogens (e.g., parasites, bacteria, fungi) can be engineered into the virus.

In one embodiment, the attenuated viruses selected for use in the invention is capable of inducing a robust anti-arenavirus response in the host—a feature which contributes to the generation of a strong immune response when used as a vaccine, and which has other biological consequences that make the viruses useful as pharmaceutical agents for the prevention and/or treatment of other viral infections, or other diseases.

The attenuated viruses, which induce an arenavirus-specific immune response in hosts, may also be used in pharmaceutical formulations for the prophylaxis or treatment of other viral infections, or arenavirus related diseases, such as HF. In this regard, the tropism of the attenuated virus can be altered to target the virus to a desired target organ, tissue or cells in vivo or ex vivo. Using this approach, the arenavirus-specific immune response can be induced locally, at the target site, thus avoiding or minimizing the side effects of systemic treatments. To this end, the attenuated virus can be engineered to express a ligand specific for a receptor of the target organ, tissue or cells.

Vaccine

For an immunological composition to be useful as a vaccine, the antigenic composition must induce an immune response to the antigen in a cell, tissue or mammal (e.g., a human). Preferably, the vaccine induces a protective immune response in the mammal. As used herein, an "immunological composition" may comprise, by way of examples, a codon deoptimized (CD) live-attenuated virus (LAV), a CD arenavirus, an antigen (e.g., a polypeptide), a nucleic acid encoding an antigen (e.g., an antigen expression vector), or a cell expressing or presenting an antigen or cellular component. In particular embodiments the immunological composition comprises or encodes all or part of any polypeptide antigen described herein, or an immunologically functional equivalent thereof. In other embodiments, the immunological composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces anti-arenavirus immunity or suppresses an arenavirus upon inoculation into an animal.

The invention encompasses vaccine formulations comprising live attenuated virus (LAV), wherein the LAV is a codon deoptimized (CD) arenavirus. In one embodiment, the virus is a codon deoptimized (CD) arenavirus comprised of at least one CD polynucleotide encoding at least one protein selected from the group consisting of viral nucleoprotein (NP), glycoprotein precursor (GPC), matrix (Z) protein, and combinations thereof, and a suitable excipient. The virus used in the vaccine formulation may be selected from naturally occurring mutants or variants, mutagenized viruses or genetically engineered viruses. Attenuated strains of a CD arenavirus can also be generated via reassortment techniques, or by using a combination of the reverse genetics approach and reassortment techniques. Naturally occurring variants include viruses isolated from nature as well as spontaneous occurring variants generated during virus propagation, having at least one CD nucleotide sequence. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

In one embodiment, the present invention comprises a method of generating a LAV arenavirus, comprising contacting a host cell with a polynucleotide comprising one or more CD nucleic acid sequences described elsewhere herein.

Propagation of the virus in culture is known to persons in the art. Briefly, the virus is grown in the media compositions in which the host cell is commonly cultured. Suitable host cells for the replication of an arenavirus include, e.g., Vero cells, BHK cells, MDCK cells, 293 cells COS cells, and CEK cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, 5.sup.th ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of an arenavirus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Many methods may be used to introduce the vaccine formulations described above, these include but are not limited to introduction intranasally, intratracheally, orally, intradermally, intramuscularly, intraperitoneally, intravenously, and subcutaneously. It may be preferable to introduce the virus vaccine formulation via the natural route of infection of the pathogen for which the vaccine is designed, or via the natural route of infection of the parental attenuated virus. Where a live arenavirus vaccine preparation is used, it may be preferable to introduce the formulation via the natural route of infection for arenavirus virus.

A vaccine of the present invention, comprising a CD attenuated arenavirus, could be administered once. Alternatively, a vaccine of the present invention, comprising a CD attenuated arenavirus, could be administered twice or three or more times with a suitable interval between doses. Alternatively, a vaccine of the present invention, comprising a CD attenuated arenavirus, could be administered as often as needed to an animal, preferably a mammal, and more preferably a human being.

Methods

The invention provides a method for treating or preventing arenavirus infection or an arenavirus related disease or disorder. In one embodiment, the method comprises administering an immunological composition comprising a live-attenuated virus (LAV), wherein the LAV is a codon deoptimized (CD) arenavirus. In one embodiment, the composition comprises a CD LAV arenavirus comprised of at least one CD polynucleotide encoding at least one protein selected from the group consisting of viral nucleoprotein (NP), glycoprotein precursor (GPC), LCMV matrix (Z) protein, and combinations thereof, to a subject in need thereof. Non-limiting examples of arenavirus related diseases or disorders include lymphocytic choriomeningitis, hemorrhagic fever (HF), Lassa hemorrhagic fever, Argentine hemorrhagic fever (AHF), Bolivian hemorrhagic fever, Brazilian hemorrhagic fever, Chapare hemorrhagic fever, Lujo hemorrhagic fever, and Venezuelan hemorrhagic fever.

In one embodiment, the arenavirus infection is associated with an arenavirus related disease or disorder. Examples include, but are not limited to, hemorrhagic fever (HF) causing Lassa virus (LASV, Lassa hemorrhagic fever), Lujo virus (LUJV, Lujo hemorrhagic fever), Junin virus (JUNV, Argentine hemorrhagic fever), Machupo virus (MACV, Bolivian hemorrhagic fever), Guanarito virus (GTOV, Venezuelan hemorrhagic fever), Sabia virus (SABV, Brazilian hemorrhagic fever), Chapare virus (CHPV, Chapare hemorrhagic fever) Ocozocoautla de Espinosa virus (OCEV) and Whitewater Arroyo virus (WWAV).

The therapeutic compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The composition may be combined with an adjuvant. An adjuvant refers to a compound that enhances the immune response when administered together (or successively) with the immunological composition. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering an immunological composition of the invention directly to a subject in need thereof. Administration of the composition can comprise, for example, intramuscular, intravenous, peritoneal, subcutaneous, intradermal, as well as topical administration.

Furthermore, the actual dose and schedule can vary depending on whether the compositions are administered in combination with other pharmaceutical compositions, or depending on inter-individual differences in pharmacokinetics, drug disposition, and metabolism. One skilled in the art can easily make any necessary adjustments in accordance with the exigencies of the particular situation.

Pharmaceutical Compositions

The present invention envisions treating or preventing a disease or condition associated with an arenavirus in a mammal by the administration of a therapeutic composition of the invention to a mammal in need thereof. Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention encompasses pharmaceutical compositions comprising a codon deoptimized (CD) arenavirus to be used as anti-viral agents or as agents against arenavirus related diseases and disorders. The pharmaceutical compositions have utility as an anti-viral prophylactic and may be administered to an individual at risk of getting infected or is expected to be exposed to a virus. For example, people traveling to parts of the world where a certain arenavirus is prevalent can be administered a pharmaceutical composition of the invention.

The codon deoptimized (CD) arenaviruses of the invention may be engineered using the methods described herein to express proteins or peptides which would target the viruses to a particular site. In one embodiment, where the site to be targeted expresses a receptor to a growth factor, e.g., VEGF, EGF, or PDGF, the CD arenavirus may be engineered to express the appropriate growth factor or portion(s) thereof. Thus, in accordance with the invention, the CD arenaviruses may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment of a particular disease or disorder will depend on the nature of the disease or disorder, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Development of Live-Attenuated Arenavirus Vaccines Based on Codon Deoptimization The results described herein demonstrate the recoding of the LCMV nucleoprotein (NP) open reading frame (ORF) in a way that preserved the wild-type (WT) amino acid sequences but created a suboptimal utilization of codons. These mutant NPs were used to generate a battery of recombinant LCMV containing NP sequences with different degrees of codon-deoptimization (rLCMV/NPcd). It was found that the rLCMV/NPcd were more attenuated in human A549 cells than in rodent BHK-21 or Vero cell lines. Importantly, intracranial inoculation of mice with two different rLCMV/NPcd led to no detectable signs of morbidity and conferred protection against a subsequent lethal challenge with rLCMV/WT, demonstrating the possibility of using a codon-deoptimized strategy for the rational design of safe, immunogenic and protective live-attenuated vaccines (LAV) for the treatment of arenavirus infections in humans, including HF-causing members in the family.

Codon Deoptimization Affects LCMV NP Expression Levels

For initial studies, NP was selected to examine the potential of CD rLCMV as LAV because its multifunctional properties. NP is the most abundant viral protein in LCMV-infected cells and virions (Buchmeier et al., 2007, Ch. 50, pgs. 1791-1827 in Fields Virology Vol. II, Lippincott Williams & Wilkins) and besides its critical role in virus replication and transcription, NP counteracts the host type I interferon (IFN-I) response in infected cells by preventing activation and nuclear translocation of transcription factors IRF3 and NF-κB, thus interfering with the induction of IFN-I and interferon-stimulated genes (ISGs) (Martinez-Sobrido et al., 2009, J. Virology 83:11330-11340; Martinez Sobrido et al., 2007, J. Virology 81:12696-12703; Martinez-Sobrido et al., 2006, J. Virology 80:9192-9199; Rodrigo et al., 2012, J. Virology 86:8185-8197; Pythoud et al., 2012, J. Virology 86:7728-7738).

A NP ORF was generated where each codon was replaced with the least abundant in mammalian cells, without affecting the WT amino acid sequence (FIG. 1A). The resulting CD NP was synthesized de novo and subcloned into the pCAGGS expression plasmid containing an HA-tag at the C-terminal end of NP53-57. Expression levels of CD NP were affected in HEK293T as determined by, both, immunofluorescence (IFA) and Western blot (WB) assays (FIG. 1B) using previously known methods (Ortiz-Riano et al., 2011, J. Virology 85:13038-13048; Ortiz-Riano et al., 2012, J. Virology 86:3307-3317; Ortiz-Riano et al., 2012, Viruses 4:2137-2161).

Next, the activity of CD NP in (i) viral replication and transcription was evaluated using a minigenome (MG) assay (FIG. 1C) (Ortiz-Riano et al., 2013, J. Gen. Virology 94:1175-1188; Cheng et al., 2013, J. Vis. Exp. doi:10.3791/50662), and, (ii) inhibition of IFNβ promoter activation (FIG. 1D), using previously known methods (Martinez-Sobrido et al., 2009, J. Virology 83:11330-11340; Martinez Sobrido et al., 2007, J. Virology 81:12696-12703; Martinez-Sobrido et al., 2006, J. Virology 80:9192-9199; Rodrigo et al., 2012, J. Virology 86:8185-8197; Pythoud et al., 2012, J. Virology 86:7728-7738). Using the same amounts of plasmids encoding WT and CD NPs, the reduced protein expression observed with CD NP correlated with a dramatic decreased on NP activity in these two cell-based assays.

Generation and Characterization of CD LCMV NP Chimeric Constructs

Figure 2:
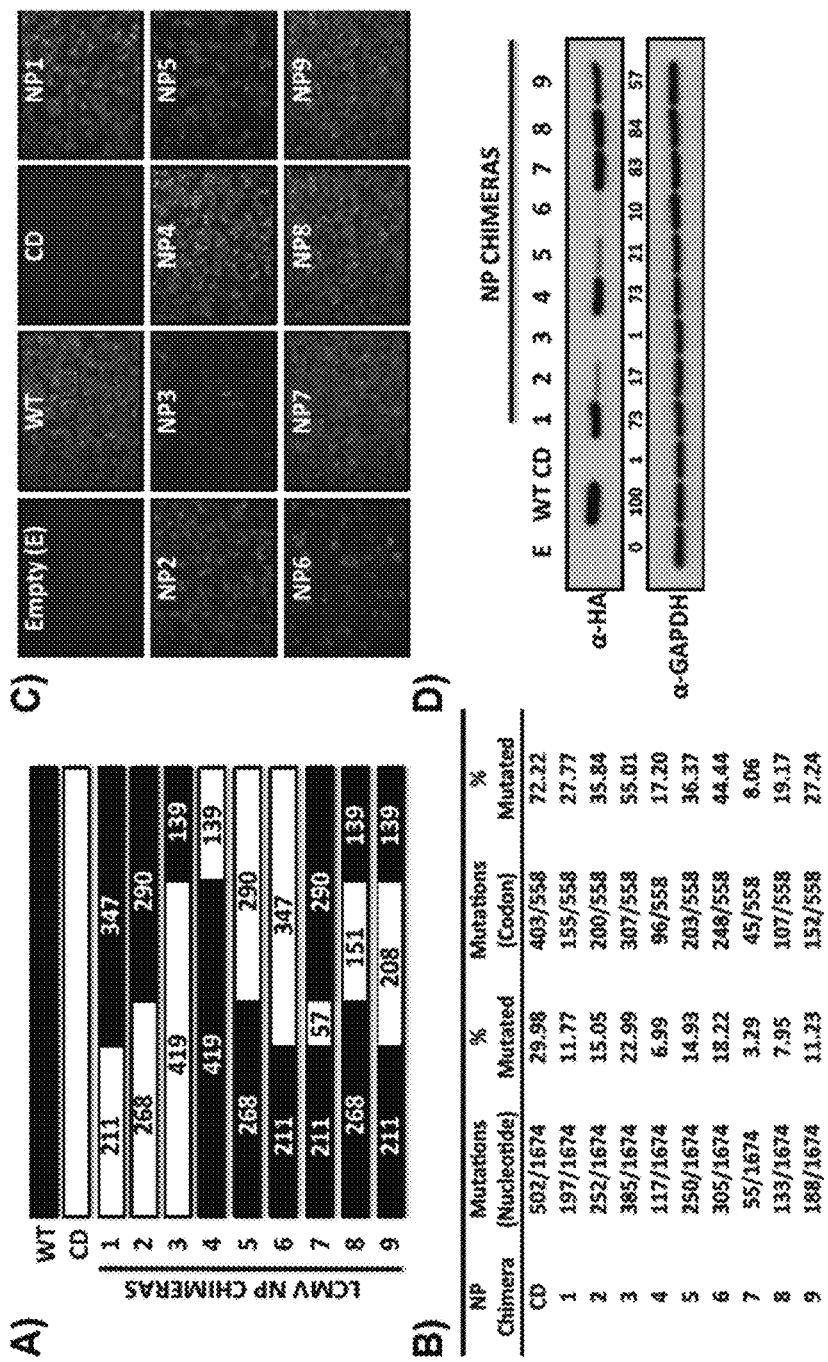
FIG. 2, comprising

In some instances, successful generation of rLCMV with CD genes would require a balance between the degree of codon deoptimization and levels of protein expression and function of genes with CD ORFs. To examine this issue, a collection of chimeric constructs between WT and CD NP was generated (FIG. 2A and FIG. 2B). Expression levels of these chimeric constructs correlated with the degree of codon deoptimization as determined by IFA and WB (FIG. 2C and FIG. 2D).

Functional Characterization of CD LCMV NP Chimeric Constructs

Figure 3:
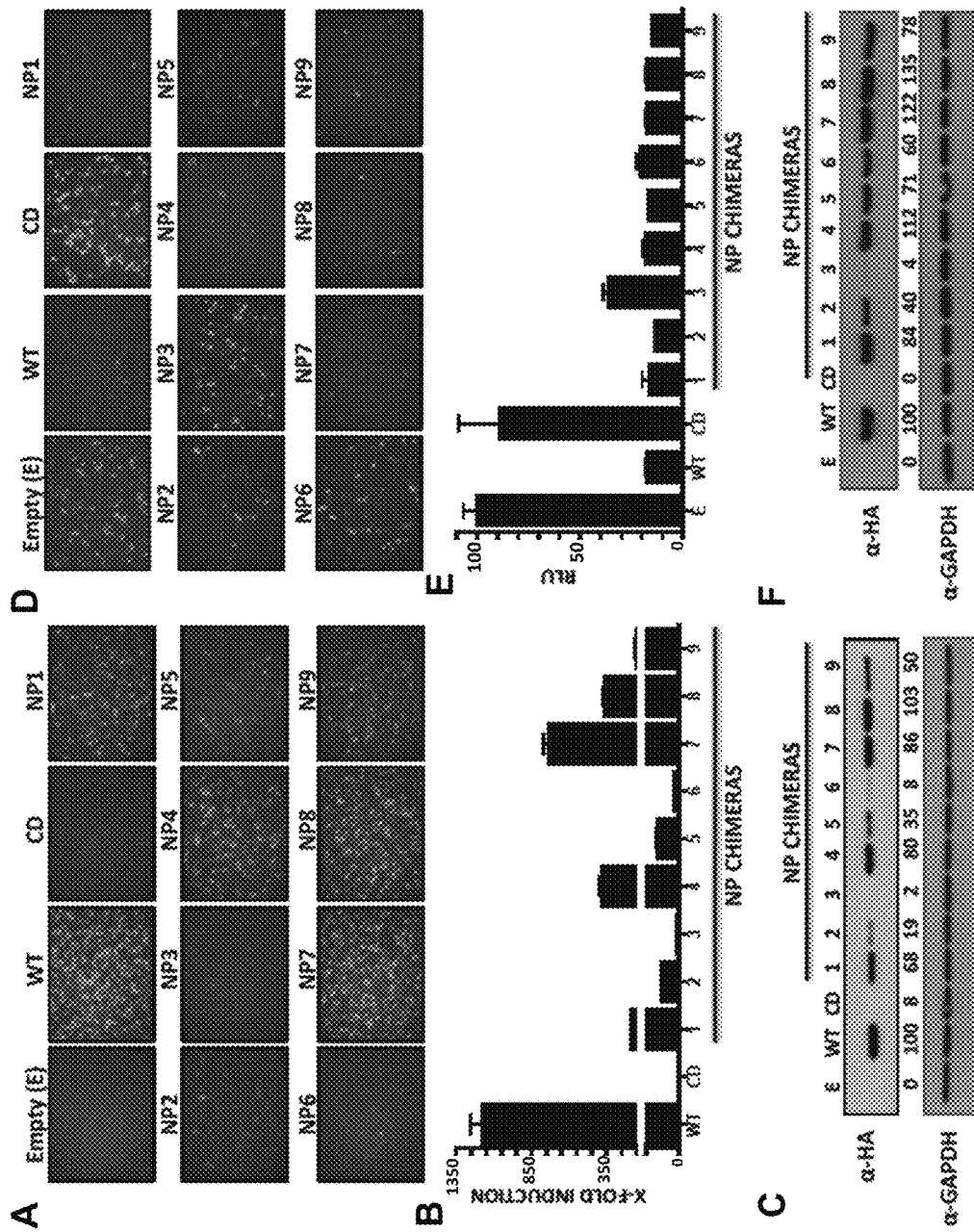
FIG. 3, comprising

The effect of CD NP chimeras in viral replication and transcription was evaluated using a MG assay (FIG. 3A), as well as in inhibition of IFNβ promoter activation upon SeV infection (FIG. 3B). Viral replication of the MG, as determined by GFP expression (FIG. 3A) and Firefly luciferase activity (FIG. 3B), correlated with CD NP expression levels (FIG. 3C). Similarly, the magnitude of CD NP-mediated inhibition of IFNβ promoter activation upon SeV infection as measured by GFP (Figure D) or Firefly luciferase (FIG. 3E) correlated with protein expression levels (FIG. 3F).

Generation of Recombinant Viruses Expressing CD LCMV NP Constructs (rLCMV/NPcd)

Figure 4:
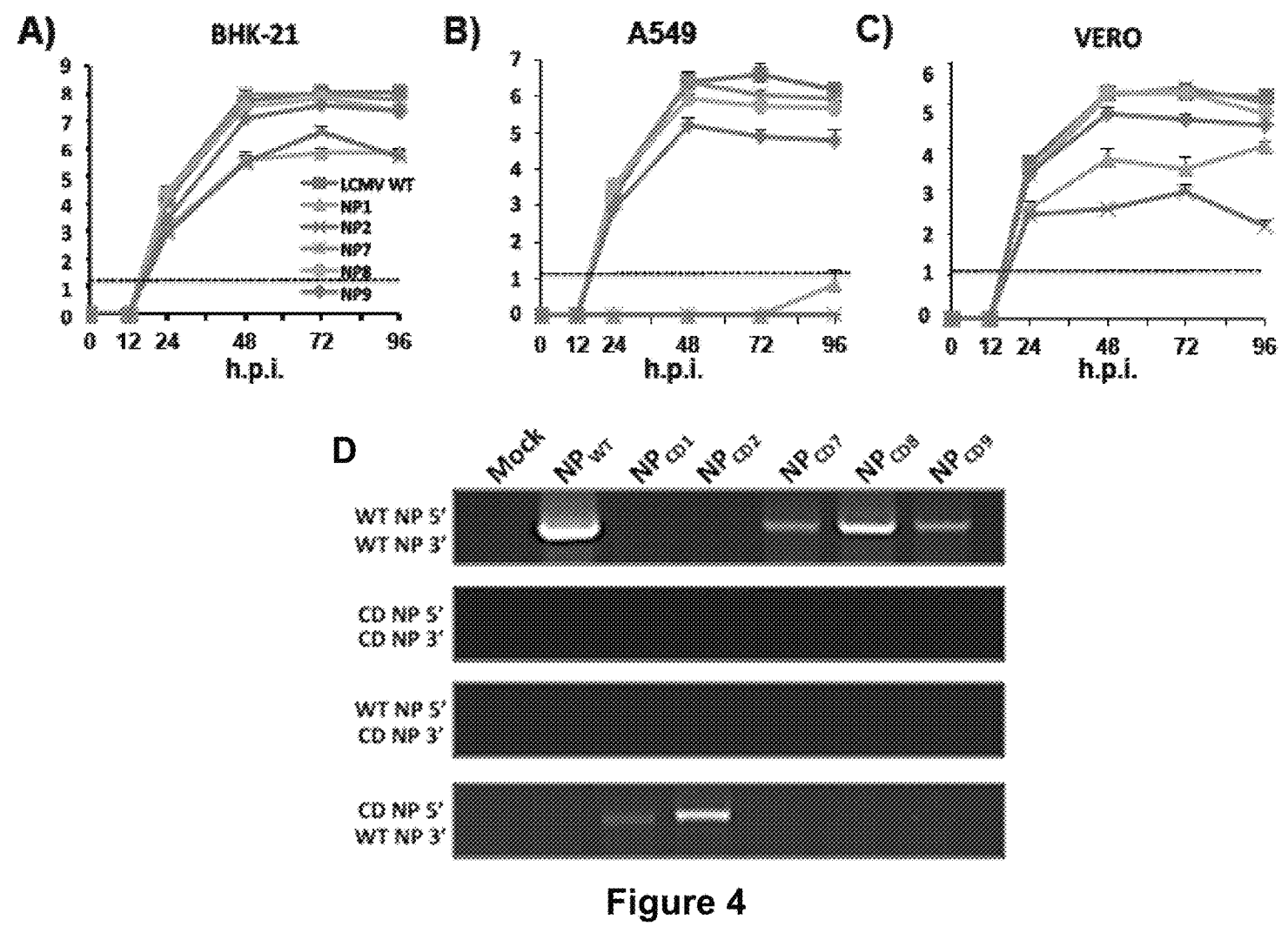

Reverse genetics techniques were used to rescue rLCMV containing each of the different CD NP constructs. rLCMVNP$_{CD}$ by RT-PCR was confirmed by RT-PCR using BHK-21 cells (FIG. 4D). Five out of 9 rLCMV/NPcd (NP1, NP2, NP7, NP8, and NP9) were successfully generated. The identity of these viruses was confirmed by RT-PCR using RNA extracted from infected Vero cells, and sequencing of the amplified PCR products (FIG. 5). Next, the viral growth kinetics in rodent BHK-21 (FIG. 4A), human A549 (FIG. 4B), and vaccine FDA-approved Vero (FIG. 4C) cells were evaluated. Viral attenuation was more pronounced in A549 cells than in Vero or BHK-21 cells. Although not wishing to be bound by any particular theory, this result could reflect differences in species codon usage, or in tRNA availability among cell lines, or a higher decreased in fitness in IFN-I competent A549 cells compared to IFN-I-deficient BHK-21 and Vero cells.

Virulence and Protective Efficacy of rLCMV/NPcd In Vivo

The assessment of the virulence and ability to induce a protective immune response in vivo represents a first and necessary step to evaluate the potential of rLCMV/NPcd as LAV. To this end, adult (6 weeks) immune competent WT B6 mice were infected intracraneally (i.c.) with $10^3$ plaque-forming units (PFU) of the indicated virus (Table 1). All mice infected with rLCMV/WT and rLCMV/NP7 developed the expected fatal LCM within 8 days and succumbed to viral infection. In contrast, all mice infected with rLCMV/NP1 and NP2 survived and remained free of clinical symptoms throughout the duration (12 days) of the experiment.

TABLE 1

Safety of rLCMV/NPcd
% Survival (N = 8)

| | Days p.i. (i.c., $10^3$ PFU) | | | |
|---|---|---|---|---|
| | 6 | 7 | 8 | 12 |
| rLCMV/NP1 | 100 | 100 | 100 | 100 |
| rLCMV/NP2 | 100 | 100 | 100 | 100 |
| rLCMV/NP7 | 100 | 25 | 0 | — |
| rLCMV WT | 100 | 37.5 | 0 | — |

To further explore the efficacy of CD rLCMV as LAV, rLCMV/NP1 was used in a standard LCMV immunization protocol (i.p., administration of $10^5$ PFU) of B6 mice. Four weeks later immunized mice were subjected to a lethal challenge (i.c., $10^3$ PFU) with rLCMV/WT (Table 2). All (100%) mice immunized with either WT or rLCMV/NP1 survived and remained free of clinical symptoms throughout the duration (12 days) of the experiment. As expected all mock-immunized (PBS) mice developed severe clinical symptoms and died within eight days of the i.c. challenge with rLCMV/WT. These results demonstrate the feasibility of using CD rLCMV for the development of safe and effective LAV candidates.

TABLE 2

Protective efficacy of rLCMV/NPcd
% Survival (N = 8)

| | Days p.i. with rLCMV WT (i.c., $10^3$ PFU) | | | |
|---|---|---|---|---|
| | 6 | 7 | 8 | 12 |
| rLCMV/NP1* | 100 | 100 | 100 | 100 |
| rLCMV WT* | 100 | 100 | 100 | 100 |
| Mock | 100 | 25 | 0 | — |

*i.p., $10^5$ PFU

Generation and Characterization of rLCMV/GPCcd and rLCMV/Zcd

Design and De Novo Synthesis of CD LCMV GPC and Z ORFs

The GPC and Z ORFs are deoptimized attending to the mammalian codon usage using the same strategy described elsewhere herein. Multiple silent mutations are introduced to replace the current sequences by underrepresented codons without affecting GPC and Z amino acid compositions. These CD ORFs are synthesized flanked with appropriated restriction sites for subcloning into the mammalian expression plasmid pCAGGS. To facilitate detection of CD LCMV GPC and Z proteins, the corresponding ORFs contain an HA-tag at the C-terminal end.

Characterization of CD LCMV GPC and Z

To determine the effect of codon deoptimization on LCMV GPC and Z protein expression, HEK293T cells are transfected with CD GP and Z pCAGGS expression plasmids and assessed by IFA and WB assays using an anti-HA pAb. Empty and LCMV GPC and Z WT pCAGGS expression plasmids are included as negative and positive controls, respectively. The amino acid sequence of CD LCMV GPC and Z remains unaltered and it is hypothesized that they will retain WT protein functions. To confirm this hypothesis, the following cell-based functional assays are conducted:

A) Rescue of a GP-deficient, single-cycle infectious rLCMV (rLCMVAGPC/GFP): A rLCMV in which the GPC ORF was replaced by GFP (rLCMVAGPC/GFP) has been generated using previously described methods (Rodrigo et al., 2011, J. Virology 85:1684-1695). Genetic complementation with a GPC-expressing plasmid permitted the generation of a single-cycle infectious rLCMVAGPC/GFP whose cell entry is mediated by the GPC used for pseudotyping (Rodrigo et al., 2011, J. Virology 85:1684-1695). The rLCMVAGPC/GFP is pseudotyped very efficiently with various arenavirus GPCs, including those of LASV and JUNV (Rodrigo et al., 2011, J. Virology 85:1684-1695).

This assay is used to confirm that CD GPC, though expressed at much lower levels, retains WT function. The amount of pCAGGS plasmid expressing CD GPC needed in order to achieve the lowest expression levels of WT GPC expression required for successful complementation of rLCMVAGPC/GFP is determined. The identified amounts of pCAGGS expressing either WT or CD GPC are used to transfect HEK293T cells and 24 h later infect them with rLCMVAGPC/GFP pseudotyped with LCMV GPC. Functionality of CD GPC is assessed based on their ability to promote growth of the single-cycle infectious rLCMVAGPC/GFP (Rodrigo et al., 2011, J. Virology 85:1684-1695).

B) Inhibition of MG replication and transcription: The generation and use of an LCMV MG assay where expression of reporter genes of interest are placed under the control or viral cis-acting promoter sequences has been previously reported (Ortiz-Riano et al., 2013, J. Gen. Virology 94:1175-1188; Cheng et al., 2013, J. Vis. Exp. doi:10.3791/50662). The MG plasmid together with plasmids expressing L and NP, the only viral proteins required to form a functional virus polymerase complex, are transfected into cells and the activity of the reporter genes is used as a measure of the levels of RNA synthesis by the reconstituted arenavirus polymerase complex. Arenavirus Z protein has been shown to exhibit a dose-dependent inhibitory effect on RNA replication and transcription by the arenavirus polymerase in the cell-based MG assay (Cornu and de la Torre, 2001, J. Virology 75:9415-9426; Cornu et al., 2004, J. Virology 78:2979-2983).

The function of CD Z is evaluated based on its ability to inhibit, in a dose-dependent manner, viral RNA replication and gene transcription using the MG rescue system using previously described methods (Ortiz-Riano et al., 2013, J. Gen. Virology 94:1175-1188; Cheng et al., 2013, J. Vis. Exp. doi:10.3791/50662). For this study, the amount of plasmid expressing CD Z that is required to achieve Z expression levels similar to WT Z that cause 50% inhibition of the MG activity is identified. These amounts of WT and CD Z expression plasmids are used to transfect HEK293T cells, together with plasmids encoding LCMV NP, L and MG. After 36 h, the levels of MG activity are assessed by determining GFP and Gaussia luciferase reporter gene expressions using previously described methods (Ortiz-Riano et al., 2013, J. Gen. Virology 94:1175-1188; Cheng et al., 2013, J. Vis. Exp. doi:10.3791/50662).

Generation and Characterization of CD LCMV GPC and Z Chimeric Constructs

In the event that the entire CD GPC and Z proteins are expressed to levels that permit successfully rescuing the corresponding rLCMV, chimeras are generated between WT and CD GPC and Z proteins that will have different degrees of codon deoptimization using methods described elsewhere herein.

An initial battery of 9 chimeric GPC and Z proteins containing N-terminal, C-terminal, or internal CD sequences is generated. Protein expression is assessed by IFA and WB assays using an anti-HA pAb as previously described (Ortiz-Riano et al., 2011, J. Virology 85:13038-13048; Ortiz-Riano et al., 2012, J. Virology 86:3307-3317). These chimeric constructs are evaluated in the previously cell-based functional assays described elsewhere herein. Empty, WT and fully CD GPC and Z plasmids are included as controls.

Generation and Characterization in Cultured Cells of rLCMV/GPCcd and rLCMV/Zed

Rescue of rLCMV/GPCcd and rLCMV/Zcd

Reverse genetics techniques are used to rescue CD GPC and CD Z rLCMV using previously described methods (Ortiz-Riano et al., 2013, J. Gen. Virology 94:1175-1188; Cheng et al., 2013, J. Vis. Exp. doi:10.3791/50662). Vero cells are co-transfected with the expression plasmids supporting viral replication and transcription (NP and L) together with the two plasmids encoding the viral L and S RNAs (Ortiz-Riano et al., 2013, J. Gen. Virology 94:1175-1188; Cheng et al., 2013, J. Vis. Exp. doi:10.3791/50662). Supernatants from transfected cells are passaged in fresh Vero cells to amplify the rescued rLCM viruses (Ortiz-Riano et al., 2013, J. Gen. Virology 94:1175-1188; Cheng et al., 2013, J. Vis. Exp. doi:10.3791/50662). Presence of the viruses is evaluated by IFA. Viruses are then plaque-purified and scaled up to generate high-titer virus stocks. The identity of the recombinant viruses is confirmed by RT-PCR and sequencing.

In Vitro Characterization of rLCMV/GPCcd and rLCMV/Zcd

The rLCMV expressing CD GPC and Z proteins are characterized by evaluating their growth kinetics, viral RNA synthesis and protein expression levels in Vero and A549 cells using previously described methods (Ortiz-Riano et al., 2012, Viruses 4:2137-2161; Ortiz-Riano et al., 2014, J. Virology 88:878-889).

Growth kinetics: To evaluate replication properties of WT and CD rLCM viruses, Vero and A549 cells are infected at low (0.01) and high (3) MOI. At different times post-infection, tissue culture supernatants are harvested and assessed for infectious virus by immunofocus assay.

Kinetics of RNA synthesis and protein expression levels: The effect of codon deoptimization on the kinetics of viral RNA synthesis is assessed by Northern blot using DNA probes that hybridizes to both the genome S RNA (~3.5 kb, replication) and the NP mRNA (~1.5 kb, transcription) (Ortiz-Riano et al., 2014, J. Virology 88:878-889). To that end, Vero and A549 cells are infected at low (0.01) and high (3) MOI with WT or CD rLCM viruses and, at different times post-infection, cell extracts are harvested to extract RNA for Northern blot using previously described methods (Ortiz-Riano et al., 2014, J. Virology 88:878-889).

To evaluate the effect of codon deoptimization of rLCM viruses on protein synthesis, total proteins from Vero and A549 cells infected with WT or CD rLCM viruses at different times post-infection and at low (0.01) and high (3) MOI are separated by SDS-PAGE and analyzed for protein expression by WB using NP (1.1.3) and GP (83.6) MAbs and an anti-Z pAb using previously described methods (Ortiz-Riano et al., 2011, J. Virology 85:13038-13048; Ortiz-Riano et al., 2012, J. Virology 86:3307-3317).

Characterization of Selected rLCMV/GPCcd and rLCMV/Zed In Vivo

Live attenuated virus vaccines depend on a limited, yet safe, degree of replication within the host to stimulate the immune system. Mouse experiments are performed to evaluate the virulence of CD rLCMV, as well as their ability to induce a protective response against the challenge posed by LCMV induced fatal LCM.

Ability of rLCMV/GPCcd and rLCMV/Zcd to Induce Fatal LCM

Adult (6 weeks) immune competent WT B6 mice inoculated i.c. with rLCMV/WT develop a fatal lymphocytic choriomeningitis (LCM) within 6-8 days p.i. (Oldstone, 2002, Curr. Top. Microbiol. Immunol. V-XII). The i.c. route of inoculation facilitates LCMV replication and accumulation of high viral antigen load within the choroid plexus and meninges, as well as viral entry into the blood stream and replication to sufficient degree in the periphery to prime an effective virus-specific T-cell response (Buchmeier et al., 2007, Ch. 50, pgs. 1791-1827 in Fields Virology Vol. II, Lippincott Williams & Wilkins). The ensuring robust immune cellular response to viral antigens present at high levels in the choroids plexus and meninges is responsible for the fatal LCM (Buchmeier et al., 2007, Ch. 50, pgs. 1791-1827 in Fields Virology Vol. II, Lippincott Williams & Wilkins). This model provides a straightforward approach to assess virulence of the different CD rLCMV by comparing the survival rate between mice inoculated i.c. with different doses of rLCMV/WT, rLCMV/GPCcd and rLCMV/Zcd.

Differences in survival between rLCMV/WT and CD rLCMV are determined using the Meier Log-Rank test, with N=10 mice/group to have a 90% power of detecting a difference of 20%, or higher, significance level >5%, based on the expected mortality of 100% mice infected with rLCMV/WT. The development of clinical symptoms and death is correlated with virus multiplication. Levels of viral load in meninges and sera are determined at days 1, 3, 5, and 6 p.i. Viral load within meninges and choroid plexus is assessed by examining NP levels in brain sections by IFA, whereas virus titers in brain and sera is determined by plaque assay. It is hypothesized that rLCMV/GPCcd and rLCMV/Zcd are attenuated in their ability to replicate in mice, thus resulting in the absence, reduced, or delayed, mortality.

Ability of rLCMV(Cl-13)/GPCcd and rLCMV(Cl-13)/Zcd to Persist in an Immunocompetent Adult Mouse Following IV Inoculation with a High Viral Dose Infection of WT B6 mice with a high dose (>$10^6$ PFU) of rLCMV C1-13 causes impaired dendritic cell (DC) and T-cell functions that results in a transient generalized immunosuppression and establishment of a persistent infection, hence the phenotype of C1-13 is termed CTL-/Pi+, where the parameters of virus multiplication, IFN-I response and composition and magnitude of the anti-LCMV T cell responses over time are well established (Oldstone, 2002, Curr. Top. Microbiol. Immunol. V-XII). Virus clearance takes place between days 60-100 p.i. and correlates with the recovery of normal host immune responses. This model provides an opportunity to determine whether codon deoptimization of viral proteins is important for the establishment of viral persistence.

rCL-13/WT and rCL-13 are compared with CD NP, GP, and Z with respect to: 1) viral loads, and 2) virus effect on innate and adaptive immune responses. Specifically, viral effects are assessed on cytokine production by the different populations of DCs and generation of virus-specific CD4+ and CD8+ T cell responses. Virus multiplication are determined in serum, spleen and liver by measuring levels of viral RNA and infectious LCMV by RT-qPCR and plaque assays, respectively. To assess the IFN-I response, levels of IFNβ mRNA in spleen are determined by RT-qPCR, and IFN-I activity in serum using bioassays and ELISA.

In the event that rCl-13 CD viruses are impaired in their ability to replicate in WT B6 mice, which together with an enhanced host IFN-I response may prevent the establishment of persistence, IFNAR−/− mice are incorporated into the experimental design.

Assessment of the Ability of rLCMV/GPCcd and rLCMV/Zcd to Induce an Immune Protective Response Against LCMV Induced Lethal LCM Adult (6 weeks) immune competent WT B6 mice (N=10/group) are immunized (i.p.) with different doses ($10^2$, $10^3$ and $10^4$ PFU) of rLCMV/GPCcd and rLCMV/Zcd selected based on the lowest virulence following i.c. inoculation using methods described elsewhere herein. Controls include mice immunized with rLCMV/WT ($10^3$ PFU, i.p.) and PBS mock-immunized mice. Four weeks after immunization mice are exposed to rLCMV/WT lethal challenge ($10^3$ PFU, i.c.), as described elsewhere herein. Challenged mice are monitored daily for the appearance of clinical symptoms. PBS mock-immunized mice are expected to develop clinical symptoms on day six post-challenge that will develop into a fatal LCM within the following 24-48 hours.

It is hypothesized that mice immunized with rLCMV/WT remain free of clinical symptoms throughout the entire duration of the experiment. Mice immunized with selected rLCMV/GPCcd and rLCMV/Zcd that do not develop clinical symptoms by day 12 after the lethal challenge (experimental end point) are scored as protected.

In the event that the viruses grow to poor titers in FDA-approved Vero cells, virus growth to WT levels may achieved by complementation of the viral proteins, in trans, using constitutively expressing cell lines. BHK-21 and Vero cells constitutively expressing LCMV NP (Ortiz-Riano et al., 2012, Viruses 4:2137-2161) and GPC (Rodrigo et al., 2011, J. Virology 85:1684-1695) that are able to complement NP- and GPC-deficient rLCMV, respectively, have been generated, representing an ideal substrate for the growth of CD viruses.

In the event that rLCMV/Zcd grows to low titers, constitutively Z-expressing cells may be generated to achieve high viral titers for vaccine production using previously disclosed methods (Cornu et al., 2004, J. Virology 75:9415-9426). It is hypothesized that rLCMV/GPCcd and rLCMV/Zcd are attenuated. In the event that the rLCMV/GPCcd and rLCMV/Zcd viruses fail to be attenuated, rLCMV containing multiple CD genes are generated using methods described elsewhere herein. It is hypothesized that CD rLCM viruses elicit a robust protection against rLCMV/WT challenge. In the event that the CD rLCM viruses fail to elicit protection as consequence of the excessive attenuation, higher immunization doses may be used.

Generation and Characterization of rLCMV with Multiple CD Genes

The results described herein with rLCMV/NPcd demonstrate that viral attenuation can be modulated by the number of CD amino acid introduced in the viral NP. Viruses with the higher degree of CD NP (NP1 and NP2) resulted in significant viral attenuation while viruses containing less CD NP resulted in less attenuation (NP7) that resulted in mortality upon i.c. inoculation (Table 1). It is hypothesized that generation of rLCM viruses containing multiple CD viral proteins would result in a higher attenuated phenotype than that observed with single protein CD rLCM viruses. Moreover, generation of rLCM viruses containing multiple CD viral proteins would result in viruses carrying attenuation in both viral genes and segments and, thus, would be less likely to revert to WT or to generate virulent reassortants with circulating WT viruses.

Generation and Characterization in Cultured Cells of rLCMV Containing Multiple CD Viral Proteins rLCMV containing combinations of CD NP, GP, and Z viral proteins are selected. Selection of the appropriate CD rLCMV is based on the ability to 1) efficiently generate replicating competent viruses, and, 2) show some degree of attenuation individually but not to an extend that guarantee their further development as candidate vaccine based on attenuation of a single viral protein. rLCMV are generated via reverse genetics and characterized using methods described elsewhere herein. The identity of the recombinant CD rLCMV is confirmed by RT-PCR and sequencing. Generated double or triple CD rLCMV are compared to WT and individual CD rLCMV regarding growth kinetics, RNA synthesis and protein expression levels in cultured cells using methods described elsewhere herein.

Characterization of Selected Double or Triple CD rLCMV In Vivo

Mouse experiments are performed to evaluate the ability of selected rLCMV containing two or three CD viral proteins in their ability to induce fatal LCM, to persist in an immunocompetent adult mouse following iv inoculation, and to induce an immune protective response against LCMV-induced lethal LCM, as described elsewhere herein.

In the event that the generation of rLCMV containing multiple CD viral proteins results in poor titers in Vero cells, stable cell lines constitutively expressing two or three viral proteins may be generated. It is hypothesized that viruses containing multiple CD genes are more attenuated than those encoding a single CD gene and, therefore, will not elicit a robust protection against rLCMV/WT challenge. If a robust protection against rLCMV/WT challenge is elicited, higher immunization doses or, alternatively, multiple CD rLCMV immunizations may be used.

Characterization of the Immune Protective Response Induced by Selected CD rLCMV in the Mouse Model of LCMV Infection One component of the characterization of a candidate LAV relates to the correlation between the nature and magnitude of the immune responses in immunized individuals and protection against disease induced by pathogenic viral strains. Three CD rLCMV that exhibit: 1) lower virulence (higher LD50) in the model of i.c. inoculation, and 2) lower i.p. viral dose capable to protect against a subsequent lethal challenge with rLCMV/WT are selected. These selected CD rLCMV are used to immunize mice using difference viral doses and characterize the nature and magnitude of both T- and B-cell (Ab) responses against LCMV, and their correlation with protection against rLCMV/WT lethal challenge. This model is cost effective, robust, and well characterized in terms of how both T cell and Ab-mediated responses contribute to protection. Information derived from these studies aids in designing improved versions of CD rLASV that are investigated as candidate vaccines in a qualified guinea pig model of LF.

Adult (6 weeks) immune competent B6 mice with CD rLCMV are immunized (i.p., $10^5$ PFU). Four weeks later, splenocytes from the mice are used in ELISpot assays to measure the number of interferon-γ (IFN-γ)- and IL-2-secreting lymphoid cells after exposure to LCMV NP and GP specific peptides. Intracellular cytokine staining by flow cytometry is used to characterize T cell immune responses in immunized and naïve mice.

As complementary studies to characterize T cell responses in vivo, cytotoxicity assays are conducted. Titers of LCMV NAbs are assessed using a standard focus reduction neutralization (FRNT) assay or a previously described GFP-based microneutralization assay (Rodrigo et al., 2011, J. Virology 85:1684-1695), although existing evidence indicates that NAbs may develop only at much later times.

ELISPOT Assays

Splenic CD8+ T cells ($4\times10^5$), isolated by anti-CD8-coated magnetic beads, are cultured with $1\times10^5$ peptide-pulsed JA2.1 target cells. Effector and target cells are incubated in flat-bottom 96-well nitrocellulose plates pre-coated with an anti-IFN-γ MAb. After 16 to 20 h, plates are washed and wells incubated with 100 μl biotinylated anti-IFN-γ MAb (1 μg/m1Mabtech R4-6A2) for 2 h. After additional washing, spots are developed by sequential incubation with Vectastain ABC peroxidase and 3-amino-9-ethyl carbazole solution and counted by computer-assisted image analysis (Zeiss KS ELISPOT reader). Assays are performed in triplicates, and results expressed as the mean spots/$10^6$ $CD8^+$ T cells±standard deviations (SD) for each peptide. Responses of $CD8^+$ T cells derived from peptide-immunized mice against JA2.1 cells pulsed with irrelevant peptide are measured to establish background values.

In Vivo Cytotoxicity Assays

Splenocytes are labeled with 0.3 μM or 0.06 μM CF SE (Molecular Probes). CFSEhi cells are pulsed with 1 μg/ml of virus-specific peptides while $CFSE^{lo}$ cells are pulsed with 1 μg/ml of an irrelevant peptide. Following extensive washing, equal numbers of $CFSE^{hi}$ and $CFSE^{lo}$ cells are mixed and delivered (~$8\times10^6$ total cells per mouse) via intravenous (iv) injection to syngeneic immunized, and control, mice. After 18 h, CFSE-labeled cells are identified from the spleens of recipient mice by flow cytometry.

The percent killing is determined as follows: 100−{[(% of immunizing peptide-pulsed cells in peptideimmunized or LCMV-infected mice/% of irrelevant peptide-pulsed cells in peptide-immunized or LCMV-infected mice)/(% of immunizing peptide-pulsed cells in adjuvant-immunized or naïve mice/% of irrelevant peptidepulsed cells in adjuvant-immunized or naïve mice)]×100}. Cell staining is analyzed by flow cytometry using a BD Biosciences FACSCalibur flow cytometer and CellQuest software.

Intracellular Cytokine Staining

Spleens are collected from immunized and control mice (N=7). Total splenocytes are treated for 5 h with NP and GPC peptides (0.5 μg/ml) in the presence of the protein transport inhibitor GolgiStop. $CD4^+$ and $CD8^+$ T cells expressing IFN-γ- and IL-2- are assessed by flow.

Virus Neutralization Assays

Log neutralization index is determined by quantifying reduction on infectivity of a predetermined amount of virus upon exposure to serum antibody samples. Equal volumes of undiluted and serially diluted serum and viral stock ($10^6$ PFU/ml) are mixed and incubated for 60 min at 37° C. Following incubation the virus-antiserum mixture is cooled by immersion in ice and virus titers determined using a standard plaque assay on Vero cells using previously described methods (Rodrigo et al., 2011, J. Virology 85:1684-1695). Reduction of viral titer due to the activity of the antibody is expressed as the $\log_{10}$ reduction of titer when normalized against control, non-immune serum45. A similar experimental approach with modifications, is use to assess the presence of NAbs using a previously described GFP-based microneutralization assay (Rodrigo et al., 2011, J. Virology 85:1684-1695).

In the event that antibodies are not readily detectable at the indicated times post immunization, mice sera is also collected at later times post infection. Similarly, in the event of diminished or delayed in vivo viral replication, T cell studies may need to be evaluated at earlier or later times, respectively, post infection.

Genetic and Phenotypic Stability of Selected CD rLCMV

Genetic stability is an important concern for production of any viral LAV. Genetic instability maydetermine that during multiple rounds of infections in cultured cells, a process required for vaccine production, some mutations can be fixed within the viral population at levels sufficient to impact the phenotypic properties of the virus population including reversion from an attenuated to a more virulent phenotype. This issue may be particularly relevant when dealing with RNA viruses because their error prone replication machineries determine that RNA viral populations exist as a mixture of genetically closely related RNA species, termed quasispecies, distributed around a master sequence. This determines that replicating RNA viruses have available a large pool of variants, most of them kept at very low frequency, that could be used to respond to changes in the environment by selecting variants with increased fitness under the novel environmental selective pressures. Therefore, it is critical to determine the genetic and phenotypic stability of CD rLCMV selected as vaccine candidates.

Generation of P2 Stocks of Selected CD rLCMV

Two (P2) stocks of clonal populations derived from each selected CD rLCMV in Vero cells (and rLCMV/WT) are generated and the consensus sequences of the corresponding CD ORF are determined in order to confirm that they match the corresponding sequences in pPol-I-Sag (GPC and NP) and pPol-I-Lag (Z) plasmids used for viral rescues. The phenotypic properties of P2 viral populations are confirmed first with respect to their growth properties in cultured cells and virulence using i.c. mice inoculations prior to being used in studies to assess their phenotypic and genetic stability.

Genetic and Phenotypic Stability of CD rLCMV 7 During Serial Passages in Cultured Cells A P2 population of CD rLCMV characterized as described above is used to conduct independent (N=3) serial passages (total of P1 to P10 for each series) in Vero cells. For each passage, cells are infected at MOI=0.1 and, at 72 h p.i. TCS is collected for determination of infectious titers and RNA isolation. At the same times p.i. total cellular RNA is collected. Selected serial passages in cultured cells (P1, P5 and P10) are characterized genetically (genome sequence) and phenotypically (growth kinetics in cultured cells and virulence in mice).

Genetic Stability

For the genetic analysis, RNA is isolated from virions present in TCS of serial viral passages in culture following their concentration by ultracentrifugation. Virion-derived RNA is used first in standard chain termination (Sanger) sequencing protocols to determine the consensus genome sequence. In cases where the amount of RT-PCR product obtained from virions would be found to be insufficient, intracellular RNA from the same passage is used. The advantage and preference of using virions as source of RNA is that for the most it would exclude abortive products of transcription and replication that could add some noise to the sequence analysis of these samples.

Mutations generated during these serial passages and able to rise to detectable levels within the quasispecies population are likely subjected to positive selection, and their full potential impact on virus phenotype is assessed. CD rLCMV carrying these mutations is rescued and characterized using the assays described below to assess virus phenotypic stability.

In addition to determine the consensus genome sequences of P1, P5 and P10, RNA from P1 and P12 is used for pyrosequencing (454) reactions to gain a better understanding of the quasispecies dynamics of each viruses during serial passages. This permits the determination of whether RNA species carrying reversions associated with potential increase in virulence may be present at low frequency within the population, and whether their frequency increases over time.

Phenotypic Stability

The same selected viral populations used for the genetic analysis described above are also subjected to a phenotypic characterization based on their growth properties in cultured cells and virulence in mice as described elsewhere herein.

All tested CD rLCMV will have a large number of silent mutations within their genomes, and therefore reversion at one or several positions cannot result in amino acid substitutions associated with increased virulence. Because the amino acid composition of the viral polymerase (L) is not altered in CD rLCMV, it is hypothesized that these viruses will not exhibit increased mutation frequencies over the $10^{-3}$ to $10^{-4}$ characteristically observed with riboviruses. Therefore, the numbers of reversions resulting in the re-establishment of naturally occurring codons at several amino acid positions are hypothesized to be very low. Inclusion of rLCMV/WT in these studies assists in determining the frequency of mutations related to the fidelity of the viral polymerase. In the event that these limited number of reversions result in fitness gain and hence increased virulence, the virulence of CD rLCMV exhibiting the highest number of mutations during serial passages is compared with that of their corresponding parental population.

Assess The Potential of CD rLASV As LAV Using the Guinea Pig Model of LF

The epidemiology of LASV infection in West Africa indicate that a LAV remains the most feasible approach to control LF (Falzarano and Feldmann, 2013, Curr. Opin. Virol. 3:343-351). LAV usually induce a robust cellular and humoral immune responses following a single immunization, which is desirable for vaccine use in rural areas of West Africa. Studies with CD rLCMV provide data for the rationale design of CD rLASV for the development of safe and effective LF LAV candidates. In one embodiment, rescued infectious rLASV from cloned cDNAs using reverse genetics are used for the generation of selected CD rLASV (Yun et al., 2013, J. Virology 87:10908-10911).

Efficacy studies for vaccines to prevent LF will be conducted under the application of the Animal Rule (21 CFR 601.90 subpart H), created to facilitate the collection of evidence of effectiveness through studies conducted in animal models to establish a pathway to licensure for human use. The Animal Rule requires the demonstration of efficacy in one or more animal models that are expected to predict effect in humans. Infection of guinea pigs with LASV recreates accurately many of the features associated with LF in humans. The guinea pig model is widely used to test therapeutics and vaccines for HF-causing arenaviruses. The safety, immunogenicity and efficacy of selected CD rLASV is assessed using the guinea pig model of LF (Yun et al., 2013, J. Virology 87:10908-10911). The use of BSL4 facilities is required and is performed in collaboration with Dr. Paessler whose laboratory at UTMB, Galveston, is highly experienced in the use of reverse genetics approaches to rescue and characterize, both in culture cells and animal models, HF-causing arenaviruses including JUNV and LASV (Yun et al., 2013, J. Virology 87:10908-10911; Yun et al., 2012, J. Virology 86:3389-3392).

Rescue and Characterization in Cultured Cells of Selected CD rLASV

The specific CD rLASV that are rescued are the equivalent counterparts of the three CD rLCMV that exhibited an improved profile as LAV candidates in mice as determined by: 1) lower virulence (highest LD50) in the i.c. challenge, 2) strongest immunogenicity following i.p. immunization, and, 3) highest efficacy as determined by lowest dose of virus required in a single vaccination (i.p.) to confer 50% protection against a subsequent lethal challenge (i.c., $10^3$ PFU) with rLCMV/WT.

The experimental procedures for the de novo synthesis and characterization of CD ORFs of LASV, as well as for the rescue of the corresponding CD rLASV, are described elsewhere herein for rLCMV. The rescued CD rLASV is characterized in cultured cells by evaluating growth kinetics, viral RNA synthesis and protein expression levels in Vero and A549 cells using the same procedures described elsewhere herein for CD rLCMV.

Characterization In Vivo of Selected CD rLASV

Virulence: To assess the virulence of selected CD rLASV, 8-20 weeks old Hartley guinea pigs (N=5/group) are infected (i.p.) with different doses (10, $10^2$, $10^3$ and $10^4$ PFU) of CD rLASV, as well as rLASV/WT (Josiah strain) (Yun et al., 2013, J. Virology 87:10908-10911; Yun et al., 2012, J. Virology 86:3389-3392). Guinea pigs are observed daily for disease symptoms and mortality. Blood and tissue samples are collected at 3, 10 and 17 days p.i. Blood samples are used for virus titration, hematological and clinical chemistry analyses. Tissues are examined for histopathology and to determine infectious virus in organs (Yun et al., 2013, J. Virology 87:10908-10911; Yun et al., 2012, J. Virology 86:3389-3392).

Clinical Evaluation

Animals are monitored daily throughout the duration of study for signs of disease including changes in body weight and body temperature (Yun et al., 2013, J. Virology 87:10908-10911; Yun et al., 2012, J. Virology 86:3389-3392). Guinea pigs infected with rLASV/WT develop fever followed by hypothermia and significant weight loss and will succumb to infection 14-18 days after infection (Yun et al., 2013, J. Virology 87:10908-10911; Yun et al., 2012, J. Virology 86:3389-3392). If guinea pigs infected with CD rLASV do not develop clinical symptoms by day 17 p.i., the infection is allowed to proceed until day 30, or the earliest time at which significant clinical symptoms are observed.

Hematology and Clinical Chemistry

Blood is collected from guinea pigs for standard hematological analysis using the HEMAVET®1700 (automatic hematology analyzer) on whole blood to determine platelet and differential counts. Clinical chemistry analysis will be performed on the ACE Alera™ Clinical Chemistry System (chemistry analyzer).

Telemetry

For measurement of body temperature, animals are anaesthetized and implanted subcutaneously with BMDS IPTT-300 transponders (chips) purchased from Bio Medic Data Systems, Inc., using a trocar needle assembly. Animals are monitored for signs of infection or migration of transponder for two days prior to transfer into the ABSL-4 facility. Chips are scanned daily using a DAS-6007 transponder reader and digital temperature data are downloaded as per manufacturer's protocol.

Infectious Virus in Organs

Tissue specimens are dissected at necropsy and homogenized in MEM containing 1% penicillin-streptomycin solution. Suspensions are clarified by centrifugation, and the supernatants harvested and frozen at −80° C. until analysis are performed. The titer of infectious virus is determined using standard plaque assays.

Histopathology

Brain, liver and spleen sections are fixed in 10% buffered formalin for 7 days and stored in 70% ethanol for 12 h. Samples are then embedded in paraffin, sectioned (4 µm) and mounted on slides, and standard H&E staining is performed. For immunohistochemical analysis tissue sections are deparaffinized and rehydrated through xylene and graded ethanol solutions.

To block endogenous peroxidase activity, slides are treated with a solution of Tris-buffered saline containing 0.1% TWEEN-20® (Polysorbate 20) (TBST), 3% hydrogen peroxide and 0.03% sodium azide for 15 min, followed by heat antigen retrieval in a water bath at 95° C. for 40 min in DAKO Target Retrieval Solution, pH 6.1. To block endogenous biotin reactivity, sequential 15 min incubations with Avidin D and Biotin solutions are performed. To prevent nonspecific protein binding, sections are incubated in blocking solution according to manufacturer's instructions (Histomouse™-SP Kit, Zymed (histology kit)). For viral antigen staining, a NHP serum to LASV is used (Rodrigo et al., 2011, J. Virology 85:1684-1695).

Tissue sections from uninfected animals are used as negative controls. To detect antibodies bound to viral antigen in animal tissues, the Histomouse™-SP Kit (Zymed) (histology kit) biotinylated secondary antibody is used, followed by streptavidin-peroxidase. Color development is achieved using the chromogenic substrate, according to the manufacturer's instructions. Slides are counter-stained with Mayer's modified hematoxylin for microscopy.

Induction of Protective Immune Responses

Hartley guinea pigs (8-20 weeks old) are immunized with selected CD rLASVs. A control group (N=4) is mock vaccinated. Humoral and cellular immune response to the vaccine candidate are specifically evaluated on days 30 and 60 post-vaccination. Plasma and peripheral blood mononuclear cells (PBMCs) are obtained and assayed for the presence of antibodies and cellular mediated immune responses, respectively. Humoral response to the vaccine is evaluated by the presence of IgM, IgG and IgA in serum using an ELISA. Furthermore, NAbs to LASV are evaluated using a qualified FRNT assay or the GFP-based microneutralization assay using a LASV GPC-pseudotyped rLCMVΔGPC/GFP (Rodrigo et al., 2011, J. Virology 85:1684-1695).

Because production of IFN-γ by helper T cells as well as cytotoxic T cells is a hallmark of the TH1-type phenotype, an IFN-γ ELISpot assay is used for the investigation of cellular immune responses to the vaccine. Positive controls for the assay include PBMCs stimulated with Concanavalin A. Differences between mock, WT and CD rLASV are assessed using ANOVA implemented in the GraphPad program. A P-value ≤0.05 isconsidered significant. Immunized guinea pigs are then challenged (i.p.) with a lethal dose of rLASV/WT and monitored daily throughout the duration of study for signs of disease using procedures described elsewhere herein.

Example 2: Generation and Characterization of rLCMV/GPcd

Figures 6C, 6D:
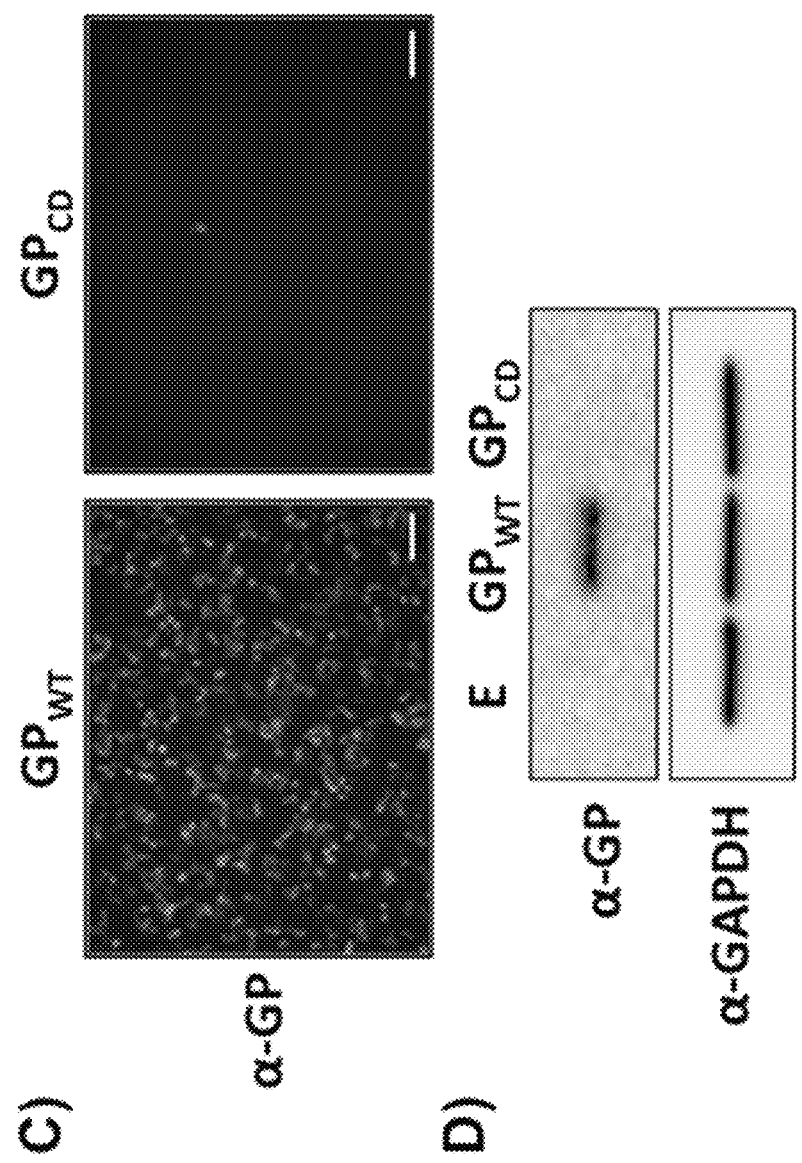

The GPC s were deoptimized attending to the mammalian codon usage using the same strategy described in Example 1. ORF Multiple silent mutations were introduced to replace the current sequences by underrepresented codons without affecting GPC amino acid compositions (FIG. 6A). A summary of nucleotide and amino acid changes in the codon deoptimized LCMV GP (LCMV $GP_{CD}$) are provided in FIG. 6B.

To determine the effect of codon deoptimization on LCMV GPC protein expression, HEK293T cells were transfected with CD GP pCAGGS (1 µg) expression plasmids for wild-type (WT) or codon deoptimized (CD) GP. Protein expression was detected after 48 hours post-transfection by immunofluorescence assay (FIG. 6C) and western blot (FIG. 6D) using a mouse monoclonal anti-LCMV GP1 antibody. Empty plasmid was included as negative control in the Western blot. Detection of GAPDH was included as a loading control. Codon deoptimization of LCMV GP was found to reduce LCMV GP expression in transfected human 293T cells.

Figure 7:
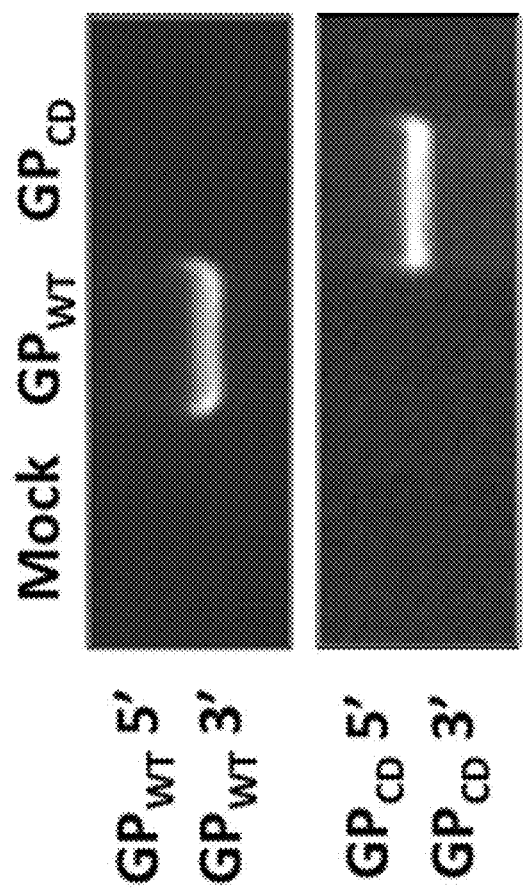
FIG. 7 is an image depicting the results of experiments confirming the generation of a rLCMV expressing codon deoptimized GP (rLCMV/GPcd). Using plasmid-based reverse genetics techniques, a recombinant LCMV expressing a full codon-deoptimized GP (rLCMV/GPcd) was generated. Virus rescue was confirmed by RT-PCR using specific primers to amplify GP from wild-type virus (LCMV WT) or the codon deoptimized GP (rLCMV/GPcd). BHK-21 cells were mock infected (M) or infected (MOI of 0.01) with rLCMV/WT or rLCMV/GP$_{CD}$. At 72 hours post infection cells were collected and rLCM viruses were characterized by RT-PCR using wild-type (WT) or codon deoptimized (CD) GP specific primers. RT-PCR products were analyzed on a 1% DNA agarose gel.

Using plasmid-based reverse genetics techniques, a recombinant LCMV expressing a full codon-deoptimized GP (rLCMV/GPcd) was generated. Virus rescue was confirmed by RT-PCR using GP-specific primers to amplify GP from wild-type virus (LCMV WT) or the codon deoptimized GP (rLCMV/GPcd) (FIG. 7).

Figure 8:
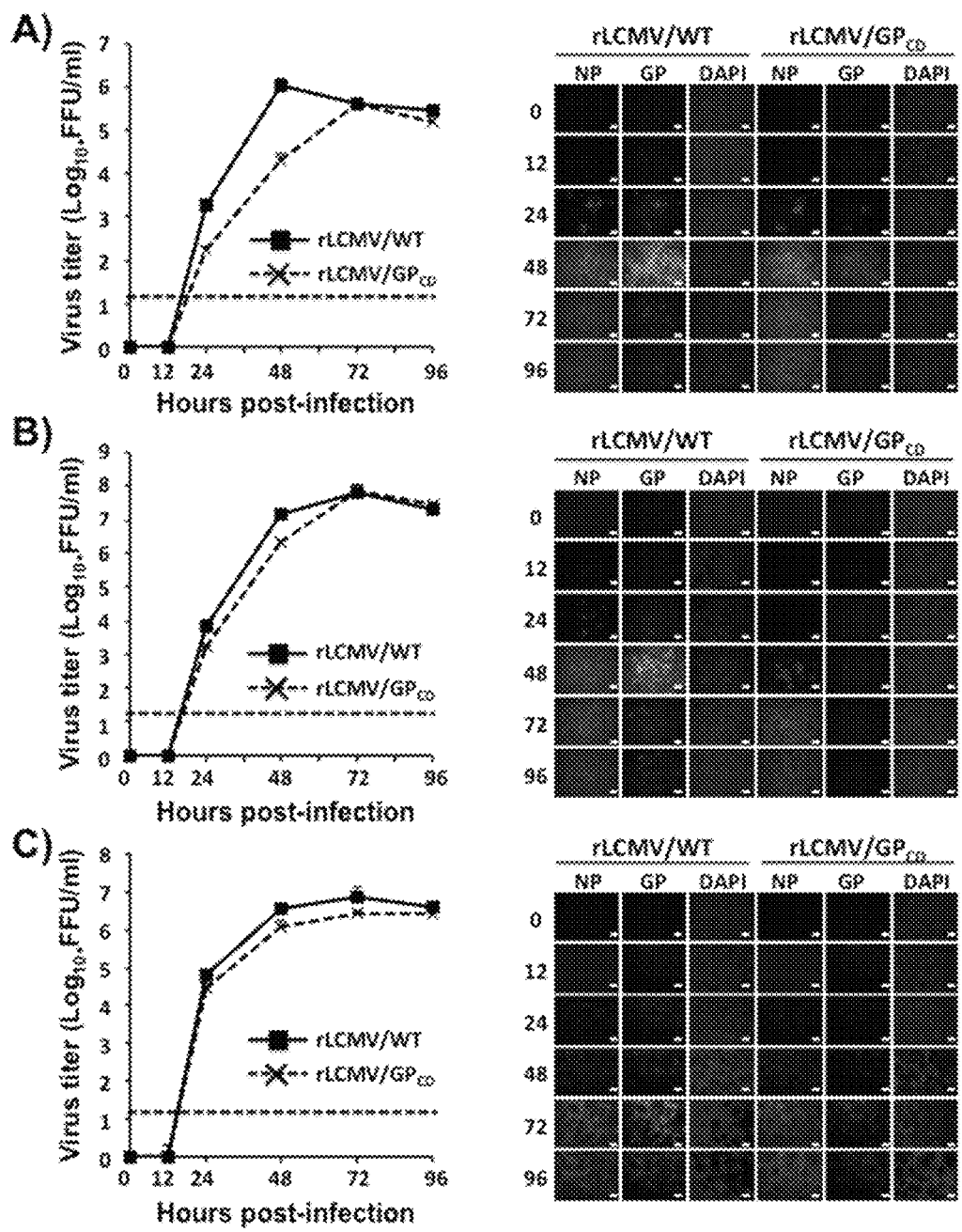
FIG. 8, comprising

Generation and Characterization in Cultured Cells of rLCMV/GPCcd—In Vitro Characterization of rLCMV/GP-Ccd The rLCMV expressing CD GPC proteins were characterized by evaluating their growth kinetics in HA549 (FIG. 8A), BHK-21 (FIG. 8B), and Vero (FIG. 8C) cells. Cells were infected with either rLCMV/WT or rLCMV/GPcd (moi 0.01). At the indicated times post-infection, tissue cultures were collected and viral titers were determined by immunofocus (FFU/ml) assay (FIG. 8A-FIG. 8C; left)

HA549 (FIG. 8A), BHK-21 (FIG. 8B), and Vero (FIG. 8C) cells were also stained with NP and GP antibodies to evaluate viral replication. Cell nuclei were stained using DAPI. Both WT and GPcd rLCM viruses were observed to grow to similar titers in murine BHK-21 cells. Contrary to the situation observed in murine BHK-21 cells, rLCMv/GPcd kinetics were reduced as compared to rLCMV WT in human A549 cells. In IFN-deficient Vero cells, rLCMV/GPcd kinetics were found to be similar to those observed with rLCMV WT.

Figure 9:
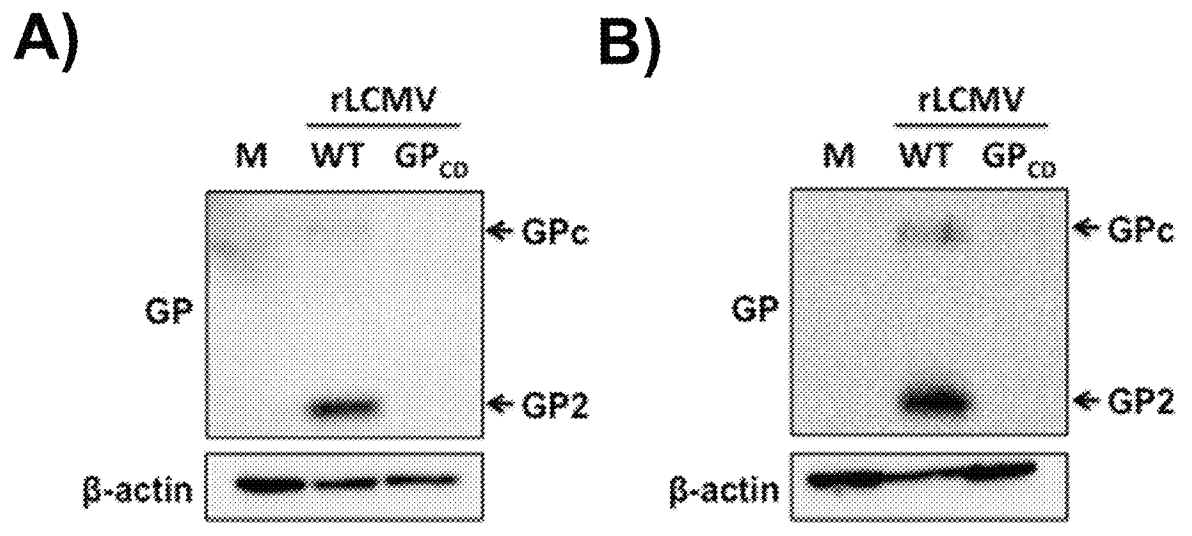

Experiments were conducted to evaluate mRNA and protein expression of wild-type and codon deoptimized LCMV GP. A549 (FIG. 9A) and BHK-21 (FIG. 9B) cells were mock infected or infected (MOI of 0.01) with rLCMV/WT or rLCMV/$GP_{CD}$. AT 48 hours post-infection, cells were collected and evaluated for GP mRNA expression by Northern blot and protein expression (FIG. 9A and FIG. 9B) using the LCMV GP monoclonal antibody 83.6. Beta-actin expression levels were used as loading controls. The data demonstrates that codon deoptimization effected protein levels but not mRNA levels.

Figure 10:
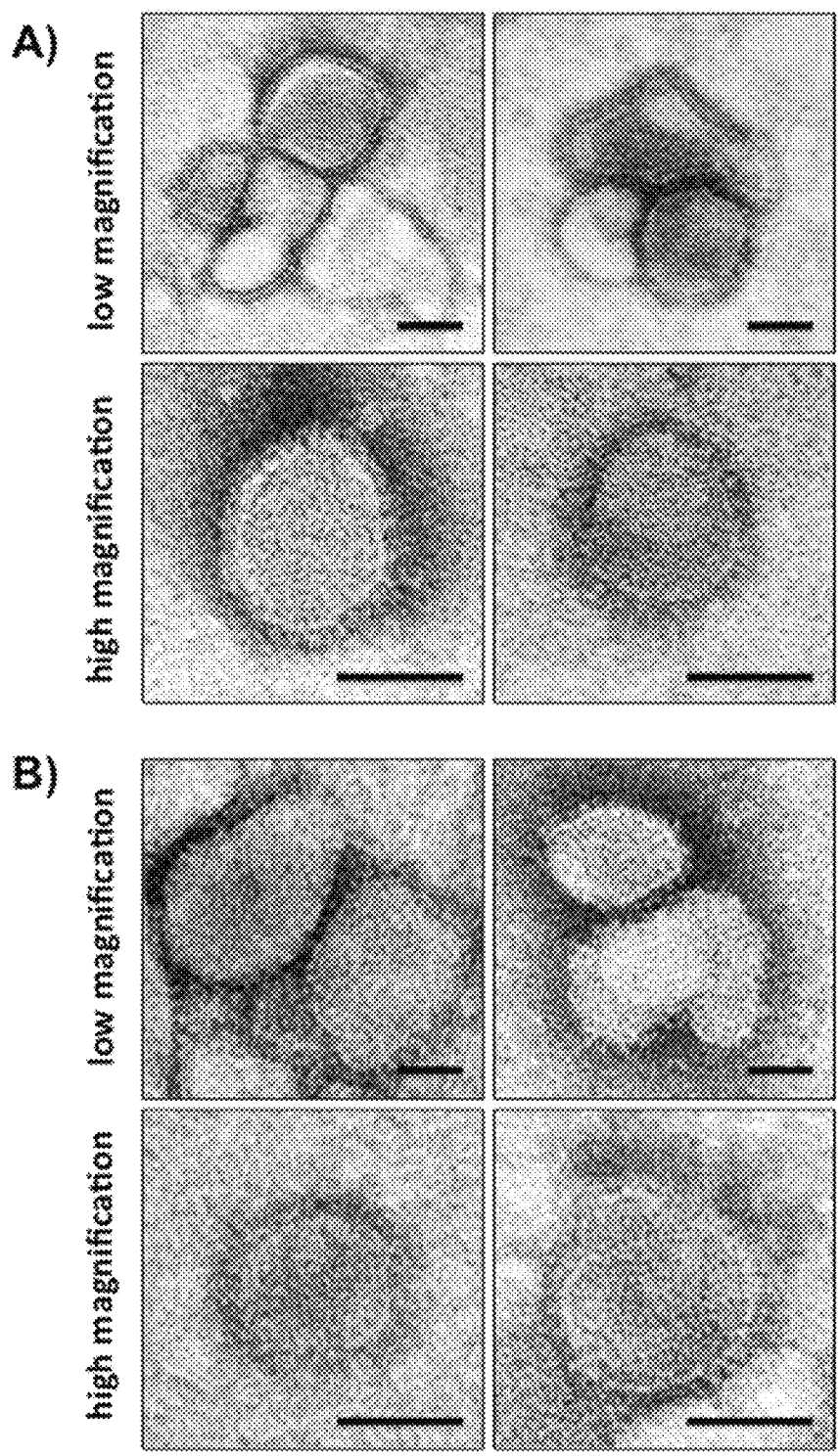
FIG. 10, comprising FIG. 10A
Figure 11A:
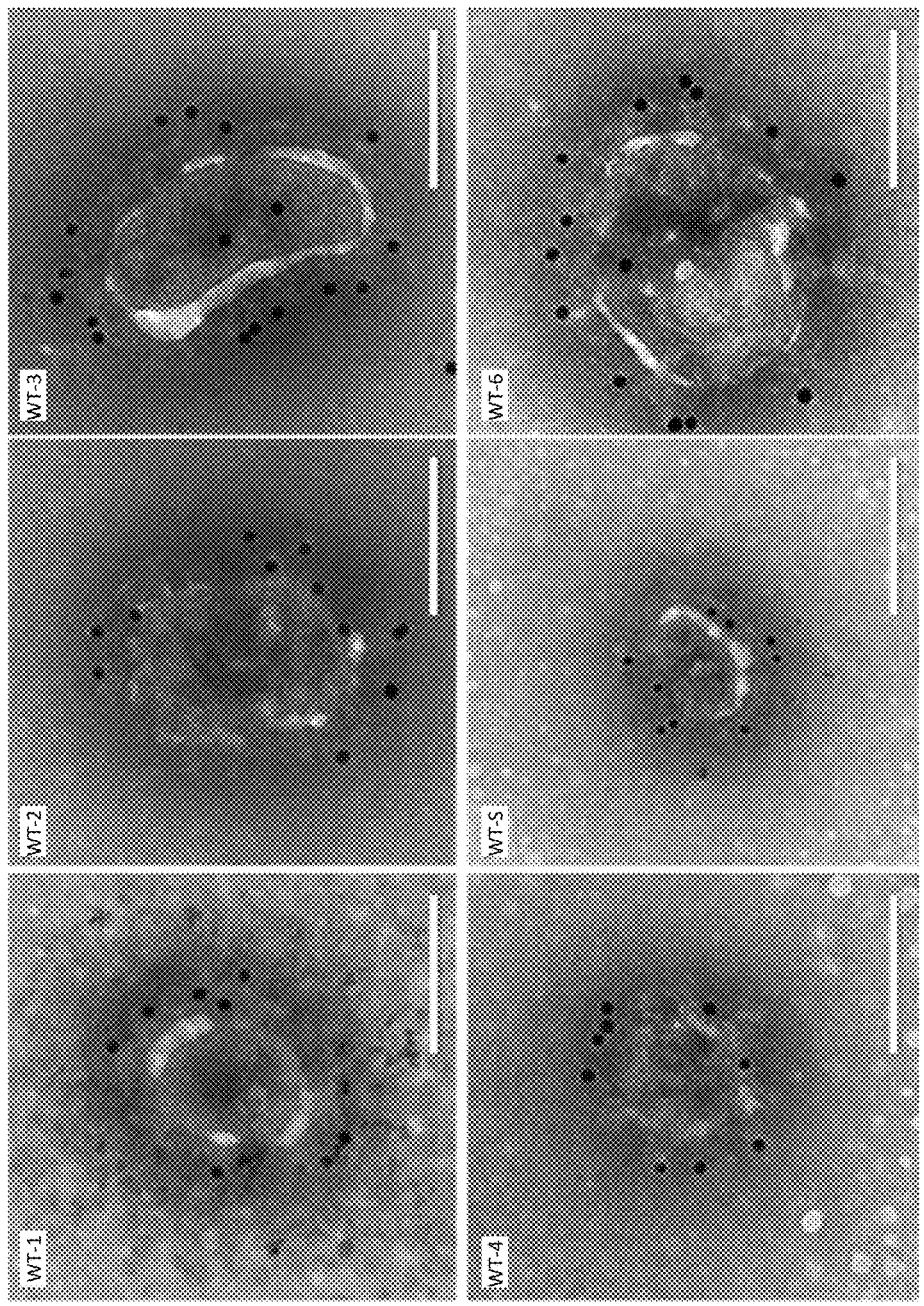
FIG. 11A and FIG. 11B, depicts immunoelectron microscopy (TEM) images of LCMV WT and GPcd. Purified rLCMV WT (FIG. 11A) and GPcd (FIG. 11B) were stained with GP monoclonal antibody against GP2 83.6 in order to evaluate the presence of GP incorporated into purified viral particles. GP was detected in LCMV WT but not in rLCMV/GPcd. Antibody was diluted 1:1. Scale bar=100 nm.
Figure 11B:
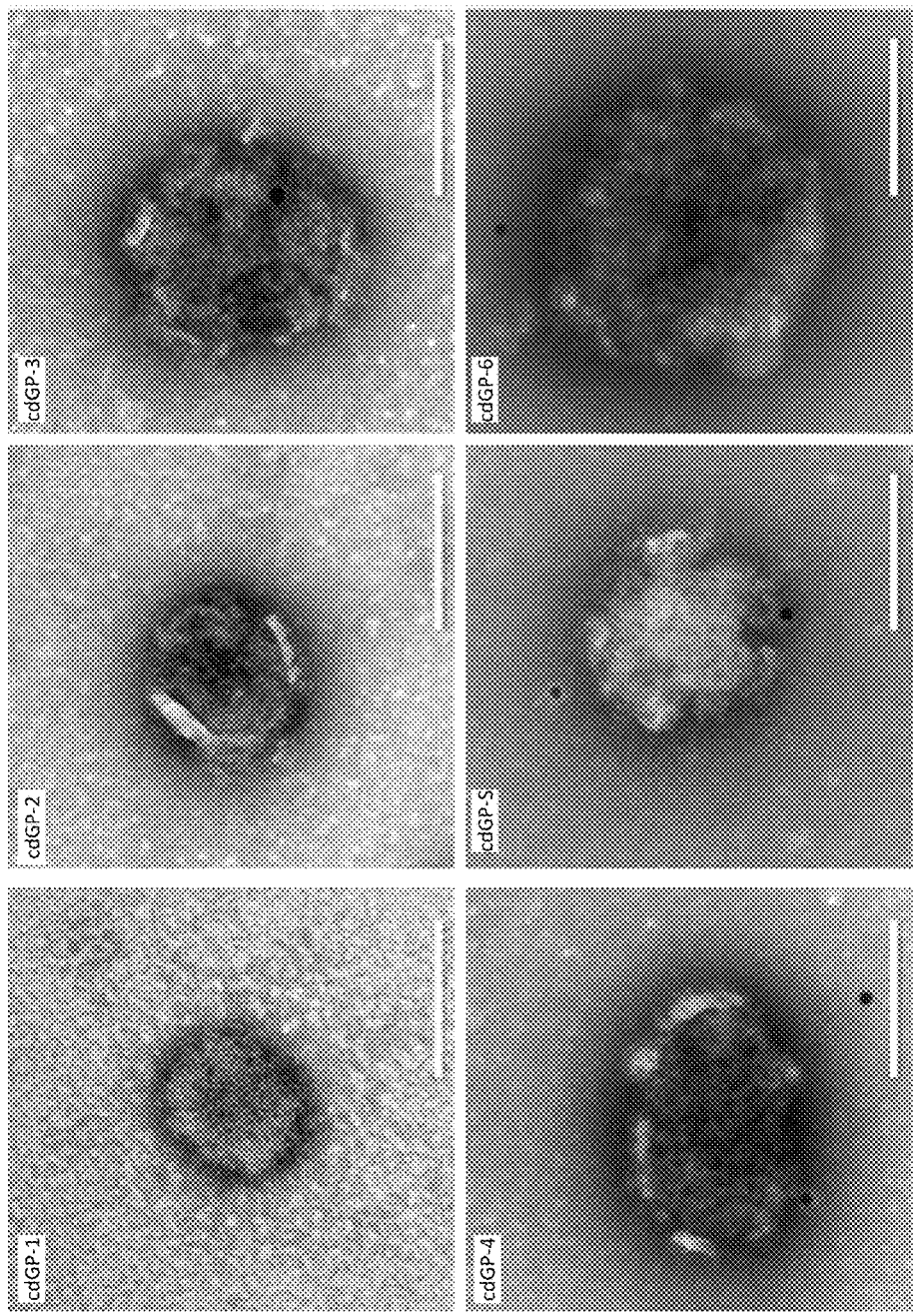

In order to evaluate the incorporation of GPcd into virion particles, rLCMV WT (FIG. 10A) and GPcd (FIG. 10B) viruses were purified and analyzed by transmission electron microscopy. Both viruses were found to have the same viral morphology and viral sizes. Purified rLCMV WT (FIG. 11A) and GPcd (FIG. 11B) viruses were also stained with GP monoclonal antibody against GP2 83.6 in order to evaluate the presence of GP incorporated into purified viral particles. GP was detected in LCMV WT but not in rLCMV/GPcd purified viruses (FIG. 11), which is quantified in table form in FIG. 12A and graphed in FIG. 12B.

Figure 13:
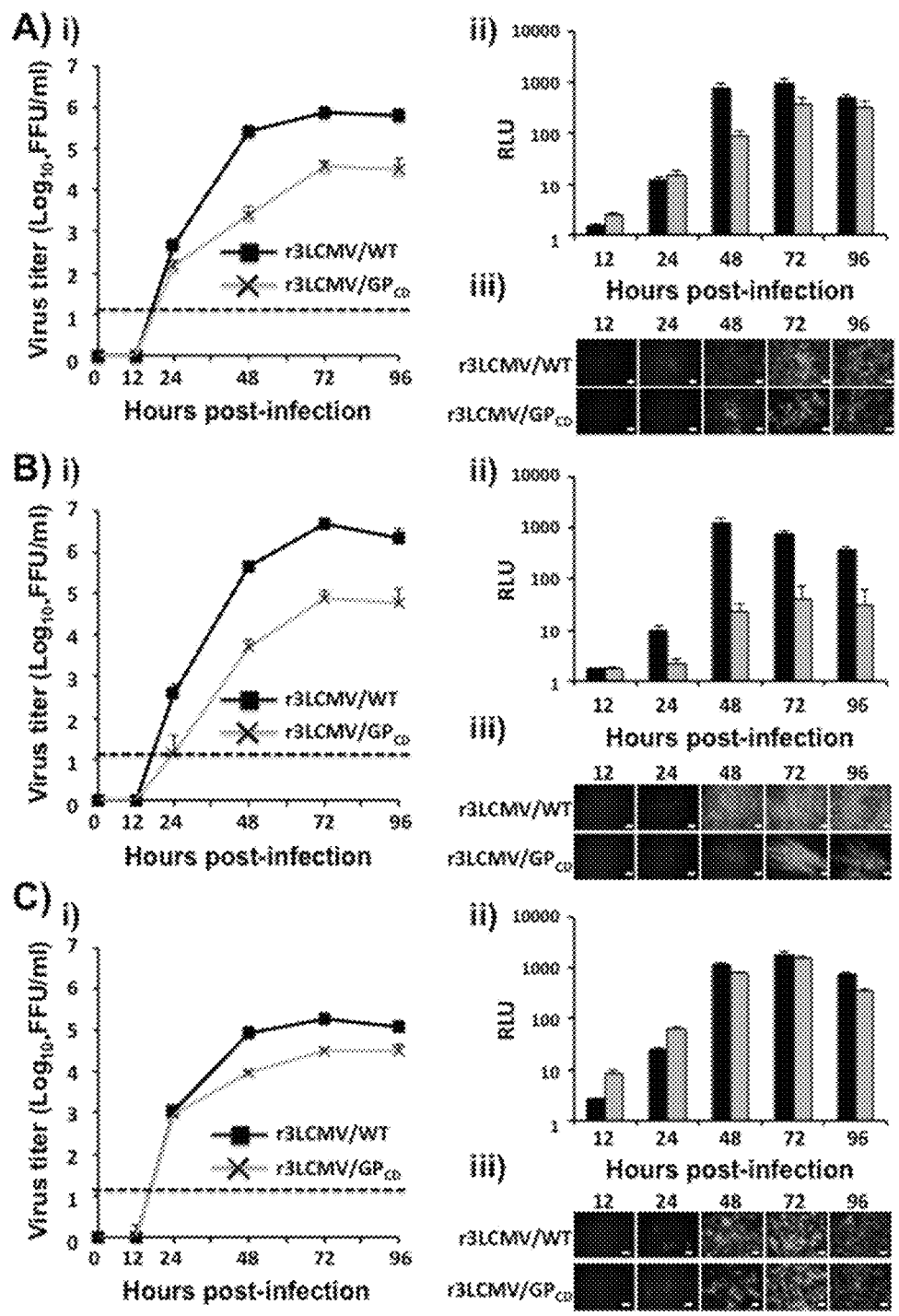
FIG. 13, comprising

The growth kinetics of r3LCMV/$GP_{CD}$ was examined in A549 (FIG. 13A), BHK-21 (FIG. 13B), and Vero (FIG. 13C) cells. Cells were infected (MOI 0.01) with either rLCMV/WT or rLCMV/$GP_{CD}$ and viral titers in TCS at the post-infection were determined by focus forming units (i). Gluc activity in same TCS was assessed by luminescence (ii). GFP expression from infected cells was determined by fluorescence microscopy (iii).

In vivo experiments were conducted to evaluate the effect of GP codon deoptimization on the mortality of infected animals. Six week-old male B6 mice (n=8) were infected (i.c, $10^3$ PFU) with rLCMV/WT or rLCMV/$GP_{CD}$, or inoculated with the virus diluent, PBS. Mice were monitored daily for morbidity and mortality until the experimental endpoint (12 days p.i.). It was observed that while mice infected with wild-type rLCMV all died within 8 days post infection, 100% of mice infected with rLCMV/$GP_{cp}$ survived until the endpoint of the experiment (FIG. 14).

Further in vivo experiments were conducted to determine if rLCMV/$GP_{CD}$ protects against a subsequent lethal challenge of wildtype virus. Six week-old male B6 mice (n=8) were immunized with the indicated viruses (i.p., $10^5$ PFU) or inoculated with the virus diluent (PBS) and four weeks later infected with rLCMV/WT (i.c., $10^3$ PFU). Mice were monitored daily for morbidity and mortality. It was observed that immunization with either wildtype or $GP_{CD}$ LCMV protected against subsequent challenge, whereas mice immunized with negative control (PBS) all died within 8 days post-challenge (FIG. 15).

Example 3: Generation and Characterization of rLCMV/Zed

The Z ORFs were deoptimized attending to the mammalian codon usage using the same strategy described in Example 1. FIG. 16 depicts the nucleotide sequence (FIG. 16A) and deoptimized codons (FIG. 16B) of LCMV matrix (Z) protein. Multiple silent mutations were introduced to replace the current sequences by underrepresented codons without affecting Z amino acid compositions.

Figure 17:
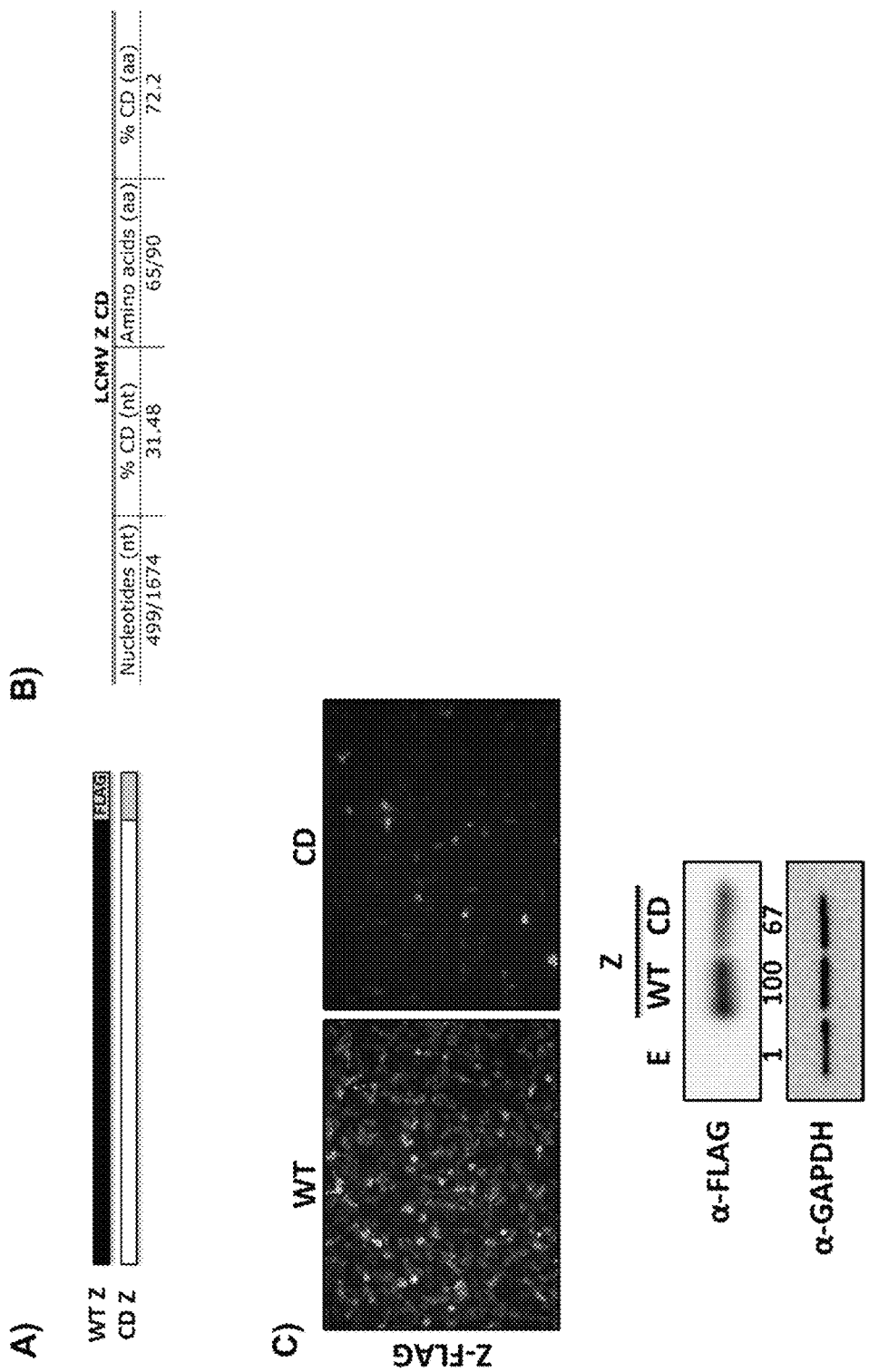
FIG. 17, comprising

Codon deoptimization was found to affect LCMV Z expression (FIG. 17). Protein expression levels of LCMV WT and CD were examined using immunofluorescence and Western blot assays (FIG. 17C).

Generation and Characterization of CD LCMV Z Chimeric Constructs

Figure 18:
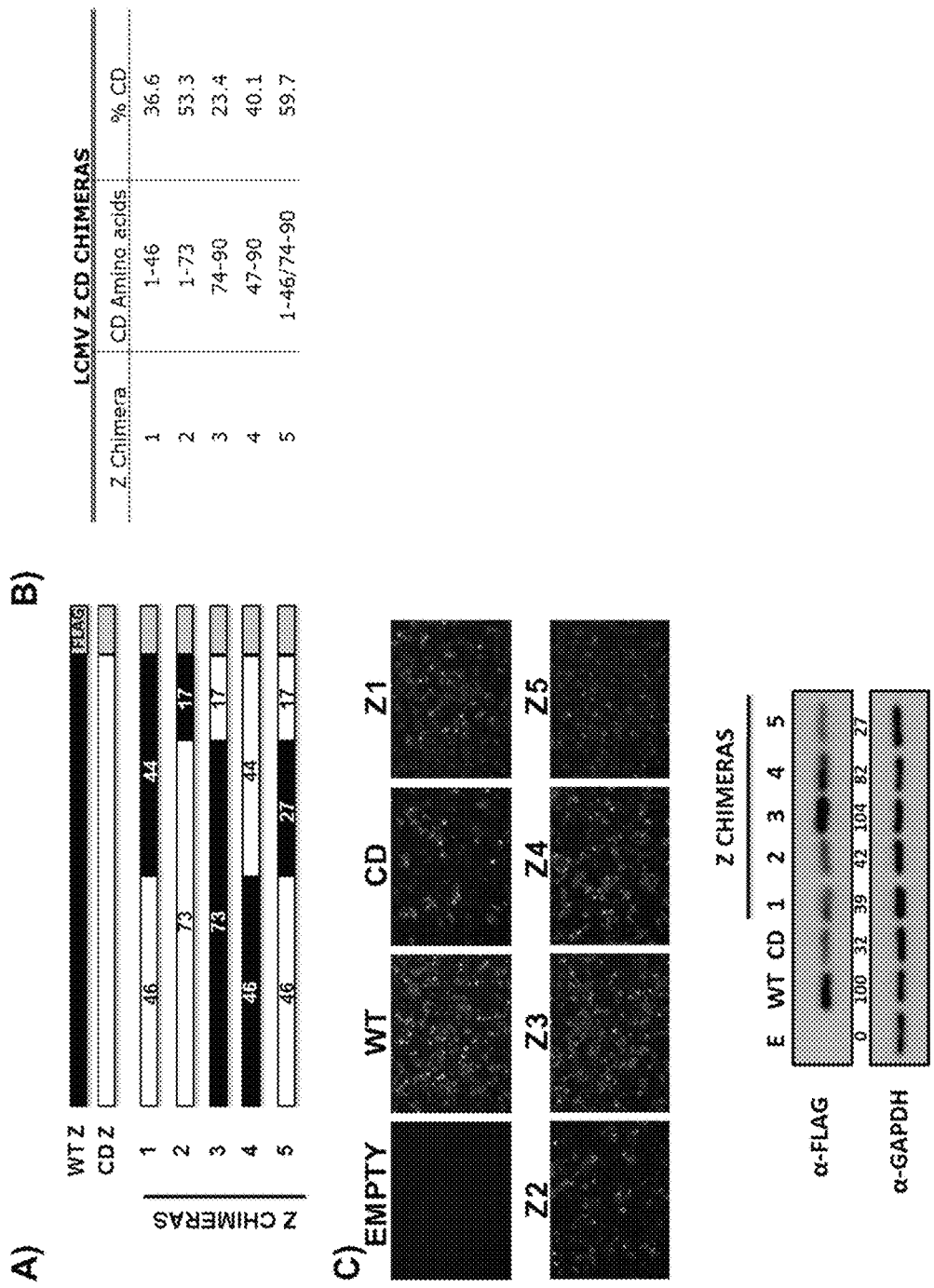
FIG. 18, comprising

Chimeras were generated between WT and Z proteins that will have different degrees of codon deoptimization using methods described in Example 1. Five chimeric Z proteins containing N-terminal, C-terminal CD sequences were generated (FIG. 18A and FIG. 18B). Protein expression of Z chimeras was assessed using immunofluorescence assay and western blot in 293T cells (FIG. 18C).

In Vitro Characterization of rLCMV/Zcd

Figure 19:
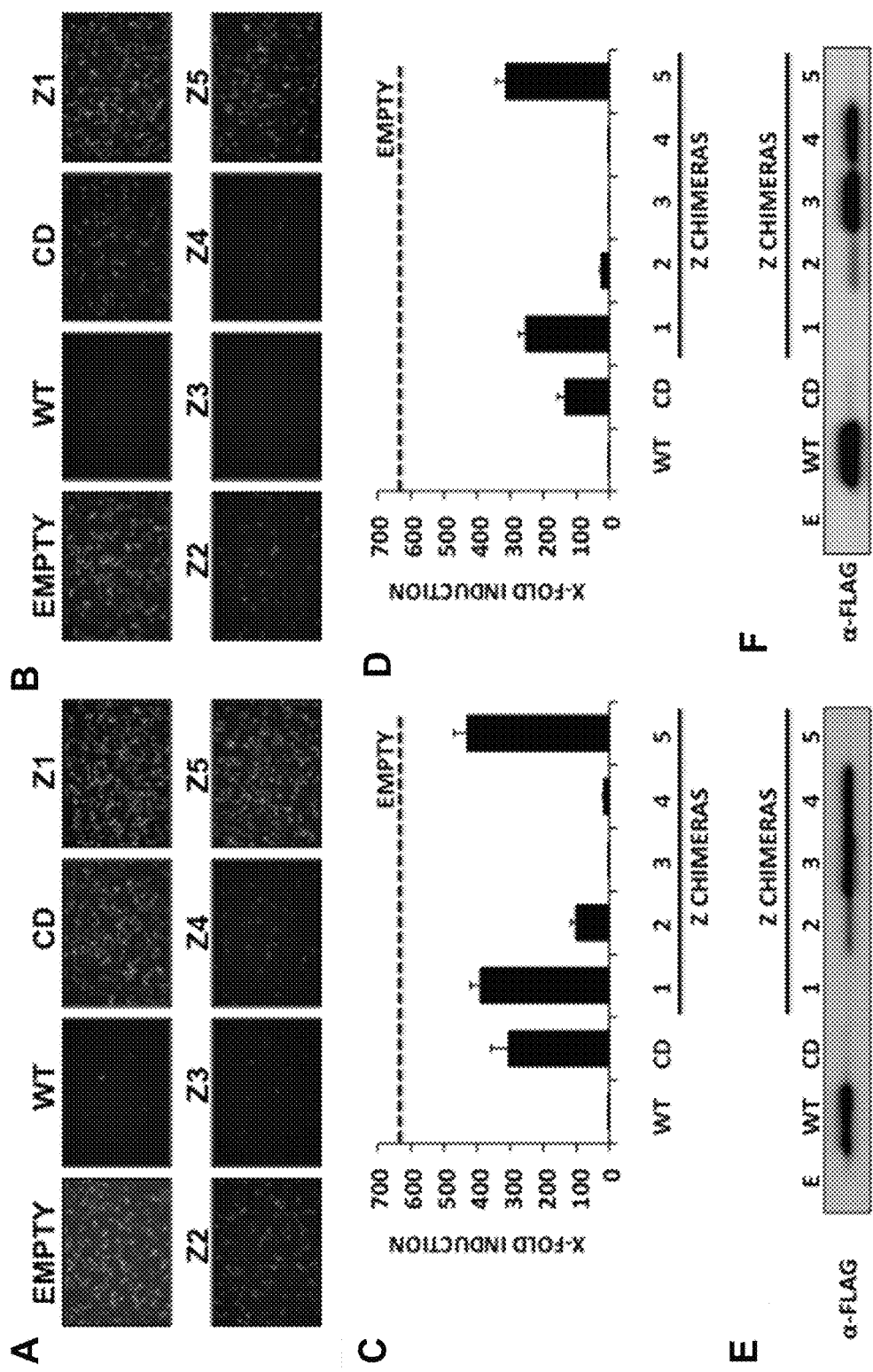
FIG. 19, comprising
Figure 20:
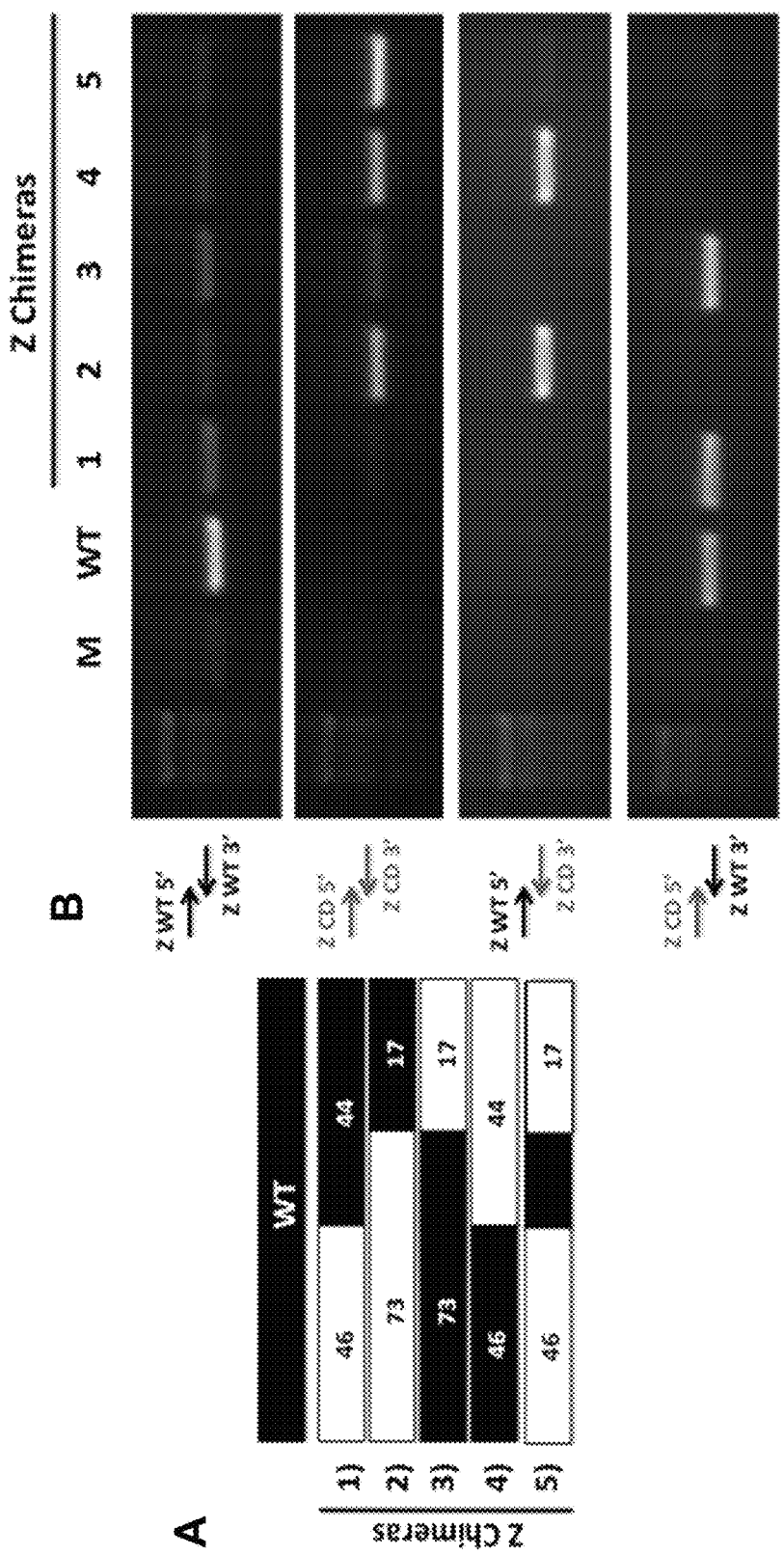
FIG. 20, comprising

Codon deoptimizated LCMV Z inhibition of viral replication and transcription were determined using a minigenome (MG) assay (FIG. 19). 293T cells were co-transfected with the vRNA expression plasmid pPOL-I LCMV GFP/Gluc (LCMV MG) and protein expression plasmids of LCMV NP, LCMV L, and either 25 ng or 50 ng of empty plasmid or the corresponding LCMV Z WT or chimeric constructs. LCMV MG expression was assessed by fluorescence microscopy (FIG. 19A and FIG. 19B) and luciferase expression (FIG. 19C and FIG. 19D). The protein expression levels of codon deoptimized Z were determined using Western blot analysis (FIG. 19E and FIG. 19F).

rLCM viruses expressing codon deoptimized Z chimeras were rescued and characterized using methods described in Example 1 (FIG. 20). The LCMV Z chimeric constructs (FIG. 20A) were confirmed using RT-PCR of LCMV/ZCD chimeric viruses (FIG. 20B).

Figure 21:
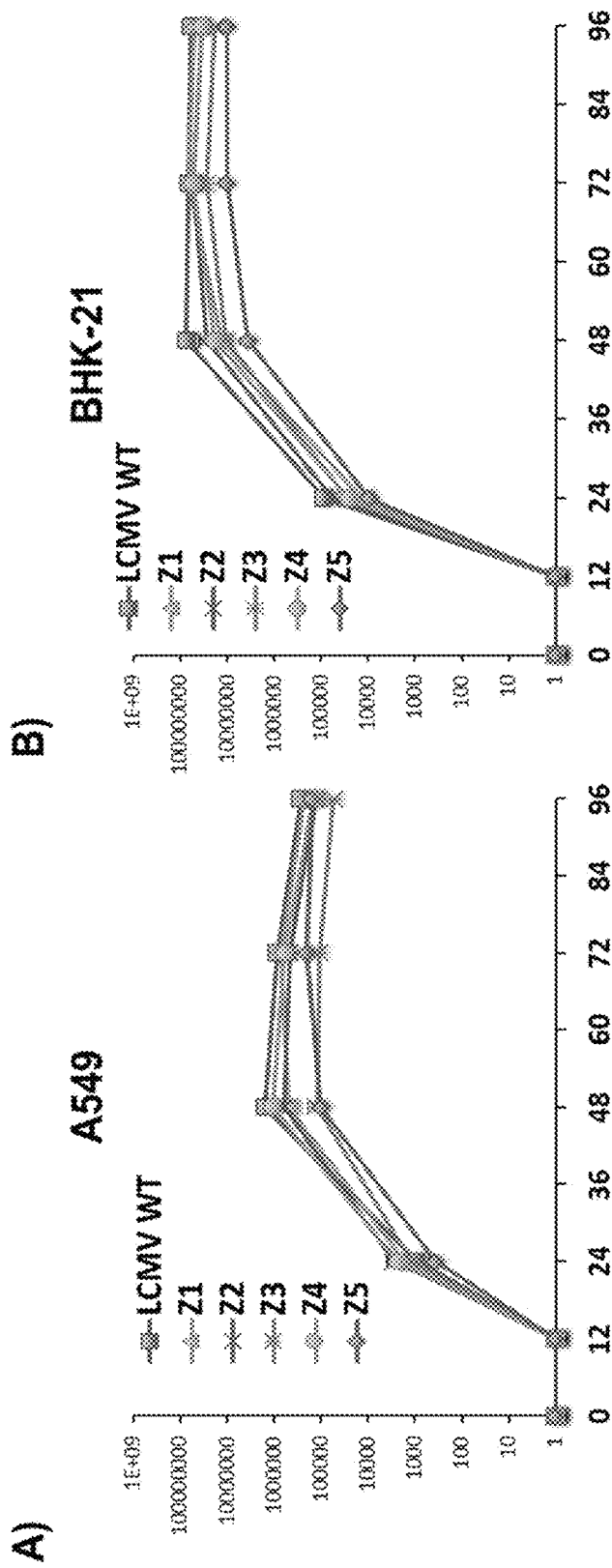
FIG. 21, comprising

The rLCMV expressing CD Z proteins were characterized by evaluating their growth kinetics in human A549 cells (FIG. 21A) and murine BHK-21 (FIG. 21B), cells. Cells were infected with rLCMV/Zed chimeras 1-5 and LCMV WT (moi 0.001). At indicated times post-infection (12, 24, 48, 71 and 96 hours) tissue culture were collected and viral titers were calculate by immunofluorescence.

Example 4: Characterization of LASV/GPcd

Figures 22C, 22D:
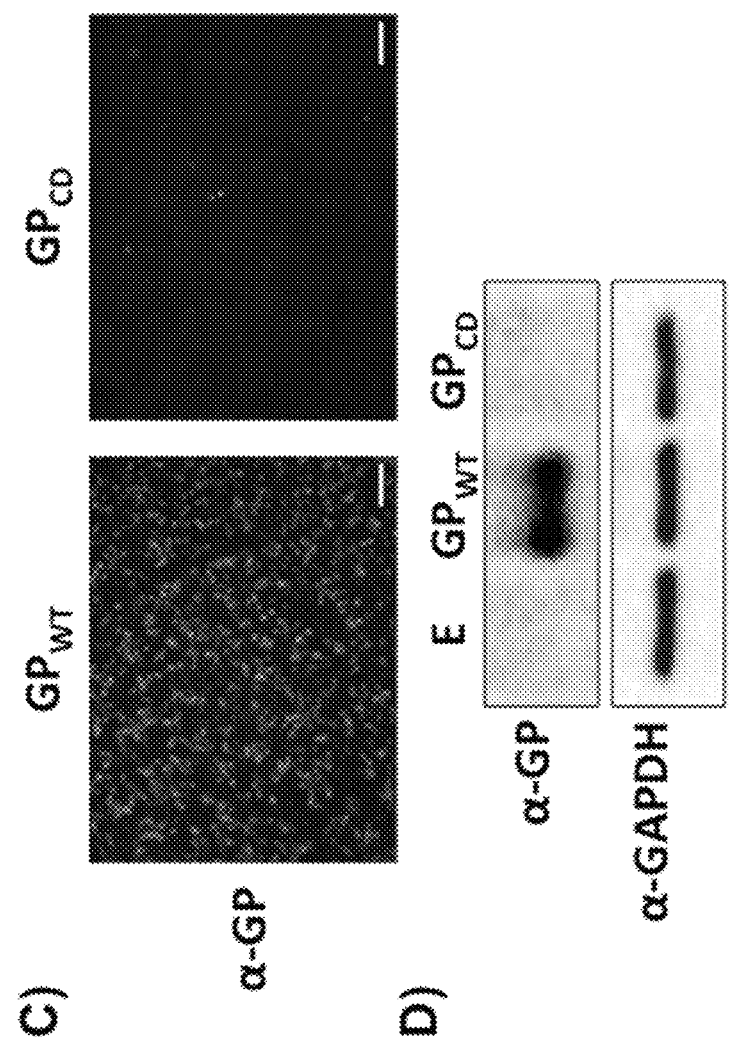

Experiments were conducted to produce and characterize codon deoptimized glycoprotein (GP) from LASV. The amino acid sequence of LASV GP is provided in FIG. 22A. The codons of the nucleic acid sequence were modified for deoptimization without affecting the amino acid sequence. The amino acids of LASV GP which were encoded by a codon that had been altered (i.e., deoptimized) are shown in grey letters. FIG. 22B provides a summary of the number of nucleotide mutations, percent of codons deoptimized, number of amino acids where the codon encoding the amino acid was mutated, and the percent of amino acids where the codon encoding the amino acid was mutated.

Experiments were conducted to examine LASV $GP_{CD}$ expression levels. Human 293T cells were transiently transfected with pCAGGS expression plasmids encoding wild-type ($GP_{WT}$) or codon deoptimized ($GP_{CD}$) LASV GP and were evaluated at 48 hours post-infection for protein expression by immunofluorescence assay (FIG. 22C) and Western blot (FIG. 22D) using the LASV GP monoclonal antibody 24.9H. It is demonstrated that the codon deoptimized LASV GP expressed less GP protein, demonstrating that codon deoptimized LASV GP can be used to effective reduce protein expression.

Example 5: Wild-Type and Codon Deoptimized Sequences

The tables provided below depict the sequences (as denoted by SEQ ID NO) for wild-type and codon deoptimized nucleotide sequences (and chimeras thereof) and amino acid sequences for LCMV NP (Table 3), LCMV Z (Table 4), and for GP of various arenaviruses (Table 5).

TABLE 3

LCMV NP

| | |
|---|---|
| Wildtype (WT) Nucleotide Sequence | SEQ ID NO: 1 |
| Codon Deoptimized (CD) Sequence | SEQ ID NO: 2 |
| WT-CD chimeras (see FIG. 2) | |
| CD1 | SEQ ID NO: 3 |
| CD2 | SEQ ID NO: 4 |
| CD3 | SEQ ID NO: 5 |
| CD4 | SEQ ID NO: 6 |
| CD5 | SEQ ID NO: 7 |
| CD6 | SEQ ID NO: 8 |
| CD7 | SEQ ID NO: 9 |
| CD8 | SEQ ID NO: 10 |
| CD9 | SEQ ID NO: 11 |
| Amino Acid Sequence | SEQ ID NO: 21 |

TABLE 4

LCMV Z

| | |
|---|---|
| Wildtype (WT) Nucleotide Sequence | SEQ ID NO: 14 |
| Codon Deoptimized (CD) Sequence | SEQ ID NO: 15 |
| WT-CD chimeras (see FIG. 18) | |
| CD1 | SEQ ID NO: 16 |
| CD2 | SEQ ID NO: 17 |
| CD3 | SEQ ID NO: 18 |
| CD4 | SEQ ID NO: 19 |
| CD5 | SEQ ID NO: 20 |
| Amino Acid Sequence | SEQ ID NO: 23 |

TABLE 5

WT and CD Glycoprotein (GP) of various arenaviruses

| | Disease | WT Nucleotide Sequence | CD Nucleotide Sequence | Amino acid sequence |
|---|---|---|---|---|
| Lymphocytic choriomeningitis virus (LCMV) - Armstrong 53b strain | Lymphocytic choriomeningitis | SEQ ID NO: 12 | SEQ ID NO: 13 | SEQ ID NO: 22 |
| Lassa virus (LASV) Josiah strain | Lassa fever | SEQ ID NO: 24 | SEQ ID NO: 25 | SEQ ID NO: 26 |
| Junin virus (JUNV) Romero strain | Argentine hemorrhagic fever | SEQ ID NO: 27 | SEQ ID NO: 28 | SEQ ID NO: 29 |
| Machupo virus (MACV) Carvallo Strain | Bolivian hemorrhagic fever | SEQ ID NO: 30 | SEQ ID NO: 31 | SEQ ID NO: 32 |
| Sabia virus (SABV) SPH114201 strain | Brazilian hemorrhagic fever | SEQ ID NO: 33 | SEQ ID NO: 34 | SEQ ID NO: 35 |
| Guanarito virus (GTOV) AV 97021119 strain | Venezuelan hemorrhagic fever | SEQ ID NO: 36 | SEQ ID NO: 37 | SEQ ID NO: 38 |
| Chapare virus (CHPV) 810419 strain | Chapare hemorrhagic fever | SEQ ID NO: 39 | SEQ ID NO: 40 | SEQ ID NO: 41 |
| Ocozocoautla de Espinosa virus (OCEV) AV B1030026 strain | Hemorrhagic fever in Southern Mexico | SEQ ID NO: 42 | SEQ ID NO: 43 | SEQ ID NO: 44 |
| Whitewater Arroyo virus (WWAV) Strain AV 9310135 | Hemorrhagic fever in Southwestern USA | SEQ ID NO: 45 | SEQ ID NO: 46 | SEQ ID NO: 47 |
| Lujo virus (LUJV) Strain 649188 | Lujo hemorrhagic fever | SEQ ID NO: 48 | SEQ ID NO: 49 | SEQ ID NO: 50 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunological composition comprising a live-attenuated virus (LAV), wherein the LAV is a codon deoptimized (CD) arenavirus comprised of at least one CD polynucleotide encoding at least one protein selected from the group consisting of viral nucleoprotein (NP), glycoprotein precursor (GPC), matrix (Z) protein, and combinations thereof,
wherein the at least one CD polynucleotide comprises a nucleic acid sequence at least 98% homologous to a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, SEQ ID NO: 13, SEQ ID NO:15, SEQ ID NO: 16, SEQ ID NO: 17, SEQ ID NO: 18, SEQ ID NO: 19, SEQ ID NO: 20, and SEQ ID NO: 25.

2. The composition of claim 1, wherein the at least one CD polynucleotide comprises a nucleic acid sequence selected from the group consisting of SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

3. The composition of claim 1, wherein the at least one CD polynucleotide comprises a nucleic acid sequence selected from the group consisting of SEQ ID NO: 13, and SEQ ID NO: 25.

4. The composition of claim 1, wherein the at least one CD polynucleotide comprises a nucleic acid sequence selected from the group consisting of SEQ ID NO: 15, SEQ ID NO: 16, SEQ ID NO: 17, SEQ ID NO: 18, SEQ ID NO: 19, and SEQ ID NO: 20.

* * * * *

SEQUENCE LISTING

<160> NUMBER OF SEQ ID NOS: 50

<210> SEQ ID NO 1
<211> LENGTH: 1677
<212> TYPE: DNA
<213> ORGANISM: Lymphocytic choriomeningitis virus

<400> SEQUENCE: 1

```
atgtccttgt ctaaggaagt taagagcttc caatggacgc aagcattgag aagagaattg      60
cagagcttca catcagatgt gaaggctgct gtcattaagg atgcaaccaa ccttctgaat     120
gggttggact tctctgaggt cagcaatgtt cagaggatca tgaggaagga aaagagagat     180
gacaaagacc tacagagact cagaagtctc aaccagactg tacattctct tgtggattta     240
aagtcaacat caaagaagaa tgttttgaaa gtggggaggc tcagtgcaga agaactgatg     300
```

```
tctcttgcgg ctgaccttga gaagctgaag gccaagatca tgaggtctga aaggccccag    360
gcttcagggg tatatatggg gaacttaaca acacagcaac tagaccaaag atctcagatc    420
ctacagatag ttgggatgag aaagcctcag cagggtgcaa gtggtgtggt aagagtttgg    480
gatgtgaaag actcatcact tttgaacaat caatttggca caatgccaag tctaactatg    540
gcttgtatgg ccaaacagtc acagactccg ctcaatgacg ttgtacaagc gctcacagac    600
cttggcttgc tttacacagt caagtatcca aatcttaatg atcttgaaag gctgaaagac    660
aagcacccag ttctgggggt catcactgaa cagcagtcca gcatcaacat ttctggctat    720
aactttagtc ttggtgctgc cgtgaaggca ggggcagccc tgttggatgg gggtaacatg    780
ttagagtcaa ttttgatcaa gccaagcaac agcgaggacc tcttgaaggc agttctcggg    840
gccaagagaa aactcaacat gtttgtttca gaccaagttg gggacaggaa cccttatgaa    900
aacatcctct ataaagtttg cctttcaggt gaaggatggc catacatagc ttgtagaaca    960
tcgattgtgg ggagagcatg ggaaaacaca acaattgatc tcacaagcga gaaacctgca   1020
gtcaactcac ccaggccagc gcctggagca gcaggtccac ctcaggtggg cttaagctac   1080
agccagacaa tgcttttaaa agacctcatg ggaggaattg accccaacgc tcctacatgg   1140
attgacattg agggtagatt taatgatcca gtggaaatag caattttcca accacagaac   1200
gggcagttca tacacttta cagggaaccc gttgatcaaa acaattcaa gcaagattcc    1260
aagtactcac acggcatgga tcttgccgac ctcttcaatg cgcaacccgg ttgacctcg    1320
tcagttatag gtgctcttcc gcaggggatg gttctaagct gtcaaggctc cgatgacatc   1380
agaaagcttc tggactcaca gaataggaag gacattaagc ttatcgatgt tgaaatgacc   1440
agggaagctt cgagggagta tgaagacaaa gtgtgggaca aatatggctg gttgtgtaag   1500
atgcatactg gaatagtaag ggacaaaaag aagaaagaga tcaccccgca ctgtgcactc   1560
atggactgca tcattttga aagcgcctcc aaagcaaggc tcccagatct gaaaactgtt   1620
cacaacattc tgccacatga cctaattttt agaggcccaa atgttgtgac actctaa     1677
```

<210> SEQ ID NO 2
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 2

```
atgtcgttat cgaaagaagt aaaatcgttt caatggacgc aagcgttacg tcgtgaatta     60
caatcgttta cgtcggatgt aaaagcggcg gtaataaaag atgcgacgaa tttattaaat    120
ggtttagatt tttcggaagt atcgaatgta caacgtataa tgcgtaaaga aaaacgtgat    180
gataaagatt tacaacgttt acgttcgtta aatcaaacgg tacattcgtt agtagattta    240
aaatcgacgc gaaaaaaaa tgtattaaaa gtaggtcgtt tatcggcgga agaattaatg    300
tcgttagcgg cggatttaga aaaattaaaa gcgaaaataa tgcgttcgga acgtccgcaa    360
gcgtcgggtg tatatatggg taatttaacg acgcaacaat tagatcaacg ttcgcaaata    420
ttacaaatag taggtatgcg taaaccgcaa caaggtgcgt cgggtgtagt acgtgtatgg    480
gatgtaaaag attcgtcgtt attaaataat caatttggta cgatgccgtc gttaacgatg    540
gcgtgtatgg cgaaacaatc gcaaacgccg ttaatgatgt tagtacaagc gttaacggat    600
ttaggtttat tatatacggt aaaatatccg aatttaaatg atttagaacg tttaaaagat    660
aaacatccgg tattaggtgt aataacggaa cagcaatcgt cgataaatat atcgggttat    720
```

-continued

```
aattttttcgt taggtgcggc ggtaaaagcg ggtgcggcgt tattagatgg tggtaatatg      780
ttagaatcga tattaataaa accgtcgaat tcggaagatt tattaaaagc ggtattaggt      840
gcgaaacgta aattaaatat gtttgtatcg gatcaagtag gtgatcgtaa tccgtatgaa      900
aatatattat ataaagtatg tttatcgggt gaaggttggc cgtatatagc gtgtcgtacg      960
tcgatagtag gtcgtgcgtg ggaaaatacg acgatagatt taacgtcgga aaaaccggcg     1020
gtaaattcgc cgcgtccggc gccgggtgcg gcgggtccgc cgcaagtagg tttatcgtat     1080
tcgcaaacga tgttattaaa agatttaatg ggtggtatag atccgaatgc gccgacgtgg     1140
atagatatag aaggtcgttt taatgatccg gtagaaatag cgatatttca accgcaaaat     1200
ggtcaattta tacattttta tcgtgaaccg gtagatcaaa aacaatttaa acaagattcg     1260
aaatattcgc atggtatgga tttagcggat ttatttaatg cgcaaccggg tttaacgtcg     1320
tcggtaatag gtgcgttacc gcaaggtatg gtattatcgt gtcaaggttc ggatgatata     1380
cgtaaattat tagattcgca aaatcgtaaa gatataaaat taatagatgt agaaatgacg     1440
cgtgaagcgt cgcgtgaata tgaagataaa gtatgggata aatatggttg gttatgtaaa     1500
atgcatacgg gtatagtacg tgataaaaaa aaaaagaaa taacgccgca ttgtgcgtta     1560
atggattgta taatatttga atcggcgtcg aaagcgcgtt taccggattt aaaaacggta     1620
cataatatat taccgcatga tttaatattt cgtggtccga atgtagtaac gttataa      1677
```

<210> SEQ ID NO 3
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 3

```
atgtcgttat cgaaagaagt aaaatcgttt caatggacgc aagcgttacg tcgtgaatta       60
caatcgttta cgtcggatgt aaaagcggcg gtaataaaag atgcgacgaa tttattaaat      120
ggtttagatt tttcggaagt atcgaatgta caacgtataa tgcgtaaaga aaaacgtgat      180
gataaagatt tacaacgttt acgttcgtta aatcaaacgg tacattcgtt agtagattta      240
aaatcgacgt cgaaaaaaaa tgtattaaaa gtaggtcgtt tatcggcgga agaattaatg      300
tcgttagcgg cggatttaga aaaattaaaa gcgaaaataa tgcgttcgga acgtccgcaa      360
gcgtcgggtg tatatatggg taatttaacg acgcaacaat tagatcaacg ttcgcaaata      420
ttacaaatag taggtatgcg taaaccgcaa caaggtgcgt cgggtgtagt acgtgtatgg      480
gatgtaaaag attcgtcgtt attaaataat caatttggta cgatgccgtc gttaacgatg      540
gcgtgtatgg cgaaacaatc gcaaacgccg ttaaatgatg tagtacaagc gttaacggat      600
ttaggtttat tatatacggt aaaatatccg aatcttaatg atcttgaaag gctgaaagac      660
aagcacccag ttctggggt catcactgaa cagcagtcca gcatcaacat ttctggctat      720
aactttagtc ttggtgctgc cgtgaaggca ggggcagccc tgttggatgg gggtaacatg      780
ttagagtcaa ttttgatcaa gccaagcaac agcgaggacc tcttgaaggc agttctcggg      840
gccaagagaa aactcaacat gtttgtttca gaccaagttg gggacaggaa cccttatgaa      900
aacatcctct ataaagtttg cctttcaggt gaaggatggc catacatagc ttgtagaaca      960
tcgattgtgg ggagagcatg gaaaacacac acaattgatc tcacaagcga gaaacctgca     1020
gtcaactcac ccaggccagc gcctggagca gcaggtccac ctcaggtggg cttaagctac     1080
```

| | | | |
|---|---|---|---|
| agccagacaa | tgcttttaaa | agacctcatg | ggaggaattg acccaacgc tcctacatgg | 1140 |
| attgacattg | agggtagatt | taatgatcca | gtggaaatag caattttcca accacagaac | 1200 |
| gggcagttca | tacactttta | cagggaaccc | gttgatcaaa acaattcaa gcaagattcc | 1260 |
| aagtactcac | acggcatgga | tcttgccgac | ctcttcaatg cgcaaccgg gttgacctcg | 1320 |
| tcagttatag | gtgctcttcc | gcaggggatg | ttctaagct gtcaaggctc cgatgacatc | 1380 |
| agaaagcttc | tggactcaca | gaataggaag | gacattaagc ttatcgatgt tgaaatgacc | 1440 |
| agggaagctt | cgagggagta | tgaagacaaa | gtgtgggaca aatatggctg gttgtgtaag | 1500 |
| atgcatactg | gaatagtaag | ggacaaaaag | aagaaagaga tcaccccgca ctgtgcactc | 1560 |
| atggactgca | tcattttga | aagcgcctcc | aaagcaaggc tcccagatct gaaaactgtt | 1620 |
| cacaacattc | tgccacatga | cctaattttt | agaggcccaa atgttgtgac actctaa | 1677 |

<210> SEQ ID NO 4
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 4

| | | | |
|---|---|---|---|
| atgtcgttat | cgaaagaagt | aaaatcgttt | caatggacgc aagcgttacg tcgtgaatta | 60 |
| caatcgttta | cgtcggatgt | aaaagcggcg | gtaataaaag atgcgacgaa tttattaaat | 120 |
| ggtttagatt | tttcggaagt | atcgaatgta | caacgtataa tgcgtaaaga aaaacgtgat | 180 |
| gataaagatt | tacaacgttt | acgttcgtta | aatcaaacgg tacattcgtt agtagattta | 240 |
| aaatcgacgt | cgaaaaaaaa | tgtattaaaa | gtaggtcgtt tatcggcgga agaattaatg | 300 |
| tcgttagcgg | cggatttaga | aaaattaaaa | gcgaaaataa tgcgttcgga acgtccgcaa | 360 |
| gcgtcgggtg | tatatatggg | taatttaacg | acgcaacaat tagatcaacg ttcgcaaata | 420 |
| ttacaaatag | taggtatgcg | taaaccgcaa | caaggtgcgt cgggtgtagt acgtgtatgg | 480 |
| gatgtaaaag | attcgtcgtt | attaaataat | caatttggta cgatgccgtc gttaacgatg | 540 |
| gcgtgtatgc | gaaacaatc | gcaaacgccg | ttaaatgatg tagtacaagc gttaacggat | 600 |
| ttaggtttat | tatatacggt | aaaatatccg | aatttaaatg atttagaacg tttaaaagat | 660 |
| aaacatccgg | tattaggtgt | aataacgaaa | cagcaatcgt cgataaatat atcgggttat | 720 |
| aattttcgt | taggtgcggc | ggtaaaagcg | ggtgcggcgt tattagatgg tggtaatatg | 780 |
| ttagaatcga | tattaataaa | accgagcaac | agcgaggacc tcttgaaggc agttctcggg | 840 |
| gccaagagaa | aactcaacat | gtttgtttca | gaccaagttg gggacaggaa cccttatgaa | 900 |
| aacatcctct | ataagtttg | cctttcaggt | gaaggatggc catacatagc ttgtagaaca | 960 |
| tcgattgtgg | ggagagcatg | ggaaaacaca | acaattgatc tcacaagcga gaaacctgca | 1020 |
| gtcaactcac | ccaggccagc | gcctggagca | gcaggtccac ctcaggtggg cttaagctac | 1080 |
| agccagacaa | tgcttttaaa | agacctcatg | ggaggaattg acccaacgc tcctacatgg | 1140 |
| attgacattg | agggtagatt | taatgatcca | gtggaaatag caattttcca accacagaac | 1200 |
| gggcagttca | tacactttta | cagggaaccc | gttgatcaaa acaattcaa gcaagattcc | 1260 |
| aagtactcac | acggcatgga | tcttgccgac | ctcttcaatg cgcaaccgg gttgacctcg | 1320 |
| tcagttatag | gtgctcttcc | gcaggggatg | ttctaagct gtcaaggctc cgatgacatc | 1380 |
| agaaagcttc | tggactcaca | gaataggaag | gacattaagc ttatcgatgt tgaaatgacc | 1440 |
| agggaagctt | cgagggagta | tgaagacaaa | gtgtgggaca aatatggctg gttgtgtaag | 1500 | atgcatactg gaatagtaag ggacaaaaag aagaaagaga tcaccccgca ctgtgcactc    1560 atggactgca tcattttttga aagcgcctcc aaagcaaggc tcccagatct gaaaactgtt    1620 cacaacattc tgccacatga cctaattttt agaggcccaa atgttgtgac actctaa       1677

<210> SEQ ID NO 5
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 5
atgtcgttat cgaaagaagt aaaatcgttt caatggacgc aagcgttacg tcgtgaatta      60
caatcgttta cgtcggatgt aaaagcggcg gtaataaaag atgcgacgaa tttattaaat     120
ggtttagatt tttcggaagt atcgaatgta caacgtataa tgcgtaaaga aaaacgtgat     180
gataaagatt tacaacgttt acgttcgtta aatcaaacgg tacattcgtt agtagattta     240
aaatcgacgt cgaaaaaaaa tgtattaaaa gtaggtcgtt tatcggcgga agaattaatg     300
tcgttagcgg cggatttaga aaaattaaaa gcgaaaataa tgcgttcgga acgtccgcaa     360
gcgtcgggtg tatatatggg taatttaacg acgcaacaat tagatcaacg ttcgcaaata     420
ttacaaatag taggtatgcg taaaccgcaa caaggtgcgt cgggtgtagt acgtgtatgg     480
gatgtaaaag attcgtcgtt attaaataat caatttggta cgatgccgtc gttaacgatg     540
gcgtgtatgg cgaaacaatc gcaaacgccg ttaaatgatg tagtacaagc gttaacggat     600
ttaggtttat tatatacggt aaaaatatccg aatttaaatg atttagaacg tttaaaagat     660
aaacatccgg tattaggtgt aataacggaa cagcaatcgt cgataaatat atcgggttat     720 aattttttcgt taggtgcggc ggtaaaagcg ggtgcggcgt tattagatgg tggtaatatg     780
ttagaatcga tattaataaa accgtcgaat tcggaagatt tattaaaagc ggtattaggt     840
gcgaaacgta aattaaatat gtttgtatcg gatcaagtag gtgatcgtaa tccgtatgaa     900
aatatatatt ataaagtatg tttatcgggt gaaggttggc cgtatatagc gtgtcgtacg     960
tcgatagtag gtcgtgcgtg ggaaaatacg acgatagatt taacgtcgga aaaaccggcg    1020
gtaaattcgc cgcgtccggc gccgggtgcg gcgggtccgc cgcaagtagg tttatcgtat    1080
tcgcaaacga tgttattaaa agatttaatg ggtggtatag atccgaatgc gccgacgtgg    1140
atagatatag aaggtcgttt taatgatccg gtagaaatag cgatatttca accgcaaaat    1200
ggtcaattta tacattttta tcgtgaaccg gtagatcaaa aacaatttaa acaagattcc    1260
aagtactcac acggcatgga tcttgccgac ctcttcaatg cgcaacccgg gttgacctcg    1320
tcagttatag gtgctcttcc gcaggggatg gttctaagct gtcaaggctc cgatgacatc    1380
agaaagcttc tggactcaca gaataggaag gacattaagc ttatcgatgt tgaaatgacc    1440
agggaagctt cgagggagta tgaagacaaa gtgtgggaca aatatggctg gttgtgtaag    1500
atgcatactg gaatagtaag ggacaaaaag aagaaagaga tcaccccgca ctgtgcactc    1560
atggactgca tcattttttga aagcgcctcc aaagcaaggc tcccagatct gaaaactgtt    1620
cacaacattc tgccacatga cctaattttt agaggcccaa atgttgtgac actctaa       1677

<210> SEQ ID NO 6
<211> LENGTH: 1677
<212> TYPE: DNA
<213> ORGANISM: Artificial Sequence
<220> FEATURE:

<223> OTHER INFORMATION: Chemically synthesized

<400> SEQUENCE: 6

```
atgtccttgt ctaaggaagt taagagcttc caatggacgc aagcattgag aagagaattg      60
cagagcttca catcagatgt gaaggctgct gtcattaagg atgcaaccaa ccttctgaat     120
gggttggact tctctgaggt cagcaatgtt cagaggatca tgaggaagga aaagagagat     180
gacaaagacc tacagagact cagaagtctc aaccagactg tacattctct tgtggattta     240
aagtcaacat caaagaagaa tgttttgaaa gtggggaggc tcagtgcaga agaactgatg     300
tctcttgcgg ctgaccttga aagctgaag gccaagatca tgaggtctga aaggccccag      360
gcttcagggg tatatatggg aacttaaca acacagcaac tagaccaaag atctcagatc      420
ctacagatag ttgggatgag aaagcctcag caggggtgcaa gtggtgtggt aagagtttgg    480
gatgtgaaag actcatcact tttgaacaat caatttggca caatgccaag tctaactatg    540
gcttgtatgg ccaaacagtc acagactccg ctcaatgacg ttgtacaagc gctcacagac    600
cttggcttgc tttacacagt caagtatcca atcttaatg atcttgaaag gctgaaagac     660
aagcacccag ttctgggggt catcactgaa cagcagtcca gcatcaacat ttctggctat    720
aactttagtc ttggtgctgc cgtgaaggca ggggcagccc tgttggatgg gggtaacatg    780
ttagagtcaa ttttgatcaa gccaagcaac agcgaggacc tcttgaaggc agttctcggg    840
gccaagagaa aactcaacat gtttgtttca gaccaagttg gggacaggaa cccttatgaa    900
acatcctct ataaagtttg cctttcaggt gaaggatggc catacatagc ttgtagaaca     960
tcgattgtgg ggagagcatg ggaaaacaca acaattgatc tcacaagcga gaaacctgca   1020
gtcaactcac ccaggccagc gcctggagca gcaggtccac ctcaggtggg cttaagctac   1080
agccagacaa tgctttttaaa agacctcatg ggaggaattg accccaacgc tcctacatgg   1140
attgacattg agggtagatt taatgatcca gtggaaatag caattttcca accacagaac   1200
gggcagttca tacactttta cagggaaccc gttgatcaaa acaattcaa gcaagattcg     1260
aaatattcgc atggtatgga tttagcggat ttatttaatg cgcaaccggg tttaacgtcg    1320
tcggtaatag gtgcgttacc gcaaggtatg gtattatcgt gtcaaggttc ggatgatata   1380
cgtaaattat tagattcgca aaatcgtaaa gatataaaat taatagatgt agaaatgacg   1440
cgtgaagcgt cgcgtgaata tgaagataaa gtatgggata aatatggttg gttatgtaaa   1500
atgcatacgg gtatagtacg tgataaaaaa aaaaaagaaa taacgccgca ttgtgcgtta   1560
atggattgta taatatttga atcggcgtcg aaagcgcgtt taccggattt aaaaacggta   1620
cataatatat taccgcatga tttaatattt cgtggtccga atgtagtaac gttataa      1677
```

<210> SEQ ID NO 7
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 7

```
atgtccttgt ctaaggaagt taagagcttc caatggacgc aagcattgag aagagaattg      60
cagagcttca catcagatgt gaaggctgct gtcattaagg atgcaaccaa ccttctgaat     120
gggttggact tctctgaggt cagcaatgtt cagaggatca tgaggaagga aaagagagat     180
gacaaagacc tacagagact cagaagtctc aaccagactg tacattctct tgtggattta     240
aagtcaacat caaagaagaa tgttttgaaa gtggggaggc tcagtgcaga agaactgatg     300
```

```
tctcttgcgg ctgaccttga gaagctgaag gccaagatca tgaggtctga aggccccag    360 gcttcagggg tatatatggg gaacttaaca acacagcaac tagaccaaag atctcagatc   420
ctacagatag ttgggatgag aaagcctcag cagggtgcaa gtggtgtggt aagagtttgg   480
gatgtgaaag actcatcact tttgaacaat caatttggca caatgccaag tctaactatg   540
gcttgtatgg ccaaacagtc acagactccg ctcaatgacg ttgtacaagc gctcacagac   600
cttggcttgc tttacacagt caagtatcca aatcttaatg atcttgaaag gctgaaagac   660
aagcacccag ttctgggggt catcactgaa cagcagtcca gcatcaacat ttctggctat   720
aactttagtc ttggtgctgc cgtgaaggca ggggcagccc tgttggatgg gggtaacatg   780
ttagagtcaa ttttgatcaa gccaagcaat tcggaagatt tattaaaagc ggtattaggt   840
gcgaaacgta aattaaatat gtttgtatcg atcaagtag gtgatcgtaa tccgtatgaa    900
aatatattat ataaagtatg tttatcgggt gaaggttggc cgtatatagc gtgtcgtacg   960
tcgatagtag gtcgtgcgtg ggaaaatacg acgatagatt taacgtcgga aaaaccggcg  1020
gtaaattcgc cgcgtccggc gccgggtgcg gcgggtccgc cgcaagtagg tttatcgtat  1080
tcgcaaacga tgttattaaa agatttaatg ggtggtatag atccgaatgc gccgacgtgg  1140
atagatatag aaggtcgttt taatgatccg gtagaaatag cgatatttca accgcaaaat  1200
ggtcaattta tacattttta tcgtgaaccg gtagatcaaa aacaatttaa acaagattcg  1260
aaatattcgc atggtatgga tttagcggat ttatttaatg cgcaaccggg tttaacgtcg  1320
tcggtaatag gtgcgttacc gcaaggtatg gtattatcgt gtcaaggttc ggatgatata  1380
cgtaaattat tagattcgca aaatcgtaaa gatataaaat taatagatgt agaaatgacg  1440
cgtgaagcgt cgcgtgaata tgaagataaa gtatgggata aatatggttg gttatgtaaa  1500
atgcatacgg gtatagtacg tgataaaaaa aaaaagaaa taacgccgca ttgtgcgtta   1560
atggattgta taatatttga atcggcgtcg aaagcgcgtt taccggattt aaaaacggta  1620
cataatatat taccgcatga tttaatattt cgtggtccga atgtagtaac gttataa     1677
```

<210> SEQ ID NO 8
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 8

```
atgtccttgt ctaaggaagt taagagcttc caatggacgc aagcattgag aagagaattg     60
cagagcttca catcagatgt gaaggctgct gtcattaagg atgcaaccaa ccttctgaat    120
gggttggact ctctgaggt cagcaatgtt cagaggatca tgaggaagga aaagagagat    180
gacaaagacc tacagagact cagaagtctc aaccagactg tacattctct tgtggattta   240
aagtcaacat caaagaagaa tgttttgaaa gtggggaggc tcagtgcaga gaactgatg    300 tctcttgcgg ctgaccttga gaagctgaag gccaagatca tgaggtctga aggccccag    360 gcttcagggg tatatatggg gaacttaaca acacagcaac tagaccaaag atctcagatc   420
ctacagatag ttgggatgag aaagcctcag cagggtgcaa gtggtgtggt aagagtttgg   480
gatgtgaaag actcatcact tttgaacaat caatttggca caatgccaag tctaactatg   540
gcttgtatgg ccaaacagtc acagactccg ctcaatgacg ttgtacaagc gctcacagac   600
cttggcttgc tttacacagt caagtatcca aatttaaatg atttagaacg tttaaaagat   660
```

| | |
|---|---|
| aaacatccgg tattaggtgt aataacggaa cagcaatcgt cgataaatat atcgggttat | 720 |
| aattttcgt taggtgcggc ggtaaaagcg ggtgcggcgt tattagatgg tggtaatatg | 780 |
| ttagaatcga tattaataaa accgtcgaat tcggaagatt tattaaaagc ggtattaggt | 840 |
| gcgaaacgta aattaaatat gtttgtatcg gatcaagtag gtgatcgtaa tccgtatgaa | 900 |
| aatatattat ataaagtatg tttatcgggt gaaggttggc cgtatatagc gtgtcgtacg | 960 |
| tcgatagtag gtcgtgcgtg ggaaaatacg acgatagatt taacgtcgga aaaaccggcg | 1020 |
| gtaaattcgc cgcgtccggc gccgggtgcg gcgggtccgc cgcaagtagg tttatcgtat | 1080 |
| tcgcaaacga tgttattaaa agatttaatg ggtggtatag atccgaatgc gccgacgtgg | 1140 |
| atagatatag aaggtcgttt taatgatccg gtagaaatag cgatatttca accgcaaaat | 1200 |
| ggtcaattta tacattttta tcgtgaaccg gtagatcaaa aacaatttaa acaagattcg | 1260 |
| aaatattcgc atggtatgga tttagcggat ttatttaatg cgcaaccggg tttaacgtcg | 1320 |
| tcggtaatag gtgcgttacc gcaaggtatg gtattatcgt gtcaaggttc ggatgatata | 1380 |
| cgtaaattat tagattcgca aaatcgtaaa gatataaaat taatagatgt agaaatgacg | 1440 |
| cgtgaagcgt cgcgtgaata tgaagataaa gtatgggata aatatggttg gttatgtaaa | 1500 |
| atgcatacgg gtatagtacg tgataaaaaa aaaaagaaa taacgccgca ttgtgcgtta | 1560 |
| atggattgta taatatttga atcggcgtcg aaagcgcgtt taccggattt aaaaacggta | 1620 |
| cataatatat taccgcatga tttaatattt cgtggtccga atgtagtaac gttataa | 1677 |

<210> SEQ ID NO 9
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 9

| | |
|---|---|
| atgtccttgt ctaaggaagt taagagcttc caatggacgc aagcattgag aagagaattg | 60 |
| cagagcttca catcagatgt gaaggctgct gtcattaagg atgcaaccaa ccttctgaat | 120 |
| gggttggact tctctgaggt cagcaatgtt cagaggatca tgaggaagga aaagagagat | 180 |
| gacaaagacc tacagagact cagaagtctc aaccagactg tacattctct tgtggattta | 240 |
| aagtcaacat caaagaagaa tgttttgaaa gtggggaggc tcagtgcaga gaactgatg | 300 |
| tctcttgcgg ctgaccttga gaagctgaag gccaagatca tgaggtctga aaggccccag | 360 |
| gcttcagggg tatatatggg gaacttaaca acacagcaac tagaccaaag atctcagatc | 420 |
| ctacagatag ttgggatgag aaagcctcag cagggtgcaa gtggtgtggt aagagtttgg | 480 |
| gatgtgaaag actcatcact tttgaacaat caatttggca aatgccaag tctaactatg | 540 |
| gcttgtatgg ccaaacagtc acagactccg ctcaatgacg ttgtacaagc gctcacagac | 600 |
| cttggcttgc tttacacagt caagtatcca aatttaaatg atttagaacg tttaaaagat | 660 |
| aaacatccgg tattaggtgt aataacggaa cagcaatcgt cgataaatat atcgggttat | 720 |
| aattttcgt taggtgcggc ggtaaaagcg ggtgcggcgt tattagatgg tggtaatatg | 780 |
| ttagaatcga tattaataaa accgagcaac agcgaggacc tcttgaaggc agttctcggg | 840 |
| gccaagagaa aactcaacat gtttgtttca gaccaagttg gggacaggaa ccctttatgaa | 900 |
| aacatcctct ataaagtttg cctttcaggt gaaggatggc catacatagc ttgtagaaca | 960 |
| tcgattgtgg ggagagcatg ggaaaacaca acaattgatc tcacaagcga gaaacctgca | 1020 |
| gtcaactcac ccaggccagc gcctggagca gcaggtccac ctcaggtggg cttaagctac | 1080 |

| | |
|---|---|
| agccagacaa tgcttttaaa agacctcatg ggaggaattg accccaacgc tcctacatgg | 1140 |
| attgacattg agggtagatt taatgatcca gtggaaatag caattttcca accacagaac | 1200 |
| gggcagttca tacactttta cagggaaccc gttgatcaaa acaattcaa gcaagattcc | 1260 |
| aagtactcac acggcatgga tcttgccgac ctcttcaatg cgcaacccgg ttgacctcg | 1320 |
| tcagttatag gtgctcttcc gcaggggatg gttctaagct gtcaaggctc cgatgacatc | 1380 |
| agaaagcttc tggactcaca gaataggaag gacattaagc ttatcgatgt tgaaatgacc | 1440 |
| agggaagctt cgagggagta tgaagacaaa gtgtgggaca aatatggctg gttgtgtaag | 1500 |
| atgcatactg gaatagtaag ggacaaaaag aagaaagaga tcaccccgca ctgtgcactc | 1560 |
| atggactgca tcattttga aagcgcctcc aaagcaaggc tcccagatct gaaaactgtt | 1620 |
| cacaacattc tgccacatga cctaattttt agaggcccaa atgttgtgac actctaa | 1677 |

<210> SEQ ID NO 10
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 10

| | |
|---|---|
| atgtccttgt ctaaggaagt taagagcttc caatggacgc aagcattgag aagagaattg | 60 |
| cagagcttca catcagatgt gaaggctgct gtcattaagg atgcaaccaa ccttctgaat | 120 |
| gggttggact ctctctgaggt cagcaatgtt cagaggatca tgaggaagga aaagagagat | 180 |
| gacaaagacc tacagagact cagaagtctc aaccagactg tacattctct tgtggattta | 240 |
| aagtcaacat caaagaagaa tgttttgaaa gtggggaggc tcagtgcaga gaactgatg | 300 |
| tctcttgcgg ctgaccttga gaagctgaag gccaagatca tgaggtctga aaggccccag | 360 |
| gcttcagggg tatatatggg gaacttaaca acacagcaac tagaccaaag atctcagatc | 420 |
| ctacagatag ttgggatgag aaagcctcag cagggtgcaa gtggtgtggt aagagtttgg | 480 |
| gatgtgaaag actcatcact tttgaacaat caatttggca caatgccaag tctaactatg | 540 |
| gcttgtatgg ccaaacagtc acagactccg ctcaatgacg ttgtacaagc gctcacagac | 600 |
| cttggcttgc tttacacagt caagtatcca aatcttaatg atcttgaaag gctgaaagac | 660 |
| aagcacccag ttctgggggt catcactgaa cagcagtcca gcatcaacat ttctggctat | 720 |
| aactttagtc ttggtgctgc cgtgaaggca ggggcagccc tgttggatgg gggtaacatg | 780 |
| ttagagtcaa ttttgatcaa gccaagcaat tcggaagatt tattaaaagc ggtattaggt | 840 |
| gcgaaacgta aattaaatat gtttgtatcg gatcaagtag gtgatcgtaa tccgtatgaa | 900 |
| aatatattat ataaagtatg tttatcgggt gaaggttggc cgtatatagc gtgtcgtacg | 960 |
| tcgatagtag gtcgtgcgtg ggaaaatacg acgatagatt taacgtcgga aaaaccggcg | 1020 |
| gtaaattcgc gcgtccggc gccgggtgcg gcgggtccgc cgcaagtagg tttatcgtat | 1080 |
| tcgcaaacga tgttattaaa agatttaatg ggtggtatag atccgaatgc gccgacgtgg | 1140 |
| atagatatag aaggtcgttt taatgatccg gtagaaatag cgatatttca accgcaaaat | 1200 |
| ggtcaattta tacatttta tcgtgaaccg gtagatcaaa acaatttaa acaagattcc | 1260 |
| aagtactcac acggcatgga tcttgccgac ctcttcaatg cgcaacccgg ttgacctcg | 1320 |
| tcagttatag gtgctcttcc gcaggggatg gttctaagct gtcaaggctc cgatgacatc | 1380 |
| agaaagcttc tggactcaca gaataggaag gacattaagc ttatcgatgt tgaaatgacc | 1440 |

```
agggaagctt cgagggagta tgaagacaaa gtgtgggaca aatatggctg gttgtgtaag    1500
atgcatactg gaatagtaag ggacaaaaag aagaaagaga tcaccccgca ctgtgcactc    1560
atggactgca tcattttga aagcgcctcc aaagcaaggc tcccagatct gaaaactgtt     1620
cacaacattc tgccacatga cctaattttt agaggcccaa atgttgtgac actctaa      1677
```

<210> SEQ ID NO 11
<211> LENGTH: 1677
<212> TYPE: DNA
<213> ORGANISM: Artificial Sequence
<220> FEATURE:
<223> OTHER INFORMATION: Chemically synthesized

<400> SEQUENCE: 11

```
atgtccttgt ctaaggaagt taagagcttc aatggacgc aagcattgag aagagaattg      60
cagagcttca catcagatgt gaaggctgct gtcattaagg atgcaaccaa ccttctgaat    120
gggttggact tctctgaggt cagcaatgtt cagaggatca tgaggaagga aaagagagat    180
gacaaagacc tacagagact cagaagtctc aaccagactg tacattctct tgtggattta    240
aagtcaacat caaagaagaa tgttttgaaa gtggggaggc tcagtgcaga agaactgatg    300
tctcttgcgg ctgaccttga gaagctgaag gccaagatca tgaggtctga aaggccccag    360
gcttcagggg tatatatggg gaacttaaca acacagcaac tagaccaaag atctcagatc    420
ctacagatag ttgggatgag aaagcctcag cagggtgcaa gtggtgtggt aagagtttgg    480
gatgtgaaag actcatcact tttgaacaat caatttggca caatgccaag tctaactatg    540
gcttgtatgg ccaaacagtc acagactccg ctcaatgacg ttgtacaagc gctcacagac    600
cttggcttgc tttacacagt caagtatcca aatttaaatg atttagaacg tttaaaagat    660
aaacatccgg tattaggtgt aataacggaa cagcaatcgt cgataaatat atcgggttat    720
aatttttcgt taggtgcggc ggtaaaagcg ggtgcggcgt tattagatgg tggtaatatg    780
ttagaatcga tattaataaa accgtcgaat tcggaagatt tattaaaagc ggtattaggt    840
gcgaaacgta aattaaatat gtttgtatcg gatcaagtag gtgatcgtaa tccgtatgaa    900
aatatattat ataaagtatg tttatcgggt gaaggttggc cgtatatagc gtgtcgtacg    960
tcgatagtag gtcgtgcgtg ggaaaatacg acgatagatt taacgtcgga aaaaccggcg   1020
gtaaattcgc cgcgtccggc gccgggtgcg gcgggtccgc cgcaagtagg tttatcgtat   1080
tcgcaaacga tgttattaaa agatttaatg ggtggtatag atccgaatgc gccgacgtgg   1140
atagatatag aaggtcgttt taatgatccg gtagaaatag cgatatttca accgcaaaat   1200
ggtcaattta tacatttta tcgtgaaccg gtagatcaaa aacaatttaa acaagattcc   1260
aagtactcac acggcatgga tcttgccgac ctcttcaatg cgcaacccgg gttgacctcg   1320
tcagttatag gtgctcttcc gcaggggatg gttctaagct gtcaaggctc cgatgacatc    1380
agaaagcttc tggactcaca gaataggaag gacattaagc ttatcgatgt tgaaatgacc    1440
agggaagctt cgagggagta tgaagacaaa gtgtgggaca aatatggctg gttgtgtaag   1500
atgcatactg gaatagtaag ggacaaaaag aagaaagaga tcaccccgca ctgtgcactc   1560
atggactgca tcattttga aagcgcctcc aaagcaaggc tcccagatct gaaaactgtt    1620
cacaacattc tgccacatga cctaattttt agaggcccaa atgttgtgac actctaa     1677
```

<210> SEQ ID NO 12
<211> LENGTH: 1497
<212> TYPE: DNA
<213> ORGANISM: Lymphocytic choriomeningitis virus

<400> SEQUENCE: 12

```
atgggtcaga ttgtgacaat gtttgaggct ctgcctcaca tcatcgatga ggtgatcaac      60
attgtcatta ttgtgcttat cgtgatcacg ggtatcaagg ctgtctacaa ttttgccacc     120
tgtgggatat tcgcattgat cagtttccta cttctggctg gcaggtcctg tggcatgtac     180
ggtcttaagg gacccgacat ttacaaagga gtttaccaat ttaagtcagt ggagtttgat     240
atgtcacatc tgaacctgac catgcccaac gcatgttcag ccaacaactc ccaccattac     300
atcagtatgg ggacttctgg actagaattg accttcacca tgattccat catcagtcac      360
aacttttgca atctgacctc tgccttcaat aaaaagacct tgaccacac actcatgagt      420
atagtttcga gcctacacct cagtatcaga gggaactcca actataaggc agtatcctgc     480
gacttcaaca atggcataac catccaatac aacttgacat tctcaaatgc acaaagtgct     540
cagagccagt gtagaacctt cagaggtaga gtcctagata tgtttagaac tgccttcggg     600
gggaaataca tgaggagtgg ctggggctgg acaggctcag atggcaagac cacctggtgt     660
agccagacga gttaccaata cctgattata caaaatagaa cctgggaaaa ccactgcaca     720
tatgcaggtc ctttgggat gtccaggatt ctccttccc aagagaagac taagttcttc       780
actaggagac tagcgggcac attcacctgg actttgtcag actcttcagg ggtggagaat     840
ccaggtggtt attgcctgac caaatggatg attcttgctg cagagcttaa gtgtttcggg     900
aacacagcag ttgcgaaatg caatgtaaat catgatgaag aattctgtga catgctgcga     960
ctaattgact acaacaaggc tgctttgagt aagttcaaag aggacgtaga atctgccttg    1020
cacttattca aaacaacagt gaattctttg atttcagatc aactactgat gaggaaccac    1080
ttgagagatc tgatgggggt gccatattgc aattactcaa agttttggta cctagaacat    1140
gcaaagaccg gcgaaactag tgtccccaag tgctggcttg tcaccaatgg ttcttactta    1200
aatgagaccc acttcagtga tcaaatcgaa caggaagccg ataacatgat tacagagatg    1260
ttgaggaagg attacataaa gaggcagggg agtaccccc tagcattgat ggaccttctg      1320
atgttttcca catctgcata tctagtcagc atcttcctgc accttgtcaa ataccaaca     1380
cacaggcaca taaaggtgg ctcatgtcca agccacacc gattaaccaa caaaggaatt      1440
tgtagttgtg gtgcatttaa ggtgcctggt gtaaaaaccg tctggaaaag acgctga       1497
```

<210> SEQ ID NO 13
<211> LENGTH: 1497
<212> TYPE: DNA
<213> ORGANISM: Artificial Sequence
<220> FEATURE:
<223> OTHER INFORMATION: Chemically synthesized

<400> SEQUENCE: 13

```
atgggtcaaa tagtaacgat gtttgaagcg ttaccgcata taatagatga agtaataaat      60
atagtaataa tagtattaat agtaataacg ggtataaaag cggtatataa ttttgcgacg     120
tgtggtatat ttgcgttaat atcgtttttta ttattagcgg gtcgttcgtg tggtatgtat    180
ggtttaaaag gtccggatat atataaaggt gtatatcaat ttaaatcggt agaatttgat     240
atgtcgcatt taaatttaac gatgccgaat gcgtgttcgg cgaataattc gcatcattat     300
atatcgatgg gtacgtcggg tttagaatta acgtttacga tgattcgat aatatcgcat       360
aattttgtta atttaacgtc ggcgtttaat aaaaaaacgt tgatcatac gttaatgtcg      420
atagtatcgt cgttacattt atcgatacgt ggtaattcga attataaagc ggtatcgtgt     480
```

```
gattttaata atggtataac gatacaatat aatttaacgt tttcgaatgc gcaatcggcg    540
caatcgcaat gtcgtacgtt tcgtggtcgt gtattagata tgtttcgtac ggcgtttggt    600
ggtaaatata tgcgttcggg ttggggttgg acgggttcgg atggtaaaac gacgtggtgt    660
tcgcaaacgt cgtatcaata tttaataata caaaatcgta cgtgggaaaa tcattgtacg    720
tatgcgggtc cgtttggtat gtcgcgtata ttattatcgc aagaaaaaac gaaatttttt    780
acgcgtcgtt tagcgggtac gtttacgtgg acgttatcgg attcgtcggg tgtagaaaat    840
ccgggtggtt attgtttaac gaaatggatg atattagcgg cggaattaaa atgttttggt    900
aatacggcgg tagcgaaatg taatgtaaat catgatgaag aattttgtga tatgttacgt    960
ttaatagatt ataataaagc ggcgttatcg aaatttaaag aagatgtaga atcggcgtta   1020
catttattta aaacgacggt aaattcgtta atatcggatc aattattaat gcgtaatcat   1080
ttacgtgatt taatgggggt accgtattgt aattattcga aattttggta tttagaacat   1140
gcgaaaacgg gtgaaacgtc ggtaccgaaa tgttggttag taacgaatgg ttcgtattta   1200
aatgaaacgc attttcgga tcaaatagaa caagaagcgg ataatatgat aacgaaaatg   1260
ttacgtaaag attatataaa acgtcaaggt tcgacgccgt tagcgttaat ggatttatta   1320
atgttttcga cgtcggcgta tttagtatcg atatttttac atttagtaaa aataccgacg   1380
catcgtcata taaaaggtgg ttcgtgtccg aaaccgcatc gtttaacgaa taaaggtata   1440
tgttcgtgtg gtgcgtttaa agtaccgggt gtaaaaacgg tatggaaacg tcgttga      1497
```

<210> SEQ ID NO 14
<211> LENGTH: 273
<212> TYPE: DNA
<213> ORGANISM: Lymphocytic choriomeningitis virus

<400> SEQUENCE: 14

```
atgggtcaag gcaagtccag agaggagaaa ggcaccaata gtacaaacag ggccgaaatc     60
ctaccagata ccacctatct tggccctta agctgcaaat cttgctggca gaaatttgac    120
agcttggtaa gatgccatga ccactacctt tgcaggcact gtttaaacct tctgctgtca    180
gtatccgaca ggtgtcctct ttgtaaatat ccattaccaa ccagattgaa gatatcaaca    240
gccccaagct ctccacctcc ctacgaagag taa                                 273
```

<210> SEQ ID NO 15
<211> LENGTH: 273
<212> TYPE: DNA
<213> ORGANISM: Artificial Sequence
<220> FEATURE:
<223> OTHER INFORMATION: Chemically synthesized

<400> SEQUENCE: 15

```
atgggtcaag gtaaatcgcg tgaagaaaaa ggtacgaatt cgacgaatcg tgcggaaata     60
ttaccggata cgacgtattt aggtccgtta tcgtgtaaat cgtgttggca aaaatttgat    120
tcgttagtac gttgtcatga tcattattta tgtcgtcatt gtttaaattt attattatcg    180
gtatcggatc gttgtccgtt atgtaaatat ccgttaccga cgcgtttaaa aatatcgacg    240
gcgccgtcgt cgccgccgcc gtatgaagaa taa                                 273
```

<210> SEQ ID NO 16
<211> LENGTH: 273
<212> TYPE: DNA
<213> ORGANISM: Artificial Sequence
<220> FEATURE:
<223> OTHER INFORMATION: Chemically synthesized

<400> SEQUENCE: 16

```
atgggtcaag gtaaatcgcg tgaagaaaaa ggtacgaatt cgacgaatcg tgcggaaata      60
ttaccggata cgacgtattt aggtccgtta tcgtgtaaat cgtgttggca aaaatttgat     120
tcgttagtac gttgtcatga ccactacctt tgcaggcact gtttaaacct tctgctgtca     180
gtatccgaca ggtgtcctct ttgtaaatat ccattaccaa ccagattgaa gatatcaaca     240
gccccaagct ctccacctcc ctacgaagag taa                                   273
```

<210> SEQ ID NO 17
<211> LENGTH: 273
<212> TYPE: DNA
<213> ORGANISM: Artificial Sequence
<220> FEATURE:
<223> OTHER INFORMATION: Chemically synthesized

<400> SEQUENCE: 17

```
atgggtcaag gtaaatcgcg tgaagaaaaa ggtacgaatt cgacgaatcg tgcggaaata      60
ttaccggata cgacgtattt aggtccgtta tcgtgtaaat cgtgttggca aaaatttgat     120
tcgttagtac gttgtcatga tcattattta tgtcgtcatt gtttaaattt attattatcg     180
gtatcggatc gttgtccgtt atgtaaatat ccgttaccga ccagattgaa gatatcaaca     240
gccccaagct ctccacctcc ctacgaagag taa                                   273
```

<210> SEQ ID NO 18
<211> LENGTH: 273
<212> TYPE: DNA
<213> ORGANISM: Artificial Sequence
<220> FEATURE:
<223> OTHER INFORMATION: Chemically synthesized

<400> SEQUENCE: 18

```
atgggtcaag gcaagtccag agaggagaaa ggcaccaata gtacaaacag ggccgaaatc      60
ctaccagata ccacctatct tggccctttta agctgcaaat cttgctggca gaaatttgac    120
agcttggtaa gatgccatga ccactacctt tgcaggcact gtttaaacct tctgctgtca     180
gtatccgaca ggtgtcctct ttgtaaatat ccattaccaa cgcgtttaaa aatatcgacg     240
gcgccgtcgt cgccgccgcc gtatgaagaa taa                                   273
```

<210> SEQ ID NO 19
<211> LENGTH: 273
<212> TYPE: DNA
<213> ORGANISM: Artificial Sequence
<220> FEATURE:
<223> OTHER INFORMATION: Chemically synthesized

<400> SEQUENCE: 19

```
atgggtcaag gcaagtccag agaggagaaa ggcaccaata gtacaaacag ggccgaaatc      60
ctaccagata ccacctatct tggccctttta agctgcaaat cttgctggca gaaatttgac    120
agcttggtaa gatgccatga tcattattta tgtcgtcatt gtttaaattt attattatcg     180
gtatcggatc gttgtccgtt atgtaaatat ccgttaccga cgcgtttaaa aatatcgacg     240
gcgccgtcgt cgccgccgcc gtatgaagaa taa                                   273
```

<210> SEQ ID NO 20
<211> LENGTH: 273
<212> TYPE: DNA
<213> ORGANISM: Artificial Sequence
<220> FEATURE:

<223> OTHER INFORMATION: Chemically synthesized

<400> SEQUENCE: 20

```
atgggtcaag gtaaatcgcg tgaagaaaaa ggtacgaatt cgacgaatcg tgcggaaata      60
ttaccggata cgacgtattt aggtccgtta tcgtgtaaat cgtgttggca aaaatttgat     120
tcgttagtac gttgtcatga ccactacctt tgcaggcact gtttaaacct tctgctgtca     180
gtatccgaca ggtgtcctct ttgtaaatat ccattaccaa cgcgtttaaa aatatcgacg     240
gcgccgtcgt cgccgccgcc gtatgaagaa taa                                  273
```

<210> SEQ ID NO 21
<211> LENGTH: 558
<212> TYPE: PRT
<213> ORGANISM: Lymphocytic choriomeningitis virus

<400> SEQUENCE: 21

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
        115                 120                 125

Leu Thr Thr Gln Gln Leu Asp Gln Arg Ser Gln Ile Leu Gln Ile Val
    130                 135                 140

Gly Met Arg Lys Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
        195                 200                 205

Tyr Pro Asn Leu Asn Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
        275                 280                 285

Val Ser Asp Gln Val Gly Asp Arg Asn Pro Tyr Glu Asn Ile Leu Tyr
    290                 295                 300
```

```
Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
            325                 330                 335

Glu Lys Pro Ala Val Asn Ser Pro Arg Pro Ala Pro Gly Ala Ala Gly
            340                 345                 350

Pro Pro Gln Val Gly Leu Ser Tyr Ser Gln Thr Met Leu Leu Lys Asp
            355                 360                 365

Leu Met Gly Gly Ile Asp Pro Asn Ala Pro Thr Trp Ile Asp Ile Glu
370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Val Asp Gln Lys Gln Phe
            405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
            435                 440                 445

Gly Met Val Leu Ser Cys Gln Gly Ser Asp Asp Ile Arg Lys Leu Leu
450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
            485                 490                 495

Trp Leu Cys Lys Met His Thr Gly Ile Val Arg Asp Lys Lys Lys Lys
            500                 505                 510

Glu Ile Thr Pro His Cys Ala Leu Met Asp Cys Ile Ile Phe Glu Ser
            515                 520                 525

Ala Ser Lys Ala Arg Leu Pro Asp Leu Lys Thr Val His Asn Ile Leu
530                 535                 540

Pro His Asp Leu Ile Phe Arg Gly Pro Asn Val Val Thr Leu
545                 550                 555

<210> SEQ ID NO 22
<211> LENGTH: 498
<212> TYPE: PRT
<213> ORGANISM: Lymphocytic choriomeningitis virus

<400> SEQUENCE: 22

Met Gly Gln Ile Val Thr Met Phe Glu Ala Leu Pro His Ile Ile Asp
1               5                   10                  15

Glu Val Ile Asn Ile Val Ile Ile Val Leu Ile Val Ile Thr Gly Ile
            20                  25                  30

Lys Ala Val Tyr Asn Phe Ala Thr Cys Gly Ile Phe Ala Leu Ile Ser
        35                  40                  45

Phe Leu Leu Leu Ala Gly Arg Ser Cys Gly Met Tyr Gly Leu Lys Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
            85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
            115                 120                 125
```

-continued

```
Phe Asn Lys Lys Thr Phe Asp His Thr Leu Met Ser Ile Val Ser Ser
    130                 135                 140
Leu His Leu Ser Ile Arg Gly Asn Ser Asn Tyr Lys Ala Val Ser Cys
145                 150                 155                 160
Asp Phe Asn Asn Gly Ile Thr Ile Gln Tyr Asn Leu Thr Phe Ser Asn
                165                 170                 175
Ala Gln Ser Ala Gln Ser Gln Cys Arg Thr Phe Arg Gly Arg Val Leu
            180                 185                 190
Asp Met Phe Arg Thr Ala Phe Gly Gly Lys Tyr Met Arg Ser Gly Trp
        195                 200                 205
Gly Trp Thr Gly Ser Asp Gly Lys Thr Thr Trp Cys Ser Gln Thr Ser
    210                 215                 220
Tyr Gln Tyr Leu Ile Ile Gln Asn Arg Thr Trp Glu Asn His Cys Thr
225                 230                 235                 240
Tyr Ala Gly Pro Phe Gly Met Ser Arg Ile Leu Leu Ser Gln Glu Lys
                245                 250                 255
Thr Lys Phe Phe Thr Arg Arg Leu Ala Gly Thr Phe Thr Trp Thr Leu
            260                 265                 270
Ser Asp Ser Ser Gly Val Glu Asn Pro Gly Gly Tyr Cys Leu Thr Lys
        275                 280                 285
Trp Met Ile Leu Ala Ala Glu Leu Lys Cys Phe Gly Asn Thr Ala Val
    290                 295                 300
Ala Lys Cys Asn Val Asn His Asp Glu Glu Phe Cys Asp Met Leu Arg
305                 310                 315                 320
Leu Ile Asp Tyr Asn Lys Ala Ala Leu Ser Lys Phe Lys Glu Asp Val
                325                 330                 335
Glu Ser Ala Leu His Leu Phe Lys Thr Thr Val Asn Ser Leu Ile Ser
            340                 345                 350
Asp Gln Leu Leu Met Arg Asn His Leu Arg Asp Leu Met Gly Val Pro
        355                 360                 365
Tyr Cys Asn Tyr Ser Lys Phe Trp Tyr Leu Glu His Ala Lys Thr Gly
    370                 375                 380
Glu Thr Ser Val Pro Lys Cys Trp Leu Val Thr Asn Gly Ser Tyr Leu
385                 390                 395                 400
Asn Glu Thr His Phe Ser Asp Gln Ile Glu Gln Glu Ala Asp Asn Met
                405                 410                 415
Ile Thr Glu Met Leu Arg Lys Asp Tyr Ile Lys Arg Gln Gly Ser Thr
            420                 425                 430
Pro Leu Ala Leu Met Asp Leu Leu Met Phe Ser Thr Ser Ala Tyr Leu
        435                 440                 445
Val Ser Ile Phe Leu His Leu Val Lys Ile Pro Thr His Arg His Ile
    450                 455                 460
Lys Gly Gly Ser Cys Pro Lys Pro His Arg Leu Thr Asn Lys Gly Ile
465                 470                 475                 480
Cys Ser Cys Gly Ala Phe Lys Val Pro Gly Val Lys Thr Val Trp Lys
                485                 490                 495
Arg Arg
```

```
<210> SEQ ID NO 23
<211> LENGTH: 90
<212> TYPE: PRT
<213> ORGANISM: Lymphocytic choriomeningitis virus

<400> SEQUENCE: 23
```

Met Gly Gln Gly Lys Ser Arg Glu Glu Lys Gly Thr Asn Ser Thr Asn
1               5                   10                  15

Arg Ala Glu Ile Leu Pro Asp Thr Thr Tyr Leu Gly Pro Leu Ser Cys
                20                  25                  30

Lys Ser Cys Trp Gln Lys Phe Asp Ser Leu Val Arg Cys His Asp His
            35                  40                  45

Tyr Leu Cys Arg His Cys Leu Asn Leu Leu Ser Val Ser Asp Arg
        50                  55                  60

Cys Pro Leu Cys Lys Tyr Pro Leu Pro Thr Arg Leu Lys Ile Ser Thr
65                  70                  75                  80

Ala Pro Ser Ser Pro Pro Tyr Glu Glu
                85                  90

<210> SEQ ID NO 24
<211> LENGTH: 1476
<212> TYPE: DNA
<213> ORGANISM: Lassa virus

<400> SEQUENCE: 24
atgggacaaa tagtgacatt cttccaggaa gtgcctcatg taatagaaga ggtgatgaac      60
attgttctca ttgcactgtc tgtactagca gtgctgaaag gtctgtacaa ttttgcaacg     120
tgtggccttg ttggtttggt cactttcctc ctgttgtgtg gtaggtcttg cacaaccagt     180
ctttataaag gggtttatga gcttcagact ctggaactaa acatggagac actcaatatg     240
accatgcctc tctcctgcac aaagaacaac agtcatcatt atataatggt gggcaatgag     300
acaggactag aactgacctt gaccaacacg agcattatta atcacaaatt ttgcaatctg     360
tctgatgccc acaaaaagaa cctctatgac cacgctctta tgagcataat ctcaactttc     420
cacttgtcca tccccaactt caatcagtat gaggcaatga gctgcgattt taatgggga      480
aagattagtg tgcagtacaa cctgagtcac agctatgctg gggatgcagc caaccattgt    540
ggtactgttg caaatggtgt gttacagact tttatgagga tggcttgggg tgggagctac    600
attgctcttg actcaggccg tggcaactgg gactgtatta tgactagtta tcaatatctg    660
ataatccaaa atacaacctg ggaagatcac tgccaattct cgagaccatc tcccatcggt   720
tatctcgggc tcctctcaca aaggactaga gatatttata ttagtagaag attgctaggc    780
acattcacat ggacactgtc agattctgaa ggtaaagaca caccaggggg atattgtctg    840
accaggtgga tgctaattga ggctgaacta aaatgcttcg ggaacacagc tgtggcaaaa    900
tgtaatgaga agcatgatga ggaattttgt gacatgctga ggctgtttga cttcaacaaa    960
caagccattc aaaggttgaa agctgaagca caaatgagca ttcagttgat caacaaagca   1020
gtaaatgctt tgataaatga ccaacttata atgaagaacc atctacggga catcatggga   1080
attccatact gtaattacag caagtattgg tacctcaacc acacaactac tgggagaaca   1140
tcactgccca atgttggct tgtatcaaat ggttcatact tgaacgagac ccactttct    1200
gatgatattg aacaacaagc tgacaatatg atcactgaga tgttacagaa ggagtatatg    1260
gagaggcagg ggaagacacc attgggtcta gttgacctct tgtgttcag tacaagtttc    1320
tatcttatta gcatcttcct tcacctagtc aaaataccaa ctcataggca tattgtaggc   1380
aagtcgtgtc ccaaacctca cagattgaat catatgggca tttgttcctg tggactctac    1440
aaacagcctg gtgtgcctgt gaaatggaag agatga                              1476

<210> SEQ ID NO 25

<211> LENGTH: 1479
<212> TYPE: DNA
<213> ORGANISM: Artificial Sequence
<220> FEATURE:
<223> OTHER INFORMATION: Chemically synthesized

<400> SEQUENCE: 25

| | |
|---|---|
| atgggtcaaa tagtaacgtt ttttcaagaa gtaccgcatg taatagaaga agtaatgaat | 60 |
| atagtactaa tagcgctatc ggtactagcg gtactaaaag gtctatataa ttttgcgacg | 120 |
| tgtggtctag taggtctagt aacgtttcta ctactatgtg gtcgttcgtg tacgacgtcg | 180 |
| ctatataaag gtgtatatga actacaaacg ctagaactaa atatggaaac gctaaatatg | 240 |
| acgatgccgc tatcgtgtac gaaaaataat tcgcatcatt atataatggt aggtaatgaa | 300 |
| acgggtctag aactaacgct aacgaatacg tcgataataa atcataaatt ttgtaatcta | 360 |
| tcggatgcgc ataaaaaaaa tctatatgat catgcgctaa tgtcgataat atcgacgttt | 420 |
| cacctatcga tacccaattt taatcaatat gaagcgatgt cgtgtgattt taatggtggt | 480 |
| aaaatatcgg tacaatataa tctatcgcat tcgtatgcgg gtgatgcggc gaatcattgt | 540 |
| ggtacggtag cgaatggtgt actacaaacg tttatgcgta tggcgtgggg tggttcgtat | 600 |
| atagcgctag attcgggtcg tggtaattgg gattgtataa tgacgtcgta tcaatatcta | 660 |
| ataatacaaa atacgacgtg ggaagatcat tgtcaatttt cgcgtccgtc gccgataggt | 720 |
| tatctaggtc tactatcgca acgtacgcgt gatatatata tatcgcgtcg tctactaggt | 780 |
| acgtttacgt ggacgctatc ggattcggaa ggtaaagata cgccgggtgg ttattgtcta | 840 |
| acgcgttgga tgctaataga agcggaacta aaatgttttg gtaatacggc ggtagcgaaa | 900 |
| tgtaatgaaa aacatgatga agaattttgt gatatgctac gtctatttga ttttaataaa | 960 |
| caagcgatac aacgtctaaa agcggaagcg caaatgtcga tacaactaat aaataaagcg | 1020 |
| gtaaatgcgc taataaatga tcaactaata atgaaaaatc atctacgtga tataatgggt | 1080 |
| ataccgtatt gtaattattc gaaatattgg tatctaaatc atacgacgac gggtcgtacg | 1140 |
| tcgctaccga atgttggct agtatcgaat ggttcgtatc taaatgaaac gcattttcg | 1200 |
| gatgatatag aacaacaagc ggataatatg ataacggaaa tgctacaaaa agaatatatg | 1260 |
| gaacgtcaag gtaaaacgcc gctaggtcta gtagatctat ttgtatttc gacgtcgttt | 1320 |
| tatctaatat cgatatttct acatctagta aaaataccga cgcatcgtca tatagtaggt | 1380 |
| aaatcgtgtc cgaaaccgca tcgtctaaat catatgggta tatgttcgtg tggtctatat | 1440 |
| aaacaaccgc cgggtgtacc ggtaaaatgg aaacgttga | 1479 |

<210> SEQ ID NO 26
<211> LENGTH: 491
<212> TYPE: PRT
<213> ORGANISM: Lassa virus

<400> SEQUENCE: 26

Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
                20                  25                  30

Lys Gly Leu Tyr Asn Phe Ala Thr Cys Gly Leu Val Gly Leu Val Thr
            35                  40                  45

Phe Leu Leu Leu Cys Gly Arg Ser Cys Thr Thr Ser Leu Tyr Lys Gly
        50                  55                  60

Val Tyr Glu Leu Gln Thr Leu Glu Leu Asn Met Glu Thr Leu Asn Met

-continued

```
                65                  70                  75                  80
Thr Met Pro Leu Ser Cys Thr Lys Asn Asn Ser His His Tyr Ile Met
                    85                  90                  95
Val Gly Asn Glu Thr Gly Leu Glu Leu Thr Leu Thr Asn Thr Ser Ile
                100                 105                 110
Ile Asn His Lys Phe Cys Asn Leu Ser Asp Ala His Lys Lys Asn Leu
                115                 120                 125
Tyr Asp His Ala Leu Met Ser Ile Ile Ser Thr Phe His Leu Ser Ile
            130                 135                 140
Pro Asn Phe Asn Gln Tyr Glu Ala Met Ser Cys Asp Phe Asn Gly Gly
145                 150                 155                 160
Lys Ile Ser Val Gln Tyr Asn Leu Ser His Ser Tyr Ala Gly Asp Ala
                165                 170                 175
Ala Asn His Cys Gly Thr Val Ala Asn Gly Val Leu Gln Thr Phe Met
            180                 185                 190
Arg Met Ala Trp Gly Gly Ser Tyr Ile Ala Leu Asp Ser Gly Arg Gly
        195                 200                 205
Asn Trp Asp Cys Ile Met Thr Ser Tyr Gln Tyr Leu Ile Ile Gln Asn
    210                 215                 220
Thr Thr Trp Glu Asp His Cys Gln Phe Ser Arg Pro Ser Pro Ile Gly
225                 230                 235                 240
Tyr Leu Gly Leu Leu Ser Gln Arg Thr Arg Asp Ile Tyr Ile Ser Arg
                245                 250                 255
Arg Leu Leu Gly Thr Phe Thr Trp Thr Leu Ser Asp Ser Glu Gly Lys
                260                 265                 270
Asp Thr Pro Gly Gly Tyr Cys Leu Thr Arg Trp Met Leu Ile Glu Ala
            275                 280                 285
Glu Leu Lys Cys Phe Gly Asn Thr Ala Val Ala Lys Cys Asn Glu Lys
        290                 295                 300
His Asp Glu Glu Phe Cys Asp Met Leu Arg Leu Phe Asp Phe Asn Lys
305                 310                 315                 320
Gln Ala Ile Gln Arg Leu Lys Ala Glu Ala Gln Met Ser Ile Gln Leu
                325                 330                 335
Ile Asn Lys Ala Val Asn Ala Leu Ile Asn Asp Gln Leu Ile Met Lys
                340                 345                 350
Asn His Leu Arg Asp Ile Met Gly Ile Pro Tyr Cys Asn Tyr Ser Lys
            355                 360                 365
Tyr Trp Tyr Leu Asn His Thr Thr Thr Gly Arg Thr Ser Leu Pro Lys
        370                 375                 380
Cys Trp Leu Val Ser Asn Gly Ser Tyr Leu Asn Glu Thr His Phe Ser
385                 390                 395                 400
Asp Asp Ile Glu Gln Gln Ala Asp Asn Met Ile Thr Glu Met Leu Gln
                405                 410                 415
Lys Glu Tyr Met Glu Arg Gln Gly Lys Thr Pro Leu Gly Leu Val Asp
                420                 425                 430
Leu Phe Val Phe Ser Thr Ser Phe Tyr Leu Ile Ser Ile Phe Leu His
            435                 440                 445
Leu Val Lys Ile Pro Thr His Arg His Ile Val Gly Lys Ser Cys Pro
        450                 455                 460
Lys Pro His Arg Leu Asn His Met Gly Ile Cys Ser Cys Gly Leu Tyr
465                 470                 475                 480
Lys Gln Pro Gly Val Pro Val Lys Trp Lys Arg
                485                 490
```

<210> SEQ ID NO 27
<211> LENGTH: 1458
<212> TYPE: DNA
<213> ORGANISM: Junin virus

<400> SEQUENCE: 27

```
atggggcagt tcattagctt catgcaagaa ataccaacct ttttgcagga ggcgctgaac      60
attgctcttg ttgcagtcag tctcattgcc atcattaagg gtatagtgaa tttgtacaaa     120
agtggtttat tccagttctt tgtattctta gcgcttgcag aagatcctg cacagaagaa      180
gcctttaaaa tcggactgca cactgagttc agactgtgt ccttctcaat ggtgggtctc      240
ttttccaaca atccacatga cctacctttg ttgtgtacct aaacaagag ccatctttac      300
attaaggggg gcaatgcttc atttatgatc agctttgatg atattgaagt actgttgcca      360
cagtatgatg ttataataca acatccagca gacatgagct ggtgttccaa aagtgatgat      420
caaatttggt tgtctcaatg gttcatgaat gctgtgggac atgattggca tctagaccca      480
ccatttctgt gtaggaaccg tacaaagaca gaaggcttca tcttccaagt taacacctcc      540
aagactggtg ttaatgaaaa ctatgctaag aagtttaaga ctggcatgca tcatttatat      600
agagaatatc ctgactcttg cttgaatggc aaactgtgtt taatgaaggc acaacccaca      660
agttggcctc tccaatgtcc actcgaccat gttaacacat acatttcct tacaagaggc      720
aaaaacattc aacttccaag gaggtccttg aaagcattct tctcctggtc tttgacagat      780
tcatccggca aggataccc tggaggctat tgtctagaag agtggatgct cgtagcagcc      840
aaaatgaagt gttttggcaa tactgctgta gcaaagtgca atttgaatca tgactctgaa      900
ttctgtgaca tgttgagact ttttgattac aacaaaaatg ccatcaaaac cctaaatgat      960
gaaactaaga acaagtaaa tctgatgggg cagacaatca atgccttgat atctgacaat     1020
ttattgatga aaacaaaat tagggaactg atgagtgtcc cctactgcaa ttacacaaaa     1080
ttttggtatg ttaatcacac acttttcagga caacactcat taccaaggtg ctggttaata     1140
aaaaacaaca gctatttgaa catctctgat ttccgtaatg actggatatt ggagagtgac     1200
ttcttgattt ctgaaatgct aagcaaagag tattcggaca gacagggcaa aactcctttg     1260
actttagttg acatctgttt ttggagcaca gtattcttca cagcgtcact cttccttcac     1320
ttagtgggca taccccaccca gacacatt aggggcgaag catgcccttt gccacacagg     1380
ttgaacagct gggtggttg cagatgtggt aagtacccta atctaaagaa accaacagtt     1440
tggcgtagaa gacactaa                                                 1458
```

<210> SEQ ID NO 28
<211> LENGTH: 1458
<212> TYPE: DNA
<213> ORGANISM: Artificial Sequence
<220> FEATURE:
<223> OTHER INFORMATION: Chemically synthesized

<400> SEQUENCE: 28

```
atgggtcaat ttatatcgtt tatgcaagaa ataccgacgt ttctacaaga agcgctaaat      60
atagcgctag tagcggtatc gctaatagcg ataataaaag gtatagtaaa tctatataaa     120
tcgggtctat ttcaattttt tgtatttcta gcgctagcgg tcgttcgtg tacggaagaa      180
gcgtttaaaa taggtctaca tacggaattt caaacggtat cgttttcgat ggtaggtcta     240
ttttcgaata tccgcatga tctaccgcta ctatgtacgc taaataaatc gcatctatat     300
```

-continued

```
ataaaaggtg gtaatgcgtc gtttatgata tcgtttgatg atatagaagt actactaccg    360
caatatgatg taataataca acatccggcg gatatgtcgt ggtgttcgaa atcggatgat    420
caaatatggc tatcgcaatg gtttatgaat gcggtaggtc atgattggca tctagatccg    480
ccgtttctat gtcgtaatcg tacgaaaacg gaaggtttta tatttcaagt aaatacgtcg    540
aaaacgggtg taaatgaaaa ttatgcgaaa aaatttaaaa cgggtatgca tcatctatat    600
cgtgaatatc cggattcgtg tctaaatggt aaactatgtc taatgaaagc gcaaccgacg    660
tcgtggccgc tacaatgtcc gctagatcat gtaaatacgc tacattttct aacgcgtggt    720
aaaaatatac aactaccgcg tcgttcgcta aaagcgtttt tttcgtggtc gctaacggat    780
tcgtcgggta agatacgcc gggtggttat tgtctagaag aatggatgct agtagcggcg    840
aaaatgaaat gttttggtaa tacggcggta gcgaaatgta atctaaatca tgattcggaa    900
ttttgtgata tgctacgtct atttgattat aataaaaatg cgataaaaac gctaaatgat    960
gaaacgaaaa aacaagtaaa tctaatgggt caaacgataa atgcgctaat atcggataat   1020
ctactaatga aaataaaat acgtgaacta atgtcggtac cgtattgtaa ttatacgaaa    1080
ttttggtatg taaatcatac gctatcgggt caacattcgc taccgcgttg ttggctaata   1140
aaaaataatt cgtatctaaa tatatcggat tttcgtaatg attggatact agaatcggat   1200
tttctaatat cggaaatgct atcgaaagaa tattcggatc gtcaaggtaa acgccgcta    1260 acgctagtag atatatgttt ttggtcgacg gtattttta cggcgtcgct atttctacat    1320
ctagtaggta taccgacgca tcgtcatata cgtggtgaag cgtgtccgct accgcatcgt    1380
ctaaattcgc taggtggttg tcgttgtggt aaatatccga atctaaaaaa accgacggta    1440
tggcgtcgtc gtcattaa                                                 1458
```

<210> SEQ ID NO 29
<211> LENGTH: 485
<212> TYPE: PRT
<213> ORGANISM: Junin virus

<400> SEQUENCE: 29

```
Met Gly Gln Phe Ile Ser Phe Met Gln Glu Ile Pro Thr Phe Leu Gln
1               5                   10                  15

Glu Ala Leu Asn Ile Ala Leu Val Ala Val Ser Leu Ile Ala Ile Ile
            20                  25                  30

Lys Gly Ile Val Asn Leu Tyr Lys Ser Gly Leu Phe Gln Phe Phe Val
        35                  40                  45

Phe Leu Ala Leu Ala Gly Arg Ser Cys Thr Glu Glu Ala Phe Lys Ile
    50                  55                  60

Gly Leu His Thr Glu Phe Gln Thr Val Ser Phe Ser Met Val Gly Leu
65                  70                  75                  80

Phe Ser Asn Asn Pro His Asp Leu Pro Leu Leu Cys Thr Leu Asn Lys
                85                  90                  95

Ser His Leu Tyr Ile Lys Gly Gly Asn Ala Ser Phe Met Ile Ser Phe
            100                 105                 110

Asp Asp Ile Glu Val Leu Leu Pro Gln Tyr Asp Val Ile Gln His
        115                 120                 125

Pro Ala Asp Met Ser Trp Cys Ser Lys Ser Asp Gln Ile Trp Leu
    130                 135                 140

Ser Gln Trp Phe Met Asn Ala Val Gly His Asp Trp His Leu Asp Pro
145                 150                 155                 160

Pro Phe Leu Cys Arg Asn Arg Thr Lys Thr Glu Gly Phe Ile Phe Gln
```

```
                165                 170                 175
Val Asn Thr Ser Lys Thr Gly Val Asn Glu Asn Tyr Ala Lys Lys Phe
            180                 185                 190

Lys Thr Gly Met His His Leu Tyr Arg Glu Tyr Pro Asp Ser Cys Leu
            195                 200                 205

Asn Gly Lys Leu Cys Leu Met Lys Ala Gln Pro Thr Ser Trp Pro Leu
            210                 215                 220

Gln Cys Pro Leu Asp His Val Asn Thr Leu His Phe Leu Thr Arg Gly
225                 230                 235                 240

Lys Asn Ile Gln Leu Pro Arg Arg Ser Leu Lys Ala Phe Phe Ser Trp
                245                 250                 255

Ser Leu Thr Asp Ser Ser Gly Lys Asp Thr Pro Gly Gly Tyr Cys Leu
            260                 265                 270

Glu Glu Trp Met Leu Val Ala Ala Lys Met Lys Cys Phe Gly Asn Thr
            275                 280                 285

Ala Val Ala Lys Cys Asn Leu Asn His Asp Ser Glu Phe Cys Asp Met
            290                 295                 300

Leu Arg Leu Phe Asp Tyr Asn Lys Asn Ala Ile Lys Thr Leu Asn Asp
305                 310                 315                 320

Glu Thr Lys Lys Gln Val Asn Leu Met Gly Gln Thr Ile Asn Ala Leu
                325                 330                 335

Ile Ser Asp Asn Leu Leu Met Lys Asn Lys Ile Arg Glu Leu Met Ser
            340                 345                 350

Val Pro Tyr Cys Asn Tyr Thr Lys Phe Trp Tyr Val Asn His Thr Leu
            355                 360                 365

Ser Gly Gln His Ser Leu Pro Arg Cys Trp Leu Ile Lys Asn Asn Ser
            370                 375                 380

Tyr Leu Asn Ile Ser Asp Phe Arg Asn Asp Trp Ile Leu Glu Ser Asp
385                 390                 395                 400

Phe Leu Ile Ser Glu Met Leu Ser Lys Glu Tyr Ser Asp Arg Gln Gly
                405                 410                 415

Lys Thr Pro Leu Thr Leu Val Asp Ile Cys Phe Trp Ser Thr Val Phe
            420                 425                 430

Phe Thr Ala Ser Leu Phe Leu His Leu Val Gly Ile Pro Thr His Arg
            435                 440                 445

His Ile Arg Gly Glu Ala Cys Pro Leu Pro His Arg Leu Asn Ser Leu
            450                 455                 460

Gly Gly Cys Arg Cys Gly Lys Tyr Pro Asn Leu Lys Lys Pro Thr Val
465                 470                 475                 480

Trp Arg Arg Arg His
                485

<210> SEQ ID NO 30
<211> LENGTH: 1491
<212> TYPE: DNA
<213> ORGANISM: Machupo virus

<400> SEQUENCE: 30
atggggcagc ttatcagctt ctttcaggag attcctgttt ttctacagga agctctgaac      60
atcgctttag tggctgttag tctcatagct gtcatcaaag gcatcattaa cctttacaaa     120
agtggtctct tccagttcat cttctttctc ctcctagcag ggaggtcctg ctcggatggc     180
acattcaaaa taggcctaca cactgagttc cagtcagtca cccttaccat gcagagactt     240
ttagctaacc attcaaatga gctcccatct ctctgcatgc ttaacaatag ttttattat      300
```

```
atgaggggag gtgtgaacac cttcctgatt cgtgtttctg atatttcagt cctcatgaag    360
gagtatgatg tatcaatcta tgaaccagaa gaccttggaa attgtcttaa caagtctgac    420
tcaagctggg ctattcattg gttctcaaat gctttggac atgactggct tatggatcct     480
ccaatgctat gtagaaacaa gacaaagaag gagggatcta acattcaatt caacatcagc    540
aaagctgatg atgccagagt gtatggaaag aagataagaa atggtatgag gcatctcttc    600
aggggcttcc atgacccgtg tgaggaaggg aaagtgtgct acctgaccat caatcagtgt    660
ggtgacccca gttcctttga ctactgtggc gtgaatcatc tttccaaatg tcagtttgac    720
catgtgaaca cccttcattt ccttgtgaga agtaagacac atctcaactt tgagaggtct    780
ttgaaagcat ttttctcatg gtctctgaca gactcctcag gaaggacat gccaggaggt     840 tattgtctag aggaatggat gttgatagca gccaaaatga aatgtttcgg aaacactgct    900
gttgctaaat gtaatcaaaa tcatgactca gagttctgtg atatgctgag gctattcgac    960
tataacaaga atgcaataaa gaccctcaat gatgaatcaa agaaagaaat caatcttcta   1020
agccagacag tgaatgcctt aatctcagat aatttgttaa tgaagaataa aattaaagag   1080
ctaatgagca tcccttattg taattacaca aagttttggt atgtcaatca tacccctgaca  1140 gggcagcaca ctcttccaag atgttggttg ataaggaatg gaagttatct taacacttct   1200
gaattcagga atgactggat tttagagagt gatcacctca tctcagagat gttaagtaag   1260
gaatatgctg aaaggcaagg caaaaccccca atcacattag ttgatatttg tttctggagc  1320
acaattttct tcacagcatc attgttcctt catctagtcg gaatacccac ccatcgacac   1380
ctcaaaggcg aagcctgtcc tttgcctcat aagctggaca gcttcggagg ttgtagatgt   1440
ggcaaatatc ccagattgaa gaaacccacc atctggcaca aagacatta a             1491
```

<210> SEQ ID NO 31
<211> LENGTH: 1491
<212> TYPE: DNA
<213> ORGANISM: Artificial Sequence
<220> FEATURE:
<223> OTHER INFORMATION: Chemically synthesized

<400> SEQUENCE: 31

```
atgggtcaac taatatcgtt ttttcaagaa ataccggtat ttctacaaga agcgctaaat     60
atagcgctag tagcggtatc gctaatagcg gtaataaaag gtataataaa tctatataaa    120
tcgggtctat ttcaatttat atttttttcta ctactagcgg gtcgttcgtg ttcggatggt   180
acgtttaaaa taggtctaca tacgaatttt caatcggtaa cgctaacgat gcaacgtcta    240
ctagcgaatc attcgaatga actaccgtcg ctatgtatgc taaataattc gttttattat    300
atgcgtggtg gtgtaaatac gtttctaata cgtgtatcgg atatatcggt actaatgaaa    360
gaatatgatg tatcgatata tgaaccggaa gatctaggta attgtctaaa taatcggat     420 tcgtcgtggg cgatacattg gttttcgaat gcgctaggtc atgattggct aatggatccg    480
ccgatgctat gtcgtaataa aacgaaaaaa gaaggttcga atatacaatt taatatatcg    540
aaagcggatg atgcgcgtgt atatggtaaa aaaatacgta atggtatgcg tcatctatttt   600 cgtggttttc atgatccgtg tgaagaaggt aaagtatgtt atctaacgat aaatcaatgt    660
ggtgatccgt cgtcgtttga ttattgtggt gtaaatcatc tatcgaaatg tcaatttgat    720
catgtaaata cgctacattt tctagtacgt tcgaaaacgc atctaaattt tgaacgttcg    780
ctaaaagcgt ttttttcgtg gtcgctaacg gattcgtcgg gtaaagatat gccgggtggt    840
```

```
tattgtctag aagaatggat gctaatagcg gcgaaaatga atgttttgg taatacggcg      900
gtagcgaaat gtaatcaaaa tcatgattcg gaattttgtg atatgctacg tctatttgat     960
tataataaaa atgcgataaa aacgctaaat gatgaatcga aaaagaaat aaatctacta     1020
tcgcaaacgg taaatgcgct aatatcggat aatctactaa tgaaaaataa aataaaagaa    1080
ctaatgtcga taccgtattg taattatacg aaattttggt atgtaaatca tacgctaacg    1140
ggtcaacata cgctaccgcg ttgttggcta atacgtaatg gttcgtatct aaatacgtcg    1200
gaatttcgta atgattggat actagaatcg gatcatctaa tatcggaaat gctatcgaaa    1260
gaatatgcgg aacgtcaagg taaaacgccg ataacgctag tagatatatg tttttggtcg    1320
acgatatttt ttacggcgtc gctatttcta catctagtag gtataccgac gcatcgtcat    1380
ctaaaaggtg aagcgtgtcc gctaccgcat aaactagatt cgtttggtgg ttgtcgttgt    1440
ggtaaatatc cgcgtctaaa aaaaccgacg atatggcata acgtcatta a              1491
```

<210> SEQ ID NO 32
<211> LENGTH: 496
<212> TYPE: PRT
<213> ORGANISM: Machupo virus

<400> SEQUENCE: 32

```
Met Gly Gln Leu Ile Ser Phe Phe Gln Glu Ile Pro Val Phe Leu Gln
1               5                   10                  15

Glu Ala Leu Asn Ile Ala Leu Val Ala Val Ser Leu Ile Ala Val Ile
            20                  25                  30

Lys Gly Ile Ile Asn Leu Tyr Lys Ser Gly Leu Phe Gln Phe Ile Phe
        35                  40                  45

Phe Leu Leu Leu Ala Gly Arg Ser Cys Ser Asp Gly Thr Phe Lys Ile
    50                  55                  60

Gly Leu His Thr Glu Phe Gln Ser Val Thr Leu Thr Met Gln Arg Leu
65                  70                  75                  80

Leu Ala Asn His Ser Asn Glu Leu Pro Ser Leu Cys Met Leu Asn Asn
                85                  90                  95

Ser Phe Tyr Tyr Met Arg Gly Gly Val Asn Thr Phe Leu Ile Arg Val
            100                 105                 110

Ser Asp Ile Ser Val Leu Met Lys Glu Tyr Asp Val Ser Ile Tyr Glu
        115                 120                 125

Pro Glu Asp Leu Gly Asn Cys Leu Asn Lys Ser Asp Ser Ser Trp Ala
    130                 135                 140

Ile His Trp Phe Ser Asn Ala Leu Gly His Asp Trp Leu Met Asp Pro
145                 150                 155                 160

Pro Met Leu Cys Arg Asn Lys Thr Lys Lys Glu Gly Ser Asn Ile Gln
                165                 170                 175

Phe Asn Ile Ser Lys Ala Asp Asp Ala Arg Val Tyr Gly Lys Lys Ile
            180                 185                 190

Arg Asn Gly Met Arg His Leu Phe Arg Gly Phe His Asp Pro Cys Glu
        195                 200                 205

Glu Gly Lys Val Cys Tyr Leu Thr Ile Asn Gln Cys Gly Asp Pro Ser
    210                 215                 220

Ser Phe Asp Tyr Cys Gly Val Asn His Leu Lys Cys Gln Phe Asp
225                 230                 235                 240

His Val Asn Thr Leu His Phe Leu Val Arg Ser Lys Thr His Leu Asn
                245                 250                 255

Phe Glu Arg Ser Leu Lys Ala Phe Phe Ser Trp Ser Leu Thr Asp Ser
```

|  |  |  | 260 |  |  |  | 265 |  |  |  | 270 |  |
|---|---|---|---|---|---|---|---|---|---|---|---|---|

Ser Gly Lys Asp Met Pro Gly Gly Tyr Cys Leu Glu Glu Trp Met Leu
                275                 280                 285

Ile Ala Ala Lys Met Lys Cys Phe Gly Asn Thr Ala Val Ala Lys Cys
                290                 295                 300

Asn Gln Asn His Asp Ser Glu Phe Cys Asp Met Leu Arg Leu Phe Asp
305                 310                 315                 320

Tyr Asn Lys Asn Ala Ile Lys Thr Leu Asn Asp Glu Ser Lys Lys Glu
                325                 330                 335

Ile Asn Leu Leu Ser Gln Thr Val Asn Ala Leu Ile Ser Asp Asn Leu
                340                 345                 350

Leu Met Lys Asn Lys Ile Lys Glu Leu Met Ser Ile Pro Tyr Cys Asn
                355                 360                 365

Tyr Thr Lys Phe Trp Tyr Val Asn His Thr Leu Thr Gly Gln His Thr
                370                 375                 380

Leu Pro Arg Cys Trp Leu Ile Arg Asn Gly Ser Tyr Leu Asn Thr Ser
385                 390                 395                 400

Glu Phe Arg Asn Asp Trp Ile Leu Glu Ser Asp His Leu Ile Ser Glu
                405                 410                 415

Met Leu Ser Lys Glu Tyr Ala Glu Arg Gln Gly Lys Thr Pro Ile Thr
                420                 425                 430

Leu Val Asp Ile Cys Phe Trp Ser Thr Ile Phe Phe Thr Ala Ser Leu
                435                 440                 445

Phe Leu His Leu Val Gly Ile Pro Thr His Arg His Leu Lys Gly Glu
                450                 455                 460

Ala Cys Pro Leu Pro His Lys Leu Asp Ser Phe Gly Gly Cys Arg Cys
465                 470                 475                 480

Gly Lys Tyr Pro Arg Leu Lys Lys Pro Thr Ile Trp His Lys Arg His
                485                 490                 495

<210> SEQ ID NO 33
<211> LENGTH: 1467
<212> TYPE: DNA
<213> ORGANISM: Sabia virus

<400> SEQUENCE: 33

| atgggtcaat | tgttcagctt | ttttgaagaa | gttccgaata | tcatccatga | ggctatcaac | 60 |
|---|---|---|---|---|---|---|
| atagctctga | tagcagtgag | cttaattgct | gccttgaaag | ggatgattaa | cttgtggaag | 120 |
| agtggccttt | tccaattgat | attctttttg | actctagcag | gaagatcgtg | ttcttttaga | 180 |
| attggaagga | gcacagaatt | gcaaaacata | acgtttgata | tgttgaaggt | attcgaggac | 240 |
| caccccacat | cttgcatggt | gaatcattcc | acctactatg | tccatgaaaa | caaaaatgcc | 300 |
| acttggtgtc | ttgaggtgtc | tgtgactgat | gttaccctgc | tcatggctga | acatgatcgt | 360 |
| caagtcctca | caatctgtc | aaactgtgtg | caccctgcag | ttgagcacag | aagcaggatg | 420 |
| gttggcttac | ttgagtggat | ttttagagcc | ctaaagtatg | acttcaatca | tgatccaaca | 480 |
| ccgttgtgtc | aaaagcaaac | ttcaacagtg | aatgaaacac | gtgtgcagat | aaacatcact | 540 |
| gaggggtttg | ggtctcacgg | gtttgaagat | accatccttc | aaagactagg | ggttctattc | 600 |
| ggttcaagaa | ttgcattttc | aaatatccag | gatttaggta | aaaaaaggtt | tttattgatt | 660 |
| agaaattcaa | cttggaaaaa | tcaatgcgaa | atgaatcatg | taaactccat | gcatttaatg | 720 |
| ttggcgaatg | ctggtcgctc | ttctggttct | agaagaccac | tcggcatttt | ctcctggaca | 780 |
| ataactgatg | cagtgggcaa | tgacatgcct | ggtggttatt | gtcttgaaag | atggatgcta | 840 |

```
gtgacgtcag atcttaagtg ctttggaaac acagcactag caaaatgtaa ccttgaccac      900
gattcggaat tctgtgacat gttgaaattg tttgagttca acaaaaaagc gatagagaca      960
ttgaatgaca atacaaaaaa caaggtaaac ttgctgaccc actcaattaa tgcattaata     1020
tctgacaact tactgatgaa gaatcgactt aaagaattgt tgaacactcc ttattgtaat     1080
tacaccaaat tttggtatgt caatcacaca gcatcagggg aacactcatt gccacggtgc     1140
tggcttgtta gaaataatag ctacttgaat gaaagtgaat ttagaaatga ttggattatt     1200
gagagtgatc atttattgtc tgaaatgctc aataaagaat acatagatag acagggaaag     1260
acaccgttga ctttggtgga tatctgtttc tggagcactt tgttttttcac aacaacactg    1320 tttcttcacc tggtaggctt ccaactcat agacacatac gtggtgaacc ctgcccacta     1380
ccccataggc tcaacagtag aggaggatgt agatgtggga aataccctga actaaaaaag    1440
ccaatcacct ggcacaagaa ccactag                                         1467
```

<210> SEQ ID NO 34
<211> LENGTH: 1467
<212> TYPE: DNA
<213> ORGANISM: Artificial Sequence
<220> FEATURE:
<223> OTHER INFORMATION: Chemically synthesized

<400> SEQUENCE: 34

```
atgggtcaac tattttcgtt ttttgaagaa gtaccgaata taatacatga agcgataaat       60
atagcgctaa tagcggtatc gctaatagcg gcgctaaaag gtatgataaa tctatggaaa      120
tcgggtctat ttcaactaat atttttttcta acgctagcgg gtcgttcgtg ttcgtttcgt      180
ataggtcgtt cgacggaact acaaaatata acgtttgata tgctaaaagt atttgaagat      240
catccgacgt cgtgtatggt aaatcattcg acgtattatg tacatgaaaa taaaaatgcg      300
acgtggtgtc tagaagtatc ggtaacggat gtaacgctac taatggcgga acatgatcgt      360
caagtactaa ataatctatc gaattgtgta catccggcgg tagaacatcg ttcgcgtatg      420
gtaggtctac tagaatggat atttcgtgcg ctaaaatatg attttaatca tgatccgacg      480
ccgctatgtc aaaaacaaac gtcgacggta aatgaaacgc gtgtacaaat aaatataacg      540
gaaggttttg gttcgcatgg ttttgaagat acgatactac aacgtctagg tgtactattt      600
ggttcgcgta tagcgttttc gaatatacaa gatctaggta aaaaacgttt tctactaata      660
cgtaattcga cgtggaaaaa tcaatgtgaa atgaatcatg taaattcgat gcatctaatg      720
ctagcgaatg cgggtcgttc gtcgggttcg cgtcgtccgc taggtatatt ttcgtggacg      780
ataacggatg cggtaggtaa tgatatgccg ggtggttatt gtctagaacg ttggatgcta      840
gtaacgtcgg atctaaaatg ttttggtaat acggcgctag cgaaatgtaa tctagatcat      900
gattcggaat tttgtgatat gctaaaacta tttgaattta ataaaaaagc gatagaaacg      960
ctaaatgata atacgaaaaa taagtaaatc tactaacgc attcgataaa tgcgctaata     1020
tcggataatc tactaatgaa aaatcgtcta aaagaactac taaatacgcc gtattgtaat     1080
tatacgaaat tttggtatgt aaatcatacg gcgtcgggtg aacattcgct accgcgttgt     1140
tggctagtac gtaataattc gtatctaaat gaatcggaat tcgtaatga ttggataata      1200 gaatcggatc atctactatc ggaaatgcta aataaagaat atatagatcg tcaaggtaaa     1260
acgccgctaa cgctagtaga tatatgtttt tggtcgacgc tattttttac gacgacgcta    1320
tttctacatc tagtaggttt tccgacgcat cgtcatatac gtggtgaacc gtgtccgcta     1380
```

```
ccgcatcgtc taaattcgcg tggtggttgt cgttgtggta aatatccgga actaaaaaaa    1440
ccgataacgt ggcataaaaa tcattag                                        1467
```

<210> SEQ ID NO 35
<211> LENGTH: 488
<212> TYPE: PRT
<213> ORGANISM: Sabia virus

<400> SEQUENCE: 35

```
Met Gly Gln Leu Phe Ser Phe Phe Glu Glu Val Pro Asn Ile Ile His
1               5                   10                  15

Glu Ala Ile Asn Ile Ala Leu Ile Ala Val Ser Leu Ile Ala Ala Leu
            20                  25                  30

Lys Gly Met Ile Asn Leu Trp Lys Ser Gly Leu Phe Gln Leu Ile Phe
        35                  40                  45

Phe Leu Thr Leu Ala Gly Arg Ser Cys Ser Phe Arg Ile Gly Arg Ser
    50                  55                  60

Thr Glu Leu Gln Asn Ile Thr Phe Asp Met Leu Lys Val Phe Glu Asp
65                  70                  75                  80

His Pro Thr Ser Cys Met Val Asn His Ser Thr Tyr Tyr Val His Glu
                85                  90                  95

Asn Lys Asn Ala Thr Trp Cys Leu Glu Val Ser Val Thr Asp Val Thr
            100                 105                 110

Leu Leu Met Ala Glu His Asp Arg Gln Val Leu Asn Asn Leu Ser Asn
        115                 120                 125

Cys Val His Pro Ala Val Glu His Arg Ser Arg Met Val Gly Leu Leu
    130                 135                 140

Glu Trp Ile Phe Arg Ala Leu Lys Tyr Asp Phe Asn His Asp Pro Thr
145                 150                 155                 160

Pro Leu Cys Gln Lys Gln Thr Ser Thr Val Asn Glu Thr Arg Val Gln
                165                 170                 175

Ile Asn Ile Thr Glu Gly Phe Gly Ser His Gly Phe Glu Asp Thr Ile
            180                 185                 190

Leu Gln Arg Leu Gly Val Leu Phe Gly Ser Arg Ile Ala Phe Ser Asn
        195                 200                 205

Ile Gln Asp Leu Gly Lys Lys Arg Phe Leu Leu Ile Arg Asn Ser Thr
    210                 215                 220

Trp Lys Asn Gln Cys Glu Met Asn His Val Asn Ser Met His Leu Met
225                 230                 235                 240

Leu Ala Asn Ala Gly Arg Ser Ser Gly Ser Arg Arg Pro Leu Gly Ile
                245                 250                 255

Phe Ser Trp Thr Ile Thr Asp Ala Val Gly Asn Asp Met Pro Gly Gly
            260                 265                 270

Tyr Cys Leu Glu Arg Trp Met Leu Val Thr Ser Asp Leu Lys Cys Phe
        275                 280                 285

Gly Asn Thr Ala Leu Ala Lys Cys Asn Leu Asp His Asp Ser Glu Phe
    290                 295                 300

Cys Asp Met Leu Lys Leu Phe Glu Phe Asn Lys Lys Ala Ile Glu Thr
305                 310                 315                 320

Leu Asn Asp Asn Thr Lys Asn Lys Val Asn Leu Leu Thr His Ser Ile
                325                 330                 335

Asn Ala Leu Ile Ser Asp Asn Leu Leu Met Lys Asn Arg Leu Lys Glu
            340                 345                 350

Leu Leu Asn Thr Pro Tyr Cys Asn Tyr Thr Lys Phe Trp Tyr Val Asn
```

```
                355                 360                 365
His Thr Ala Ser Gly Glu His Ser Leu Pro Arg Cys Trp Leu Val Arg
    370                 375                 380

Asn Asn Ser Tyr Leu Asn Glu Ser Glu Phe Arg Asn Asp Trp Ile Ile
385                 390                 395                 400

Glu Ser Asp His Leu Leu Ser Glu Met Leu Asn Lys Glu Tyr Ile Asp
                405                 410                 415

Arg Gln Gly Lys Thr Pro Leu Thr Leu Val Asp Ile Cys Phe Trp Ser
            420                 425                 430

Thr Leu Phe Phe Thr Thr Thr Leu Phe Leu His Leu Val Gly Phe Pro
        435                 440                 445

Thr His Arg His Ile Arg Gly Glu Pro Cys Pro Leu Pro His Arg Leu
    450                 455                 460

Asn Ser Arg Gly Gly Cys Arg Cys Gly Lys Tyr Pro Glu Leu Lys Lys
465                 470                 475                 480

Pro Ile Thr Trp His Lys Asn His
                485

<210> SEQ ID NO 36
<211> LENGTH: 1440
<212> TYPE: DNA
<213> ORGANISM: Guanarito virus

<400> SEQUENCE: 36
atggggcagt tgatcagttt cttttcaggac ataccgatct tctttgaaga agcactcaat      60
gtagccttgg ctgtggttac actgcttgcc attataaagg gcattgtgaa catttggaaa     120
tcaggaattc ttcaactgct tgtgtattta attctggcgg aagatcatg ctcttttaaa      180 gttggtcatc atacaaattt tgagtcattc acagttaatc tagggggtgt ctttcatgaa     240
ttaccttcat tatgcagggt caacaactct tacagtctaa ttaggctttc tcataacagc     300
gatcaggcat tatcagttga gtatgtagat gtacacccctg tcctcggttc atccagccct    360
accatattcg acaactatac tcaatgtata aaagactccc cagagtttga ttggattctt     420
ggatggacaa ttaaaggact gggacatgat ttttgaggg atccaagaat ctgttgtgag     480
cctaaaaaga caactaatgt tgaatttaca ttccaattga atttaacgga cagtgttgag    540
actcatcact ataggggtaa gattgaggca ggtatcagac atttgttcgg ggactacata    600
actaatgata gctatccgaa gatgtctgtg ttatgagga ataccacctg ggaaggtcaa     660
tgcccaaata gccatgtaaa tacactgaga tttttggtca aaaatgcagg ttaccttgtt    720
ggaagaaaac cactggcatt ctttagttgg tcactttctg acccaaaggg taatgatatg    780
ccaggtggtt actgtcttga aaggtggatg ttggttgctg gagatttgaa gtgctttggc   840
aacacagctg tcgccaagtg taacttaaac catgattctg agttctgtga catgttgagg    900
ctgtttgatt tcaacaagaa tgccattgaa aaactgaaca accaaaccaa aactgctgtc    960
aatatgttga ctcactcaat aaaatagtcta atatctgaca acctattgat gaggaacaaa   1020
ctgagggaga ttttgaaggt cccatactgc agctacacaa gattctggta cataaaccac   1080
acgaaatctg gtgagcactc actgcctcgg tgctggctgg ttaataatgg ttcctatttg    1140
aatgagagtg actttagaaa tgagtggatc ttggaaagtg atcacctaat agcagagatg   1200
ttaagtaaag agtaccaaga taggcagggg aaaactcctc tgacacttgt tgacctgtgt  1260
ttttggagtg caatctttt caccacaagt ctcttttttac acctggttgg gttcccaaca   1320
catagacata tacaaggtga tccgtgccct ttgcctcata ggctcgatag aaatggtgct   1380
```
tgcaggtgtg gtaggtatca aagacttggc aaacgggtaa tctggaggag aaagcattga    1440

<210> SEQ ID NO 37
<211> LENGTH: 1440
<212> TYPE: DNA
<213> ORGANISM: Artificial Sequence
<220> FEATURE:
<223> OTHER INFORMATION: Chemically synthesized

<400> SEQUENCE: 37
atgggtcaac taatatcgtt ttttcaagat ataccgatat ttttttgaaga agcgctaaat     60
gtagcgctag cggtagtaac gctactagcg ataataaaag gtatagtaaa tatatggaaa    120
tcgggtatac tacaactact agtatatcta atactagcgg gtcgttcgtg ttcgtttaaa    180
gtaggtcatc atacgaattt tgaatcgttt acggtaaatc taggtggtgt atttcatgaa    240
ctaccgtcgc tatgtcgtgt aaataattcg tattcgctaa tacgtctatc gcataattcg    300
gatcaagcgc tatcggtaga atatgtagat gtacatccgg tactaggttc gtcgtcgccg    360
acgatatttg ataattatac gcaatgtata aaagattcgc cggaatttga ttggatacta    420
ggttggacga taaaaggtct aggtcatgat tttctacgtg atccgcgtat atgttgtgaa    480
ccgaaaaaaa cgacgaatgt agaatttacg tttcaactaa atctaacgga ttcggtagaa    540
acgcatcatt atcgtggtaa aatagaagcg ggtatacgtc atctatttgg tgattatata    600
acgaatgatt cgtatccgaa aatgtcggta gtaatgcgta atacgacgtg ggaaggtcaa    660
tgtccgaatt cgcatgtaaa tacgctacgt tttctagtaa aaaatgcggg ttatctagta    720
ggtcgtaaac cgctagcgtt tttttcgtgg tcgctatcgg atccgaaagg taatgatatg    780
ccgggtggtt attgtctaga acgttggatg ctagtagcgg gtgatctaaa atgttttggt    840
aatacggcgg tagcgaaatg taatctaaat catgattcgg aattttgtga tatgctacgt    900
ctatttgatt ttaataaaaa tgcgatagaa aaactaaata tcaaacgaa acggcggta     960
aatatgctaa cgcattcgat aaattcgcta atatcggata tctactaat gcgtaataaa    1020
ctacgtgaaa tactaaaagt accgtattgt tcgtatacgc gtttttggta tataaatcat    1080
acgaaatcgg gtgaacattc gctaccgcgt tgttggctag taataatgg ttcgtatcta    1140
aatgaatcgg attttcgtaa tgaatggata ctagaatcgg atcatctaat agcggaaatg    1200
ctatcgaaag aatatcaaga tcgtcaaggt aaaacgccgc taacgctagt agatctatgt    1260
ttttggtcgg cgatattttt tacgacgtcg ctatttctac atctagtagg ttttccgacg    1320
catcgtcata taagggtga tccgtgtccg ctaccgcatc gtctagatcg taatggtgcg    1380
tgtcgttgtg gtcgttatca acgtctaggt aaacgtgtaa tatggcgtcg taaacattga    1440

<210> SEQ ID NO 38
<211> LENGTH: 479
<212> TYPE: PRT
<213> ORGANISM: Guanarito virus

<400> SEQUENCE: 38

Met Gly Gln Leu Ile Ser Phe Phe Gln Asp Ile Pro Ile Phe Phe Glu
1               5                   10                  15

Glu Ala Leu Asn Val Ala Leu Ala Val Val Thr Leu Leu Ala Ile Ile
            20                  25                  30

Lys Gly Ile Val Asn Ile Trp Lys Ser Gly Ile Leu Gln Leu Leu Val
        35                  40                  45

Tyr Leu Ile Leu Ala Gly Arg Ser Cys Ser Phe Lys Val Gly His His

```
            50                  55                  60
Thr Asn Phe Glu Ser Phe Thr Val Asn Leu Gly Gly Val Phe His Glu
 65                  70                  75                  80

Leu Pro Ser Leu Cys Arg Val Asn Asn Ser Tyr Ser Leu Ile Arg Leu
                 85                  90                  95

Ser His Asn Ser Asp Gln Ala Leu Ser Val Glu Tyr Val Asp Val His
                    100                 105                 110

Pro Val Leu Gly Ser Ser Pro Thr Ile Phe Asp Asn Tyr Thr Gln
                115                 120                 125

Cys Ile Lys Asp Ser Pro Glu Phe Asp Trp Ile Leu Gly Trp Thr Ile
            130                 135                 140

Lys Gly Leu Gly His Asp Phe Leu Arg Asp Pro Arg Ile Cys Cys Glu
145                 150                 155                 160

Pro Lys Lys Thr Thr Asn Val Glu Phe Thr Phe Gln Leu Asn Leu Thr
                    165                 170                 175

Asp Ser Val Glu Thr His His Tyr Arg Gly Lys Ile Glu Ala Gly Ile
                180                 185                 190

Arg His Leu Phe Gly Asp Tyr Ile Thr Asn Asp Ser Tyr Pro Lys Met
            195                 200                 205

Ser Val Val Met Arg Asn Thr Thr Trp Glu Gly Gln Cys Pro Asn Ser
210                 215                 220

His Val Asn Thr Leu Arg Phe Leu Val Lys Asn Ala Gly Tyr Leu Val
225                 230                 235                 240

Gly Arg Lys Pro Leu Ala Phe Phe Ser Trp Ser Leu Ser Asp Pro Lys
                    245                 250                 255

Gly Asn Asp Met Pro Gly Gly Tyr Cys Leu Glu Arg Trp Met Leu Val
                260                 265                 270

Ala Gly Asp Leu Lys Cys Phe Gly Asn Thr Ala Val Ala Lys Cys Asn
            275                 280                 285

Leu Asn His Asp Ser Glu Phe Cys Asp Met Leu Arg Leu Phe Asp Phe
            290                 295                 300

Asn Lys Asn Ala Ile Glu Lys Leu Asn Asn Gln Thr Lys Thr Ala Val
305                 310                 315                 320

Asn Met Leu Thr His Ser Ile Asn Ser Leu Ile Ser Asp Asn Leu Leu
                    325                 330                 335

Met Arg Asn Lys Leu Arg Glu Ile Leu Lys Val Pro Tyr Cys Ser Tyr
                340                 345                 350

Thr Arg Phe Trp Tyr Ile Asn His Thr Lys Ser Gly Glu His Ser Leu
            355                 360                 365

Pro Arg Cys Trp Leu Val Asn Asn Gly Ser Tyr Leu Asn Glu Ser Asp
            370                 375                 380

Phe Arg Asn Glu Trp Ile Leu Glu Ser Asp His Leu Ile Ala Glu Met
385                 390                 395                 400

Leu Ser Lys Glu Tyr Gln Asp Arg Gln Gly Lys Thr Pro Leu Thr Leu
                    405                 410                 415

Val Asp Leu Cys Phe Trp Ser Ala Ile Phe Phe Thr Thr Ser Leu Phe
                420                 425                 430

Leu His Leu Val Gly Phe Pro Thr His Arg His Ile Gln Gly Asp Pro
            435                 440                 445

Cys Pro Leu Pro His Arg Leu Asp Arg Asn Gly Ala Cys Arg Cys Gly
        450                 455                 460

Arg Tyr Gln Arg Leu Gly Lys Arg Val Ile Trp Arg Arg Lys His
465                 470                 475
```

<210> SEQ ID NO 39
<211> LENGTH: 1455
<212> TYPE: DNA
<213> ORGANISM: Chapare virus

<400> SEQUENCE: 39

```
atgggtcaac ttgtgagttt ctttcaggaa attcctaaca tcatacagga agcaatcaac      60
attgctctaa tagctgtcag cctcattgct atcctaaaag ggttggtcaa tctgtggaaa     120
agtggtttgt ttcaactcct ggtcttcctt attctagctg aaggtcctg ctcattcaaa      180
attggaagat ccacagaact ccaaaacatc acaataaaca tgttaaaggt ctttgaggac     240
catcctattt cttgcacagt gaacaaaact ctttattaca tccgtgaaag tgagaatgca     300
acatggtgtg tagagattgc tgcactggac atgtctgtct tgctctcgcc acatgatcca     360
cgtgtaatgg gcaacctatc aaactgtgtt cacccagaca ttaaacatag atcagaactt     420
ctaggtctat tggagtggat tttgagagct ctgaaatatg attttctaaa ttatccaccc     480
ctcttgtgtg aaaaagtgac atcatctgtc aatgaaacac gcattcagat aaatgtgagc     540
gatagtgcag ttctcatga tttcaaagaa accatgctcc aaaggctggc catactattt     600
ggcacaaaat tgatgtttga taaaacacct aagcagttca tagttatcag aaatcagact     660
tgggtgaatc agtgcaagtc caatcatgtc aacacgttgc atttgatgat ggctaatgct     720
gggcatgctg ttaaattaag aagattgcaa ggggtgttca cttggacgat cacagatgct     780
gctggcaacg acatgcctgg aggttattgt ttggaaaggt ggatgttagt cacatctgac     840
ctgaaatgtt ttggcaacac tgctcttgca agtgtaact taaatcatga ctctgagttc     900
tgtgacatgt tgaaactgtt tgaatttaac aaaaaagcaa ttgagtcatt gaatgacaac     960
acaaagaaca aagtcaatct attaacacat tccattaatg ctttaatttc tgacaatctt    1020
ttgatgaaga atagattaaa agagttattg gacactccct actgcaacta cacaaaattc    1080
tggtatgtca accacaccat cacaggagag cattcacttc cacgctgttg gatggttaaa    1140
aacaacagct acctcaatga agtgaatttt agaaatgatt ggattcttga gagtgaccac    1200
ttgttgtccg aaatgttgaa caaagagtat tttgacagac aagggaaaac cccaataaca    1260
cttgttgaca tctgctttg gagcacactg ttcttcacaa caacattgtt tctccatcta    1320
gtaggcttcc caactcacag acacattcag ggagaacctt gcccactgcc tcacaagctc    1380
aacagcaatg gtggatgcag gtgtggcaga tatccagaac tcaagaaacc aacaacctgg    1440
cacaggaaac actga                                                     1455
```

<210> SEQ ID NO 40
<211> LENGTH: 1455
<212> TYPE: DNA
<213> ORGANISM: Artificial Sequence
<220> FEATURE:
<223> OTHER INFORMATION: Chemically synthesized

<400> SEQUENCE: 40

```
atgggtcaac tagtatcgtt ttttcaagaa ataccgaata taatacaaga agcgataaat      60
atagcgctaa tagcggtatc gctaatagcg atactaaaag gtctagtaaa tctatggaaa     120
tcgggtctat ttcaactact agtatttcta atactagcgg tcgttcgtg ttcgtttaaa      180
ataggtcgtt cgacggaact acaaaatata acgataaata tgctaaaagt atttgaagat     240
catccgatat cgtgtacggt aaataaaacg ctatattata cgtgaatc ggaaaatgcg       300
```

```
acgtggtgtg tagaaatagc ggcgctagat atgtcggtac tactatcgcc gcatgatccg      360
cgtgtaatgg gtaatctatc gaattgtgta catccggata taaacatcg ttcggaacta       420 ctaggtctac tagaatggat actacgtgcg ctaaatatg attttctaaa ttatccgccg       480
ctactatgtg aaaagtaac gtcgtcggta aatgaaacgc gtatacaaat aaatgtatcg       540
gattcggcgg gttcgcatga ttttaaagaa acgatgctac aacgtctagc gatactattt     600
ggtacgaaac taatgtttga taaaacgccg aaacaattta tagtaatacg taatcaaacg     660
tgggtaaatc aatgtaaatc gaatcatgta aatacgctac atctaatgat ggcgaatgcg     720
ggtcatgcgg taaaactacg tcgtctacaa ggtgtattta cgtggacgat aacggatgcg     780
gcgggtaatg atatgccggg tggttattgt ctagaacgtt ggatgctagt aacgtcggat     840
ctaaaatgtt ttggtaatac ggcgctagcg aaatgtaatc taaatcatga ttcggaattt     900
tgtgatatgc taaaactatt tgaatttaat aaaaaagcga tagaatcgct aaatgataat     960
acgaaaaata agtaaatct actaacgcat tcgataaatg cgctaatatc ggataatcta     1020
ctaatgaaaa atcgtctaaa agaactacta gatacgccgt attgtaatta tacgaaattt    1080
tggtatgtaa atcatacgat aacgggtgaa cattcgctac cgcgttgttg gatggtaaaa    1140 ataattcgt atctaaatga atcggaattt cgtaatgatt ggatactaga atcggatcat     1200
ctactatcgg aaatgctaaa taagaatat tttgatcgtc aaggtaaaac gccgataacg      1260
ctagtagata tatgttttg gtcgacgcta ttttttacga cgacgctatt tctacatcta      1320
gtaggttttc cgacgcatcg tcatatacaa ggtgaaccgt gtccgctacc gcataaacta    1380
aattcgaatg gtggttgtcg ttgtggtcgt tatccggaac taaaaaacc gacgacgtgg     1440 catcgtaaac attga                                                      1455
```

<210> SEQ ID NO 41
<211> LENGTH: 484
<212> TYPE: PRT
<213> ORGANISM: Chapare virus

<400> SEQUENCE: 41

Met Gly Gln Leu Val Ser Phe Phe Gln Glu Ile Pro Asn Ile Ile Gln
1               5                   10                  15

Glu Ala Ile Asn Ile Ala Leu Ile Ala Val Ser Leu Ile Ala Ile Leu
            20                  25                  30

Lys Gly Leu Val Asn Leu Trp Lys Ser Gly Leu Phe Gln Leu Leu Val
        35                  40                  45

Phe Leu Ile Leu Ala Gly Arg Ser Cys Ser Phe Lys Ile Gly Arg Ser
    50                  55                  60

Thr Glu Leu Gln Asn Ile Thr Ile Asn Met Leu Lys Val Phe Glu Asp
65                  70                  75                  80

His Pro Ile Ser Cys Thr Val Asn Lys Thr Leu Tyr Tyr Ile Arg Glu
                85                  90                  95

Ser Glu Asn Ala Thr Trp Cys Val Glu Ile Ala Ala Leu Asp Met Ser
            100                 105                 110

Val Leu Leu Ser Pro His Asp Pro Arg Val Met Gly Asn Leu Ser Asn
        115                 120                 125

Cys Val His Pro Asp Ile Lys His Arg Ser Glu Leu Leu Gly Leu Leu
    130                 135                 140

Glu Trp Ile Leu Arg Ala Leu Lys Tyr Asp Phe Leu Asn Tyr Pro Pro
145                 150                 155                 160

Leu Leu Cys Glu Lys Val Thr Ser Ser Val Asn Glu Thr Arg Ile Gln

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |

Ile Asn Val Ser Asp Ser Ala Gly Ser His Asp Phe Lys Glu Thr Met
                    180                 185                 190

Leu Gln Arg Leu Ala Ile Leu Phe Gly Thr Lys Leu Met Phe Asp Lys
            195                 200                 205

Thr Pro Lys Gln Phe Ile Val Ile Arg Asn Gln Thr Trp Val Asn Gln
210                 215                 220

Cys Lys Ser Asn His Val Asn Thr Leu His Leu Met Met Ala Asn Ala
225                 230                 235                 240

Gly His Ala Val Lys Leu Arg Arg Leu Gln Gly Val Phe Thr Trp Thr
                245                 250                 255

Ile Thr Asp Ala Ala Gly Asn Asp Met Pro Gly Gly Tyr Cys Leu Glu
            260                 265                 270

Arg Trp Met Leu Val Thr Ser Asp Leu Lys Cys Phe Gly Asn Thr Ala
        275                 280                 285

Leu Ala Lys Cys Asn Leu Asn His Asp Ser Glu Phe Cys Asp Met Leu
    290                 295                 300

Lys Leu Phe Glu Phe Asn Lys Lys Ala Ile Glu Ser Leu Asn Asp Asn
305                 310                 315                 320

Thr Lys Asn Lys Val Asn Leu Leu Thr His Ser Ile Asn Ala Leu Ile
                325                 330                 335

Ser Asp Asn Leu Leu Met Lys Asn Arg Leu Lys Glu Leu Leu Asp Thr
            340                 345                 350

Pro Tyr Cys Asn Tyr Thr Lys Phe Trp Tyr Val Asn His Thr Ile Thr
        355                 360                 365

Gly Glu His Ser Leu Pro Arg Cys Trp Met Val Lys Asn Asn Ser Tyr
    370                 375                 380

Leu Asn Glu Ser Glu Phe Arg Asn Asp Trp Ile Leu Glu Ser Asp His
385                 390                 395                 400

Leu Leu Ser Glu Met Leu Asn Lys Glu Tyr Phe Asp Arg Gln Gly Lys
                405                 410                 415

Thr Pro Ile Thr Leu Val Asp Ile Cys Phe Trp Ser Thr Leu Phe Phe
            420                 425                 430

Thr Thr Thr Leu Phe Leu His Leu Val Gly Phe Pro Thr His Arg His
        435                 440                 445

Ile Gln Gly Glu Pro Cys Pro Leu Pro His Lys Leu Asn Ser Asn Gly
    450                 455                 460

Gly Cys Arg Cys Gly Arg Tyr Pro Glu Leu Lys Lys Pro Thr Thr Trp
465                 470                 475                 480

His Arg Lys His

<210> SEQ ID NO 42
<211> LENGTH: 1461
<212> TYPE: DNA
<213> ORGANISM: Ocozocoautla de Espinosa virus

<400> SEQUENCE: 42

```
atgggacagt tcgtaagttt catacaagag ataccaacct tcctccagga agcgctcaac      60
atagcgttgg cagcagtgag tctcatctgt gttacaaaag gttggtgaa cttatacaga      120 tccggtctgt tccaactagt tctgttcctt cttttagctg gaaagtcctg ttcagaggaa      180
gttttcaaga taggccttca cacaaggcta caagaagtga ccctctctcc aggcgtgctt      240
ctaacaaatc atgatcacga attgccagtg ttatgttcag tgaataggac gcatctatat      300
```

```
ttcaaaggcg gcaacttcag ttttgaagtt tacattgacg atgttgttgt cctacttatg    360
gtggaaggtg gctccgacat ctccattgat tctcctaacc tcagtgcctg tctcccagat    420
ggtcaggagt ggttggtgaa ttggtggatt gaaacaattg gtcacaaatg gggtcttgac    480
ccaaacatgc tgtgcagaaa caagaccaaa cctgagggtt ttctgataca aatcaacatt    540
tcgagagccg acaacaacta tcgttatggt tggaaattaa aaaatggctt ggatcacatt    600
tacagagatc gtcaagaacc ttgccttgaa ggaaaaagat gtcttcttaa aattcggcct    660
gcaggttggc cacagagttg caacgttgac cacatgaaca ctctcaactt tctaataagg    720
ggtcaaaaga atatgtttac gagaagaact ctaaaagctt ttttctcttg gtcactcact    780
gattcctctg aagggacac cccaggaggg tattgtctgg agaaatggat gctactggca     840
gctgaaatga agtgttttgg gaacactgct attgcaaaat gcaaccaaaa tcatgattca    900
gagttctgtg atatgttacg tctatttgat tacaacaaaa atgcaattaa gacactaaat    960
gaagaaacta agaataggt taacacatta actcagatga taaatgcctt gatttcagac    1020
gatctattga tgaaaaacaa aattagagaa ttaatgaatg tgccttactg caattacaca   1080
cggttttggt atgttaatca cactctatct ggccagcact cccttccaaa atgctggatg   1140
gtaaggaata actcctactt gaatttgtct gagtttagga atgactggat tctcgaaagc   1200
gacttcctga tctctgaaat gcttagtaga gaatacttgg aaaggcaagg gaaaactccc   1260
atcactttag tagacatctg tttctggagt acgatttttt acaccagcac actgtttctt   1320
cacctcattg ggatcccaac acacagacat atccaaggtg atggctgccc tttacctcat   1380
aagctgaaca gcttgggagg gtgcagatgt ggaaaatatc ctcccttag gaaacctacc    1440
atttggtacc gcagacactg a                                             1461
```

<210> SEQ ID NO 43
<211> LENGTH: 1461
<212> TYPE: DNA
<213> ORGANISM: Artificial Sequence
<220> FEATURE:
<223> OTHER INFORMATION: Chemically synthesized

<400> SEQUENCE: 43

```
atgggtcaat tgtatcgtt tatacaagaa ataccgacgt ttctacaaga agcgctaaat     60
atagcgctag cggcggtatc gctaatatgt gtaacgaaag gtctagtaaa tctatatcgt    120
tcgggtctat ttcaactagt actatttcta ctactagcgg gtaaatcgtg ttcggaagaa    180
gtatttaaaa taggtctaca tacgcgtcta caagaagtaa cgctatcgcc gggtgtacta    240
ctaacgaatc atgatcatga actaccggta ctatgttcgg taaatcgtac gcatctatat    300
tttaaaggtg gtaattttc gtttgaagta tatatagatg atgtagtagt actactaatg    360
gtagaaggtg gttcggatat atcgatagat tcgccgaatc tatcggcgtg tctaccggat    420
ggtcaagaat ggctagtaaa ttggtggata gaaacgatag gtcataaatg gggtctagat    480
ccgaatatgc tatgtcgtaa taaaacgaaa ccggaaggtt ttctaataca aataaatata    540
tcgcgtgcgg ataataatta tcgttatggt tggaaactaa aaaatggtct agatcatata    600
tatcgtgatc gtcaagaacc gtgtctagaa ggtaaacgtt gtctactaaa atacgtccg     660
gcgggttggc cgcaatcgtg taatgtagat catatgaata cgctaaattt tctaatacgt    720
ggtcaaaaaa atatgtttac gcgtcgtacg ctaaaagcgt ttttttcgtg gtcgctaacg    780
gattcgtcgg gtcgtgatac gccgggtggt tattgtctag aaaaatggat gctactagcg    840
gcggaaatga atgttttgg taatacggcg atagcgaaat gtaatcaaaa tcatgattcg    900
```

-continued

```
gaattttgtg atatgctacg tctatttgat tataataaaa atgcgataaa aacgctaaat    960
gaagaaacga aaaatcgtgt aaatacgcta acgcaaatga taaatgcgct aatatcggat   1020
gatctactaa tgaaaaataa aatacgtgaa ctaatgaatg taccgtattg taattatacg   1080
cgttttggt atgtaaatca tacgctatcg ggtcaacatt cgctaccgaa atgttggatg   1140
gtacgtaata attcgtatct aaatctatcg gaatttcgta atgattggat actagaatcg   1200
gattttctaa tatcggaaat gctatcgcgt gaatatctag aacgtcaagg taaaacgccg   1260
ataacgctag tagatatatg tttttggtcg acgatatttt atacgtcgac gctatttcta   1320
catctaatag gtataccgac gcatcgtcat atacaaggtg atggttgtcc gctaccgcat   1380
aaactaaatt cgctaggtgg ttgtcgttgt ggtaaatatc cgccgctacg taaaccgacg   1440
atatggtatc gtcgtcattg a                                            1461
```

<210> SEQ ID NO 44
<211> LENGTH: 486
<212> TYPE: PRT
<213> ORGANISM: Ocozocoautla de Espinosa virus

<400> SEQUENCE: 44

```
Met Gly Gln Phe Val Ser Phe Ile Gln Glu Ile Pro Thr Phe Leu Gln
 1               5                  10                  15
Glu Ala Leu Asn Ile Ala Leu Ala Ala Val Ser Leu Ile Cys Val Thr
             20                  25                  30
Lys Gly Leu Val Asn Leu Tyr Arg Ser Gly Leu Phe Gln Leu Val Leu
         35                  40                  45
Phe Leu Leu Leu Ala Gly Lys Ser Cys Ser Glu Glu Val Phe Lys Ile
     50                  55                  60
Gly Leu His Thr Arg Leu Gln Glu Val Thr Leu Ser Pro Gly Val Leu
 65                  70                  75                  80
Leu Thr Asn His Asp His Glu Leu Pro Val Leu Cys Ser Val Asn Arg
                 85                  90                  95
Thr His Leu Tyr Phe Lys Gly Gly Asn Phe Ser Phe Glu Val Tyr Ile
            100                 105                 110
Asp Asp Val Val Val Leu Leu Met Val Glu Gly Gly Ser Asp Ile Ser
        115                 120                 125
Ile Asp Ser Pro Asn Leu Ser Ala Cys Leu Pro Asp Gly Gln Glu Trp
    130                 135                 140
Leu Val Asn Trp Trp Ile Glu Thr Ile Gly His Lys Trp Gly Leu Asp
145                 150                 155                 160
Pro Asn Met Leu Cys Arg Asn Lys Thr Lys Pro Glu Gly Phe Leu Ile
                165                 170                 175
Gln Ile Asn Ile Ser Arg Ala Asp Asn Tyr Arg Tyr Gly Trp Lys
            180                 185                 190
Leu Lys Asn Gly Leu Asp His Ile Tyr Arg Asp Arg Gln Glu Pro Cys
        195                 200                 205
Leu Glu Gly Lys Arg Cys Leu Leu Lys Ile Arg Pro Ala Gly Trp Pro
    210                 215                 220
Gln Ser Cys Asn Val Asp His Met Asn Thr Leu Asn Phe Leu Ile Arg
225                 230                 235                 240
Gly Gln Lys Asn Met Phe Thr Arg Arg Thr Leu Lys Ala Phe Phe Ser
                245                 250                 255
Trp Ser Leu Thr Asp Ser Ser Gly Arg Asp Thr Pro Gly Gly Tyr Cys
            260                 265                 270
```

```
Leu Glu Lys Trp Met Leu Leu Ala Ala Glu Met Lys Cys Phe Gly Asn
            275                 280                 285

Thr Ala Ile Ala Lys Cys Asn Gln Asn His Asp Ser Glu Phe Cys Asp
290                 295                 300

Met Leu Arg Leu Phe Asp Tyr Asn Lys Asn Ala Ile Lys Thr Leu Asn
305                 310                 315                 320

Glu Glu Thr Lys Asn Arg Val Asn Thr Leu Thr Gln Met Ile Asn Ala
                325                 330                 335

Leu Ile Ser Asp Asp Leu Leu Met Lys Asn Lys Ile Arg Glu Leu Met
            340                 345                 350

Asn Val Pro Tyr Cys Asn Tyr Thr Arg Phe Trp Tyr Val Asn His Thr
            355                 360                 365

Leu Ser Gly Gln His Ser Leu Pro Lys Cys Trp Met Val Arg Asn Asn
370                 375                 380

Ser Tyr Leu Asn Leu Ser Glu Phe Arg Asn Asp Trp Ile Leu Glu Ser
385                 390                 395                 400

Asp Phe Leu Ile Ser Glu Met Leu Ser Arg Glu Tyr Leu Glu Arg Gln
                405                 410                 415

Gly Lys Thr Pro Ile Thr Leu Val Asp Ile Cys Phe Trp Ser Thr Ile
            420                 425                 430

Phe Tyr Thr Ser Thr Leu Phe Leu His Leu Ile Gly Ile Pro Thr His
            435                 440                 445

Arg His Ile Gln Gly Asp Gly Cys Pro Leu Pro His Lys Leu Asn Ser
            450                 455                 460

Leu Gly Gly Cys Arg Cys Gly Lys Tyr Pro Pro Leu Arg Lys Pro Thr
465                 470                 475                 480

Ile Trp Tyr Arg Arg His
                485

<210> SEQ ID NO 45
<211> LENGTH: 1443
<212> TYPE: DNA
<213> ORGANISM: Whitewater Arroyo virus

<400> SEQUENCE: 45
atggggcagc tgatctcgtt tttcggggaa attccatcaa taatacacga ggccctgaac      60
attgcattaa tagcagtcag catcatatca attctgaagg gtgttatcaa catttggggg     120
agtggcctac tgcagttcat tgtgtttctg ctgttggctg gcgatcctg ctcatacaag      180 attggccatc atgttgaact tcaacacata attctgaatg catcctacat cacaccctat     240
gtaccaatgc cctgcatgat caatgacaca catttcttac tgaggggtcc ttttgaggcc     300
agttgggcca tcaagttgga gattactgat gtgacaactc ttgtggtgga cactgacaac     360
gttgctaatc ccacaaacat tagcaagtgt tttgcaaaca accaggatga gaggttgtta     420
ggcttcacca tggagtggtt tttgagtgga ttggaacatg atcaccattt cactccacag     480
atcatttgtg gaaatgtatc caaaggagag gttaatgctc aagtgaacat aactatggag     540
gatcattgca gtcaggtgtt tttgaaaatg agaaggattt ttggggtttt caaaaaccct     600
tgcacttcac atgggaagca gaatgtgcta atctccgtca gtaattggac caatcaatgc     660
tcagggaacc acttaagttc catgcacctt atagtgcaaa atgcatataa acaaatgatc     720
aaatcaagaa ctttgaaaag tttttttgcc tggtcactgt ctgatgccac agggactgac     780
atgccaggag ggtactgttt ggagaaatgg atgctgattt caagtgagct aaaatgtttt     840
```

| | |
|---|---:|
| ggaaacactg caatagctaa gtgcaacttg gatcacagtt cagagttttg tgacatgctc | 900 |
| aaattgtttg agtttaacag aaatgcaatc aaaacacttc agaatgacag caagcatcaa | 960 |
| ctagacatga tcataactgc tgtcaactct ctgatttcag acaatactct aatgaaaaac | 1020 |
| agacttaaag aactcatcaa cattccttat tgtaattata ctaagttctg gtatgtgaac | 1080 |
| cacactggat ttaatgtcca ttcactgcca agatgttggc tcacaaaaaa tggcagttac | 1140 |
| ttgaatgtgt ctgactttag gaatcaatgg cttttagaaa gtgaccattt gatctctgaa | 1200 |
| atcttaagta gagaatatga ggcaagacaa ggcaagacac cacttgggtt ggtggatgta | 1260 |
| tgcttctgga gcaccttgtt ttatgtttca tcgatatttt tacacctact gagaataccc | 1320 |
| acccacagac acataattgg tgaaggctgt cccaaaccac atagactttc cagtaactca | 1380 |
| gtatgtgcat gtggtctttt taaacaaaaa gggaggccct aaggtgggc cgggaaagtg | 1440 |
| tag | 1443 |

<210> SEQ ID NO 46
<211> LENGTH: 1443
<212> TYPE: DNA
<213> ORGANISM: Artificial Sequence
<220> FEATURE:
<223> OTHER INFORMATION: Chemically synthesized

<400> SEQUENCE: 46

| | |
|---|---:|
| atgggtcaac taatatcgtt ttttggtgaa ataccgtcga taatacatga agcgctaaat | 60 |
| atagcgctaa tagcggtatc gataatatcg atactaaaag gtgtaataaa tatatggggt | 120 |
| tcgggtctac tacaatttat agtatttcta ctactagcgg gtcgttcgtg ttcgtataaa | 180 |
| ataggtcatc atgtagaact acaacatata atactaaatg cgtcgtatat aacgccgtat | 240 |
| gtaccgatgc cgtgtatgat aaatgatacg cattttctac tacgtggtcc gtttgaagcg | 300 |
| tcgtgggcga taaaactaga ataacggat gtaacgacgc tagtagtaga tacggataat | 360 |
| gtagcgaatc cgacgaatat atcgaaatgt tttgcgaata atcaagatga acgtctacta | 420 |
| ggttttacga tggaatggtt tctatcgggt ctagaacatg atcatcattt tacgccgcaa | 480 |
| ataatatgtg gtaatgtatc gaaggtgaa gtaaatgcgc aagtaaatat aacgatggaa | 540 |
| gatcattgtt cgcaagtatt tctaaaaatg cgtcgtatat ttggtgtatt taaaaatccg | 600 |
| tgtacgtcgc atggtaaaca aaatgtacta atatcggtat cgaattggac gaatcaatgt | 660 |
| tcgggtaatc atctatcgtc gatgcatcta atagtacaaa atgcgtataa acaaatgata | 720 |
| aaatcgcgta cgctaaaatc gttttttgcg tggtcgctat cggatgcgac gggtacggat | 780 |
| atgccgggtg ttattgtct agaaaaatgg atgctaatat cgtcggaact aaaatgtttt | 840 |
| ggtaatacgg cgatagcgaa atgtaatcta gatcattcgt cggaattttg tgatatgcta | 900 |
| aaactatttg aatttaatcg taatgcgata aaaacgctac aaaatgattc gaaacatcaa | 960 |
| ctagatatga taataacggc ggtaaattcg ctaatatcgg ataatacgct aatgaaaaat | 1020 |
| cgtctaaaag aactaataaa tataccgtat tgtaattata cgaaattttg gtatgtaaat | 1080 |
| catacgggtt ttaatgtaca ttcgctaccg cgttgttggc taacgaaaaa tggttcgtat | 1140 |
| ctaaatgtat cggattttcg taatcaatgg ctactagaat cggatcatct aatatcggaa | 1200 |
| atactatcgc gtgaatatga agcgcgtcaa ggtaaaacgc cgctaggtct agtagatgta | 1260 |
| tgttttttggt cgacgctatt ttatgtatcg tcgatatttc tacatctact acgtataccg | 1320 |
| acgcatcgtc atataatagg tgaaggttgt ccgaaaccgc atcgtctatc gtcgaattcg | 1380 |
| gtatgtgcgt gtggtctatt taaacaaaaa ggtcgtccgc tacgttgggc gggtaaagta | 1440 | tag                                                              1443

<210> SEQ ID NO 47
<211> LENGTH: 480
<212> TYPE: PRT
<213> ORGANISM: Whitewater Arroyo virus

<400> SEQUENCE: 47

```
Met Gly Gln Leu Ile Ser Phe Phe Gly Glu Ile Pro Ser Ile Ile His
1               5                   10                  15

Glu Ala Leu Asn Ile Ala Leu Ile Ala Val Ser Ile Ile Ser Ile Leu
            20                  25                  30

Lys Gly Val Ile Asn Ile Trp Gly Ser Gly Leu Leu Gln Phe Ile Val
        35                  40                  45

Phe Leu Leu Ala Gly Arg Ser Cys Ser Tyr Lys Ile Gly His His
    50                  55                  60

Val Glu Leu Gln His Ile Ile Leu Asn Ala Ser Tyr Ile Thr Pro Tyr
65                  70                  75                  80

Val Pro Met Pro Cys Met Ile Asn Asp Thr His Phe Leu Leu Arg Gly
                85                  90                  95

Pro Phe Glu Ala Ser Trp Ala Ile Lys Leu Glu Ile Thr Asp Val Thr
            100                 105                 110

Thr Leu Val Val Asp Thr Asp Asn Val Ala Asn Pro Thr Asn Ile Ser
        115                 120                 125

Lys Cys Phe Ala Asn Asn Gln Asp Glu Arg Leu Leu Gly Phe Thr Met
    130                 135                 140

Glu Trp Phe Leu Ser Gly Leu Glu His Asp His His Phe Thr Pro Gln
145                 150                 155                 160

Ile Ile Cys Gly Asn Val Ser Lys Gly Glu Val Asn Ala Gln Val Asn
                165                 170                 175

Ile Thr Met Glu Asp His Cys Ser Gln Val Phe Leu Lys Met Arg Arg
            180                 185                 190

Ile Phe Gly Val Phe Lys Asn Pro Cys Thr Ser His Gly Lys Gln Asn
        195                 200                 205

Val Leu Ile Ser Val Ser Asn Trp Thr Asn Gln Cys Ser Gly Asn His
    210                 215                 220

Leu Ser Ser Met His Leu Ile Val Gln Asn Ala Tyr Lys Gln Met Ile
225                 230                 235                 240

Lys Ser Arg Thr Leu Lys Ser Phe Phe Ala Trp Ser Leu Ser Asp Ala
                245                 250                 255

Thr Gly Thr Asp Met Pro Gly Gly Tyr Cys Leu Glu Lys Trp Met Leu
            260                 265                 270

Ile Ser Ser Glu Leu Lys Cys Phe Gly Asn Thr Ala Ile Ala Lys Cys
        275                 280                 285

Asn Leu Asp His Ser Ser Glu Phe Cys Asp Met Leu Lys Leu Phe Glu
    290                 295                 300

Phe Asn Arg Asn Ala Ile Lys Thr Leu Gln Asn Asp Ser Lys His Gln
305                 310                 315                 320

Leu Asp Met Ile Ile Thr Ala Val Asn Ser Leu Ile Ser Asp Asn Thr
                325                 330                 335

Leu Met Lys Asn Arg Leu Lys Glu Leu Ile Asn Ile Pro Tyr Cys Asn
            340                 345                 350

Tyr Thr Lys Phe Trp Tyr Val Asn His Thr Gly Phe Asn Val His Ser
        355                 360                 365
```

```
Leu Pro Arg Cys Trp Leu Thr Lys Asn Gly Ser Tyr Leu Asn Val Ser
    370                 375                 380

Asp Phe Arg Asn Gln Trp Leu Leu Glu Ser Asp His Leu Ile Ser Glu
385                 390                 395                 400

Ile Leu Ser Arg Glu Tyr Glu Ala Arg Gln Gly Lys Thr Pro Leu Gly
                405                 410                 415

Leu Val Asp Val Cys Phe Trp Ser Thr Leu Phe Tyr Val Ser Ser Ile
            420                 425                 430

Phe Leu His Leu Leu Arg Ile Pro Thr His Arg His Ile Ile Gly Glu
        435                 440                 445

Gly Cys Pro Lys Pro His Arg Leu Ser Ser Asn Ser Val Cys Ala Cys
    450                 455                 460

Gly Leu Phe Lys Gln Lys Gly Arg Pro Leu Arg Trp Ala Gly Lys Val
465                 470                 475                 480

<210> SEQ ID NO 48
<211> LENGTH: 1365
<212> TYPE: DNA
<213> ORGANISM: Lujo virus

<400> SEQUENCE: 48
atggggcaga ttgttgccgt tttccaagct atccctgaga ttctaaacga ggcaattaac     60
attgtgataa ttgtgatcat aatgttcacc ctcatcaagg gcgttttcaa tctatacaaa    120
tccggtcttt tccagctggt catctttctc ctactctgtg gcaagcgttg tgactcatca    180
ttgctatcag gattcaatct ggagacagtt catttcaaca tgtcactgtt gagctccatc    240
cctatggtct ctgaacagca gcactgcatc cagcacaatc acagctccat aaccttcagt    300
ttgctgacca acaagtccga cttggaaaag tgcaatttca cccgcctgca agctgttgac    360
agggtgatct tgatctgtt cagagagttt catcaccgtg ttggggattt tcctgttact    420
tctgatctga aatgctctca caacaccagc tacagagtga tagaatatga agtcaccaaa    480
gagagtctcc ctcgattgca ggaagctgtg agcaccttgt tcccagacct ccatctctcc    540
gaagataggt ttctgcaaat tcaggcccat gatgacaaga actgcactgg tctacaccca    600
ttgaactacc tgaggctcct gaaagagaat tcagaaactc actacaaagt gaggaaatta    660
atgaaattgt ttcagtggtc tttgagtgat gagacaggta gccctctgcc aggtggacac    720
tgtctagaaa gatggctcat ctttgcgtct gatataaagt gctttgataa tgcagcgatt    780
gccaaatgca ataaagagca tgatgaggag ttctgtgaca tgttgaggct atttgactac    840
aacaaagcaa gtattgccaa gcttaggggc gaagcctcaa gctcgatcaa cttgttgtcg    900
gggagaatca atgccatcat ttcagacaca cttttgatga gatcatccct caagaggctg    960
atgggcatac catactgcaa ttatacaaag ttctggtatt taaaccatac aaaactgggg   1020
atacattctt taccccgatg ttggctggtt agtaatggga gttacctcaa cgaaacaaaa   1080
tttactcatg atatggaaga tgaggcagat aaactgctga ccgagatgct aaagaaagag   1140
tatgttagga gacaagagaa aacacccatt actctgatgg acatactgat gtttagtgtc   1200
tctttctata tgttttctgt aacactatgc atatgcaaca tacccaccca tcggcacatc   1260
acaggtttgc cgtgtcccaa accacacaga ctcagaaaga atggcacctg tgcctgtggc   1320
ttctttaagt caataaacag gtccactggt tgggccaaac actga                    1365

<210> SEQ ID NO 49
<211> LENGTH: 1365
```

<212> TYPE: DNA
<213> ORGANISM: Artificial Sequence
<220> FEATURE:
<223> OTHER INFORMATION: Chemically synthesized

<400> SEQUENCE: 49

```
atgggtcaaa tagtagcggt atttcaagcg ataccggaaa tactaaatga agcgataaat      60
atagtaataa tagtaataat aatgtttacg ctaataaaag gtgtatttaa tctatataaa     120
tcgggtctat ttcaactagt aatatttcta ctactatgtg gtaaacgttg tgattcgtcg     180
ctactatcgg gttttaatct agaaacggta cattttaata tgtcgctact atcgtcgata     240
ccgatggtat cggaacaaca acattgtata caacataatc attcgtcgat aacgttttcg     300
ctactaacga ataaatcgga tctagaaaaa tgtaatttta cgcgtctaca agcggtagat     360
cgtgtaatat ttgatctatt tcgtgaattt catcatcgtg taggtgattt ccggtaacg      420
tcggatctaa aatgttcgca taatacgtcg tatcgtgtaa tagaatatga agtaacgaaa     480
gaatcgctac cgcgtctaca agaagcggta tcgacgctat ttccggatct acatctatcg     540
gaagatcgtt ttctacaaat acaagcgcat gatgataaaa attgtacggg tctacatccg     600
ctaaattatc tacgtctact aaaagaaaat tcggaacgc attataaagt acgtaaacta     660
atgaaactat ttcaatggtc gctatcggat gaaacgggtt cgccgctacc gggtggtcat     720
tgtctagaac gttggctaat atttgcgtcg gatataaaat gttttgataa tgcggcgata     780
gcgaaatgta ataagaaca tgatgaagaa ttttgtgata tgctacgtct atttgattat     840
aataaagcgt cgatagcgaa actacgtggt gaagcgtcgt cgtcgataaa tctactatcg     900
ggtcgtataa atgcgataat atcggatacg ctactaatgc gttcgtcgct aaaacgtcta     960
atgggtatac cgtattgtaa ttatacgaaa ttttggtatc taaatcatac gaaactaggt    1020
atacattcgc taccgcgttg ttggctagta tcgaatggtt cgtatctaaa tgaaacgaaa    1080
tttacgcatg atatggaaga tgaagcggat aaactactaa cggaaatgct aaaaaaagaa    1140
tatgtacgtc gtcaagaaaa aacgccgata acgctaatgg atatactaat gttttcggta    1200
tcgttttata tgttttcggt aacgctatgt atatgtaata taccgacgca tcgtcatata    1260
acgggtctac cgtgtccgaa accgcatcgt ctacgtaaaa atggtacgtg tgcgtgtggt    1320
ttttttaaat cgataaatcg ttcgacgggt tgggcgaaac attga                    1365
```

<210> SEQ ID NO 50
<211> LENGTH: 454
<212> TYPE: PRT
<213> ORGANISM: Lujo virus

<400> SEQUENCE: 50

```
Met Gly Gln Ile Val Ala Val Phe Gln Ala Ile Pro Glu Ile Leu Asn
1               5                   10                  15

Glu Ala Ile Asn Ile Val Ile Ile Val Ile Ile Met Phe Thr Leu Ile
            20                  25                  30

Lys Gly Val Phe Asn Leu Tyr Lys Ser Gly Leu Phe Gln Leu Val Ile
        35                  40                  45

Phe Leu Leu Leu Cys Gly Lys Arg Cys Asp Ser Ser Leu Leu Ser Gly
    50                  55                  60

Phe Asn Leu Glu Thr Val His Phe Asn Met Ser Leu Leu Ser Ser Ile
65                  70                  75                  80

Pro Met Val Ser Glu Gln Gln His Cys Ile Gln His Asn His Ser Ser
                85                  90                  95
```

```
Ile Thr Phe Ser Leu Leu Thr Asn Lys Ser Asp Leu Glu Lys Cys Asn
            100                 105                 110

Phe Thr Arg Leu Gln Ala Val Asp Arg Val Ile Phe Asp Leu Phe Arg
            115                 120                 125

Glu Phe His His Arg Val Gly Asp Phe Pro Val Thr Ser Asp Leu Lys
            130                 135                 140

Cys Ser His Asn Thr Ser Tyr Arg Val Ile Glu Tyr Glu Val Thr Lys
145                 150                 155                 160

Glu Ser Leu Pro Arg Leu Gln Glu Ala Val Ser Thr Leu Phe Pro Asp
            165                 170                 175

Leu His Leu Ser Glu Asp Arg Phe Leu Gln Ile Gln Ala His Asp Asp
            180                 185                 190

Lys Asn Cys Thr Gly Leu His Pro Leu Asn Tyr Leu Arg Leu Leu Lys
            195                 200                 205

Glu Asn Ser Glu Thr His Tyr Lys Val Arg Lys Leu Met Lys Leu Phe
            210                 215                 220

Gln Trp Ser Leu Ser Asp Glu Thr Gly Ser Pro Leu Pro Gly Gly His
225                 230                 235                 240

Cys Leu Glu Arg Trp Leu Ile Phe Ala Ser Asp Ile Lys Cys Phe Asp
            245                 250                 255

Asn Ala Ala Ile Ala Lys Cys Asn Lys Glu His Asp Glu Glu Phe Cys
            260                 265                 270

Asp Met Leu Arg Leu Phe Asp Tyr Asn Lys Ala Ser Ile Ala Lys Leu
            275                 280                 285

Arg Gly Glu Ala Ser Ser Ile Asn Leu Leu Ser Gly Arg Ile Asn
            290                 295                 300

Ala Ile Ile Ser Asp Thr Leu Leu Met Arg Ser Ser Leu Lys Arg Leu
305                 310                 315                 320

Met Gly Ile Pro Tyr Cys Asn Tyr Thr Lys Phe Trp Tyr Leu Asn His
            325                 330                 335

Thr Lys Leu Gly Ile His Ser Leu Pro Arg Cys Trp Leu Val Ser Asn
            340                 345                 350

Gly Ser Tyr Leu Asn Glu Thr Lys Phe Thr His Asp Met Glu Asp Glu
            355                 360                 365

Ala Asp Lys Leu Leu Thr Glu Met Leu Lys Lys Glu Tyr Val Arg Arg
            370                 375                 380

Gln Glu Lys Thr Pro Ile Thr Leu Met Asp Ile Leu Met Phe Ser Val
385                 390                 395                 400

Ser Phe Tyr Met Phe Ser Val Thr Leu Cys Ile Cys Asn Ile Pro Thr
            405                 410                 415

His Arg His Ile Thr Gly Leu Pro Cys Pro Lys Pro His Arg Leu Arg
            420                 425                 430

Lys Asn Gly Thr Cys Ala Cys Gly Phe Phe Lys Ser Ile Asn Arg Ser
            435                 440                 445

Thr Gly Trp Ala Lys His
    450
```